United States Patent
Farwell et al.

(10) Patent No.: US 11,474,113 B2
(45) Date of Patent: Oct. 18, 2022

(54) METHODS OF TREATING SPINAL MUSCULAR ATROPHY

(71) Applicant: Biogen MA Inc., Cambridge, MA (US)

(72) Inventors: Wildon Farwell, Newton, MA (US); John Staropoli, Boston, MA (US); Guolin Zhao, Arlington, MA (US); Alexander McCampbell, Andover, MA (US); Christopher Cody Stebbins, Newton Highlands, MA (US)

(73) Assignee: Biosen MA Inc., Cambridge, MA (US)

( * ) Notice: Subject to any disclaimer, the term of this patent is extended or adjusted under 35 U.S.C. 154(b) by 0 days.

(21) Appl. No.: 16/963,914

(22) PCT Filed: Jan. 25, 2019

(86) PCT No.: PCT/US2019/015185
§ 371 (c)(1),
(2) Date: Jul. 22, 2020

(87) PCT Pub. No.: WO2019/147960
PCT Pub. Date: Aug. 1, 2019

(65) Prior Publication Data
US 2021/0041459 A1 Feb. 11, 2021

Related U.S. Application Data

(60) Provisional application No. 62/738,134, filed on Sep. 28, 2018, provisional application No. 62/684,507, filed on Jun. 13, 2018, provisional application No. 62/622,027, filed on Jan. 25, 2018.

(51) Int. Cl.
*G01N 33/68* (2006.01)
*C12N 15/113* (2010.01)

(52) U.S. Cl.
CPC ....... *G01N 33/6896* (2013.01); *C12N 15/113* (2013.01); *C12N 2310/11* (2013.01); *C12N 2310/315* (2013.01); *C12N 2310/321* (2013.01); *G01N 2800/28* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 8,465,727 B2 | 6/2013 | Bowser | |
| 10,385,341 B2 | 8/2019 | Swayze | |
| 10,669,546 B2 | 6/2020 | Swayze | |
| 10,968,453 B2 | 4/2021 | Swayze | |
| 2010/0267073 A1 | 10/2010 | Przedborski et al. | |
| 2015/0285822 A1 | 10/2015 | Zhang et al. | |
| 2017/0037410 A1 | 2/2017 | Swayze | |
| 2017/0087212 A1 | 3/2017 | Passini et al. | |
| 2017/0363643 A1 | 12/2017 | Rigo et al. | |
| 2019/0298708 A1* | 10/2019 | Jain | A61K 31/47 |
| 2020/0040342 A1 | 2/2020 | Swayze | |
| 2020/0239912 A1* | 7/2020 | Sah | C12N 15/113 |
| 2020/0354723 A1 | 11/2020 | Swayze | |
| 2021/0172963 A1* | 6/2021 | Benatar | G01N 33/6896 |
| 2022/0034907 A1 | 2/2022 | Ferguson | |

FOREIGN PATENT DOCUMENTS

| | | | |
|---|---|---|---|
| WO | WO2007002390 | 1/2007 | |
| WO | WO-2010129021 A1 * | 11/2010 | A61P 21/02 |
| WO | WO2014110291 | 7/2014 | |
| WO | WO2015153800 | 10/2015 | |
| WO | WO2015161170 | 10/2015 | |
| WO | WO2016040748 | 3/2016 | |
| WO | WO2019147960 | 8/2019 | |
| WO | WO2020061355 | 3/2020 | |
| WO | WO2020117772 | 6/2020 | |
| WO | WO2020123783 | 6/2020 | |
| WO | WO2020167715 | 8/2020 | |
| WO | WO2010148249 | 12/2020 | |

OTHER PUBLICATIONS

Bacioglu et al. Neuron 91, 56-66 (Year: 2016).*
Totzeck et al. Int. J, Mol. 20,5397, 1-10 (Year: 2019).*
Wurster et al. Therapeutic Advances in Neurological Disorders 2019, pp. 1-8 (Year: 2019).*
Wurster et al. Journal of Neurology 267:36-44 (Year: 2020).*
Yuan et al. Cold Spring Harbor Laboratory Press 9:a018309, pp. 1-24, Apr. 2017 (Year: 2017).*
Weston et al. Neurology 89:2167-2175, Nov. 21, 2017 (Year: 2017).*
Kiernan Nature Reviews Neurology, 10.1038, 186, pp. 1-2 (Year: 2018).*
Khalil et al. Nature Reviews Neurology 14, pp. 577-589 (Year: 2018).*
Byrne et al. Lancet vol. 16, pp. 601-609, published online Jun. 7, 2017 (Year: 2017).*
Spinraza (nusinersen) injection, for intrathecal use, FDA, Label Dec. 2016, pp. 1-13 (Year: 2016).*
Amor et al., "Neurofilament Light Antibodies in Semm Reflect Response to Natalizumab Treatment in Multiple Sclerosis", Multiple Sclerosis Journal, Sep. 2014, 20(10:1355-1362.
Benatar et al., "Neurofilament Light: A Candidate Biomarker of Presymptomatic Amyotrophic Lateral Sclerosis and Phenoconversion: Neurofilament Light in Presymptomatic ALS", Annals of Neurology, Jul. 2018, 84(1):130-139.
Calabresi et al., "Serum Neurofilament Light (NFL): Towards a Blood Test for Prognosis and Disease/Treatment Monitoring in Multiple Sclerosis Patients", Neurology, Apr. 2018, 90(15):Supp. 1.
Cifuentes-Diaz et al., "Neurofilament Accumulation at the Motor Endplate and Lack of Axonal Sprouting in a Spinal Muscular Atrophy Mouse Model", Human Molecular Genetics, Jun. 2002, 11(12): 1439-1447.

(Continued)

*Primary Examiner* — Brian Whiteman
(74) *Attorney, Agent, or Firm* — Fish & Richardson P.C.

(57) ABSTRACT

Featured are biomarkers for, e.g., diagnosis and prognosis of spinal muscular atrophy (SMA) as well as identification of responders to treatment of SMA. Also provided are methods of treating subjects with SMA.

22 Claims, 46 Drawing Sheets

Specification includes a Sequence Listing.

(56) References Cited

OTHER PUBLICATIONS

Costa et al., "Prognostic Value of Serum Neurofilaments Inpatients with Clinically Isolated Syndromes", Neurology, Jan. 2019, 92(7):e733-e741.

Costa et al., "Serum Neurofilament Light Chain Levels are Increased at the Onset of PML in Natalizumab Treated MS Patients" 70th Annual Meeting of the American Academy of Neurology, Apr. 2018, 1 page.

Costa et al., "Serum Neurofilament Light Chain Levels are Increased at the Onset of PML in Natalizumab-treated MS Patients", 4th Congress of the European-Academy-of-Neurology, Jun. 2018, p. 327.

Disanto et al., "Serum Neurofilament Light: A Biomarker of Neuronal Damage in Multiple Sclerosis: Serum NFL as a Biomarker in MS", Annals of Neurology, Jun. 2017, 81(6):857-870.

Fitzner et al., "Molecular Biomarkers in Cerebrospinal Fluid of Multiple Sclerosis Patients", Autoimmunity Reviews, Oct. 2015, 14(10):903-913.

Gunnarson et al., "Axonal Damage in Relapsing Multiple Sclerosis is Markedly Reduced by Natalizumab", Annals of Neurology, Jan. 2011, 69(1):83-89.

Kuhle et al., Neurofilament Light and Heavy Subunits Compared as Therapeutic Biomarkers in Multiple Sclerosis, ACTA Neurologica Scandinavica, Dec. 2013, 128(6):E33-E36.

Linker et al., "Innovative Monoclonal Antibody Therapies in Multiple Sclerosis", Therapeutic Advances in Neurological Disorders, Jul. 2008, 1(1):33-42.

Novakova et al., "Monitoring Disease Activity in Multiple Sclerosis using Serum Neurofilament Light Protein", Neurology, Nov. 2017, 89(22):2230-2237.

Novakova et al., "Reduced Cerebrospinal Fluid Concentrations of Oxysterols in Response to Natalizumab Treatment of Relapsing Remitting Multiple Sclerosis", Journal of Neurological Sciences, Aug. 2015, 358(1):201-206.

PCT International Preliminary Report on Patentability in International Appln. No. PCT/US2019/015185, dated Aug. 6, 2020, 8 pages.

PCT International Search Report and Written Opinion in International Appln. No. PCT/US2019/015185, dated Apr. 10, 2019, 16 pages.

PCT International Search Report and Written Opinion in International Appln. No. PCT/US2019/051992, dated Jun. 24, 2020, 21 pages.

PCT International Search Report and Written Opinion in International Appln. No. PCT/US2019/064190, dated Mar. 4, 2020, 16 pages.

PCT International Search Report and Written Opinion in International Appln. No. PCT/US2020/017600, dated May 26, 2020, 15 pages.

Rosengren et al., "Patients with Amyotrophic Lateral Sclerosis and Other Neurodegenerative Diseases have Increased Levels of Neurofilament Protein in CSF", Journal of Neurochemistry, Nov. 1996, 67(5): 2013-2018.

Rossi et al., "CSF Neurofilament Proteins as Diagnostic and Prognostic Biomarkers for Amyotrophic Lateral Sclerosis", Journal of Neurology—Zeitschrift Fuer Neurologic, Jan. 2018, 265(3):510-521.

Boido et al., "Neuromuscular Junctions as Key Contributors and Therapeutic Targets in Spinal Muscular Atrophy," Front Neuroanat, Feb. 3, 2016, 10(6):1-10.

Chiriboga et al., "Nusinersen for the Treatment of Spinal Muscular Atrophy," Expert Rev Neurother, Sep. 8, 2017, 17(10):955-962.

Lu et al., "Neurofilament Light Chain: A Prognostic Biomarker in Amyotrophic Lateral Sclerosis", American Academy of Neurology, 2015, 84:2247-2257.

Lu et al., "Plasma Neurofilament Heavy Chain Levels Correlate to Markers of Late State Disease Progression and Treatment Response in SOD1G93A Mice that Model ALS", PLoS One, Jul. 2012, 7(7):e40998.

McCampbell et al.., "Antisense Oligonucleotides Extend Survival and Reverse Decrement in Muscle Response in ALS Models", The Journal of Clinical Investigation, 2018, 128(8):3558-3567.

PCT International Preliminary Report on Patentability in International Appln. No. PCT/US2019/051992, dated Apr. 1, 2021, 12 pages.

PCT International Preliminary Report on Patentability in International Appln. No. PCT/US2020/017600, dated Aug. 26, 2021, 8 pages.

Puentes et al., "Immune Reactivity to Neurofilament Proteins in the Clinical Staging of Amytrophic Lateral Sclerosis", Journal Neurol. Neurosurg. Psychiatry, Sep. 2013, pp. 1-5.

* cited by examiner

Summary of baseline Characteristics and SMA History by baseline pNF-H concentrations (pg/ml) quartiles
Page 1 of 3

| | Quartiles of Baseline pNf-H | | | |
|---|---|---|---|---|
| | 1st Quartile (2390 - 10900) | 2nd Quartile (10900 - 15400) | 3rd Quartile (15400 - 21600) | 4th Quartile (21600 - 50100) |
| Number of subjects | 29 | 29 | 29 | 30 |
| Female sex n (%) | 19 (66%) | 13 (45%) | 16 (55%) | 17 (57%) |
| Age at first dose (Days) mean (min,max) | 181.4 (77, 262) | 179.4 (52, 237) | 154.2 (30, 235) | 161.9 (81, 235) |
| Age of symptom onset at baseline (weeks) mean (min,max) | 9.8 (4, 20) | 9.1 (3, 18) | 6.8 (3, 12) | 7.8 (2, 19) |
| Age at SMA diagnosis (weeks) mean (min,max) | 16.93 (5, 29) | 15.10 (4, 26) | 11.24 (0, 25) | 13.33 (2, 30) |
| Disease duration at screening (weeks) mean (min,max) | 13.4 (5, 21.1) | 14.1 (5, 21.1) | 13.1 (0, 22) | 13.3 (0, 23.1) |

Note: (a) Number of subjects in the table refers to subjects who have non-missing baseline value in each quartile
(b) SD=Standard Deviation
SOURCE: ISIS399443/BIOMARKER/CS3B-ADHOC/T-SUM-BASCHAR-SMA-PNFHQUART.SAS   DATE: 09NOV2017

FIG. 6

Summary of baseline Characteristics and SMA History by baseline
pNF-H concentrations (pg/ml) quartiles
Page 2 of 3

|  | Quartiles of Baseline pNf-H | | | |
| --- | --- | --- | --- | --- |
|  | 1st Quartile (2390 - 10900) | 2nd Quartile (10900 - 15400) | 3rd Quartile (15400 - 21600) | 4th Quartile (21600 - 50100) |
| Symptoms of SMA | | | | |
| Hyptonia | 29 (100%) | 29 (100%) | 29 (100%) | 30 (100%) |
| Dev Delay of Motor Funtion | 28 (97%) | 28 (97%) | 24 (83%) | 26 (87%) |
| Paradoxical Breathing | 23 (79%) | 23 (79%) | 24 (83%) | 25 (83%) |
| Pneumonia/Resp. Symptoms | 8 (28%) | 10 (34%) | 12 (41%) | 6 (20%) |
| Limb weakness | 29 (100%) | 29 (100%) | 29 (100%) | 29 (97%) |
| Swallowing Abnormalities | 15 (52%) | 11 (38%) | 14 (48%) | 12 (40%) |
| Other | 8 (28%) | 4 (14%) | 9 (31%) | 13 (43%) |
| Use of ventilator support n (%) | 7 (24%) | 7 (24%) | 8 (28%) | 5 (17%) |

Note: (a) Number of subjects in the table refers to subjects who have non-missing baseline value in each quartile (b) SD=Standard Deviation
SOURCE: ISIS396443/BIOMARKER/CS3B-ADHOC/T-SUM-BASCHAR-SMA-PNFHQUART.SAS
DATE: 09NOV2017

FIG. 7

Summary of baseline Characteristics and SMA History by baseline
pNF-H concentrations (pg/ml) quartiles
Page 3 of 3

|  | Quartiles of Baseline pNf-H | | | |
| --- | --- | --- | --- | --- |
|  | 1st Quartile (2390 - 10900) | 2nd Quartile (10900 - 15400) | 3rd Quartile (15400 - 21600) | 4th Quartile (21600 - 50100) |
| Total HINE-2 score mean +/- SD (b) | 1.7 +/- 1.41 | 1.4 +/- 1.18 | 1.0 +/- 0.85 | 1.4 +/- 1.00 |
| CHOP INTEND score mean +/- SD | 30.90 +/- 6.607 | 28.09 +/- 7.456 | 24.36 +/- 7.295 | 25.83 +/- 8.412 |
| Peroneal mean +/- SD | 0.39 +/- 0.311 | 0.41 +/- 0.348 | 0.27 +/- 0.199 | 0.29 +/- 0.283 |
| Ulnar mean +/- SD | 0.24 +/- 0.150 | 0.19 +/- 0.171 | 0.29 +/- 0.202 | 0.17 +/- 0.089 |

Note: (a) Number of subjects in the table refers to subjects who have non-missing baseline value in each quartile (b) SD=Standard Deviation
SOURCE: ISIS396443/BIOMARKER/CS3B-ADHOC/T-SUM-BASCHAR-SMA-PNFHQUART.SAS
DATE: 09NOV2017

FIG. 8

Variables in the initial model:

- Baseline log(pNF-H)
- Treatment group
- Disease duration (weeks)
- Sex
- Age of first dose (days)
- Age of SMA symptom onset (weeks)
- Age of SMA diagnosis (weeks)
- Gestational age (weeks)
- Baseline weight (kg)
- (Gestational age + age of first dose [weeks]) x (Gestational age + age of SMA symptom onset [weeks])
- Gestational age + age of SMA diagnosis (weeks)

| Variables in the Final Model | P-value |
|---|---|
| Intercept | <0.0001 |
| Baseline log(pNF-H) | 0.0062 |
| Age of SMA diagnosis (weeks) | 0.0016 |
| Baseline weight (kg) | 0.0075 |

FIG. 10

Variables in the initial model:

- Day 64 log(pNF-H)
- Treatment group
- Disease duration (weeks)
- Sex
- Age of first dose (days)
- Age of SMA symptom onset (weeks)
- Age of SMA diagnosis (weeks)
- Gestational age (weeks)
- Baseline weight (kg)
- (Gestational age + age of first dose [weeks]) x (Gestational age + age of SMA symptom onset [weeks])
- Gestational age + age of SMA diagnosis (weeks)

| Variables in the Final Model | P-value |
|---|---|
| Intercept | <0.0001 |
| Day 64 log(pNF-H) | <0.0001 |
| Disease duration | 0.0029 |

FIG. 17

Variables in the initial model:

- Day 64 log(pNF-H)
- Treatment group
- Disease duration (weeks)
- Sex
- Age of first dose (days)
- Age of SMA symptom onset (weeks)
- Age of SMA diagnosis (weeks)
- Gestational age (weeks)
- Baseline weight (kg)
- (Gestational age + age of first dose [weeks]) x (Gestational age + age of SMA symptom onset [weeks])
- Gestational age + age of SMA diagnosis (weeks)

| Variables in the Final Model | P-value |
|---|---|
| Intercept | <0.0001 |
| Day 64 log(pNF-H) | 0.0001 |
| Treatment group: nusinersen | 0.0050 |
| Disease duration | 0.0003 |

FIG. 19

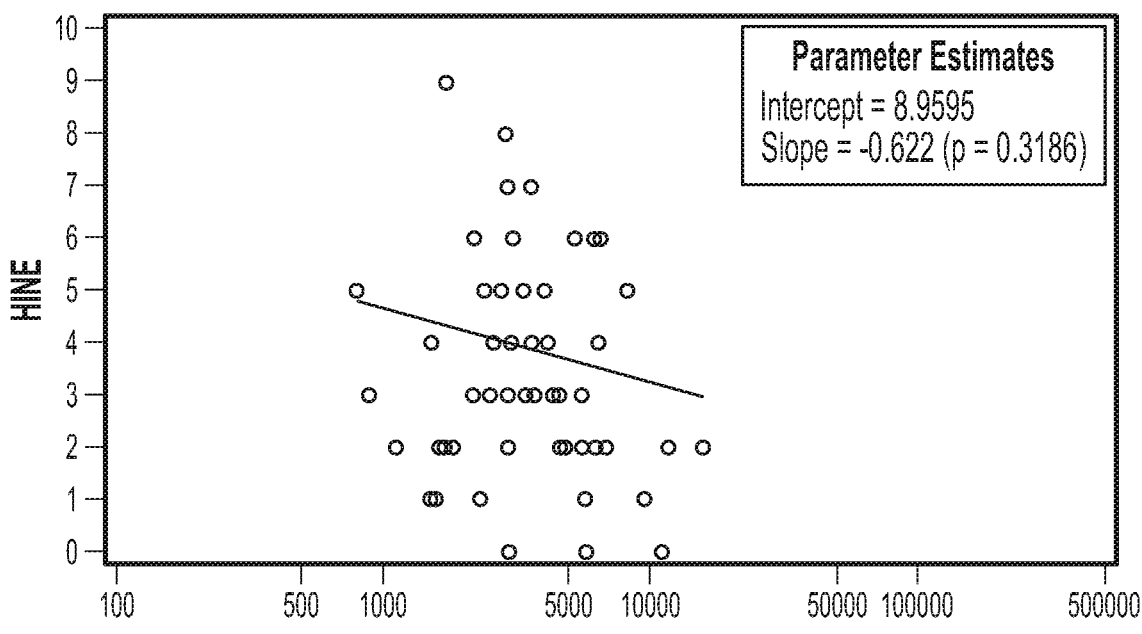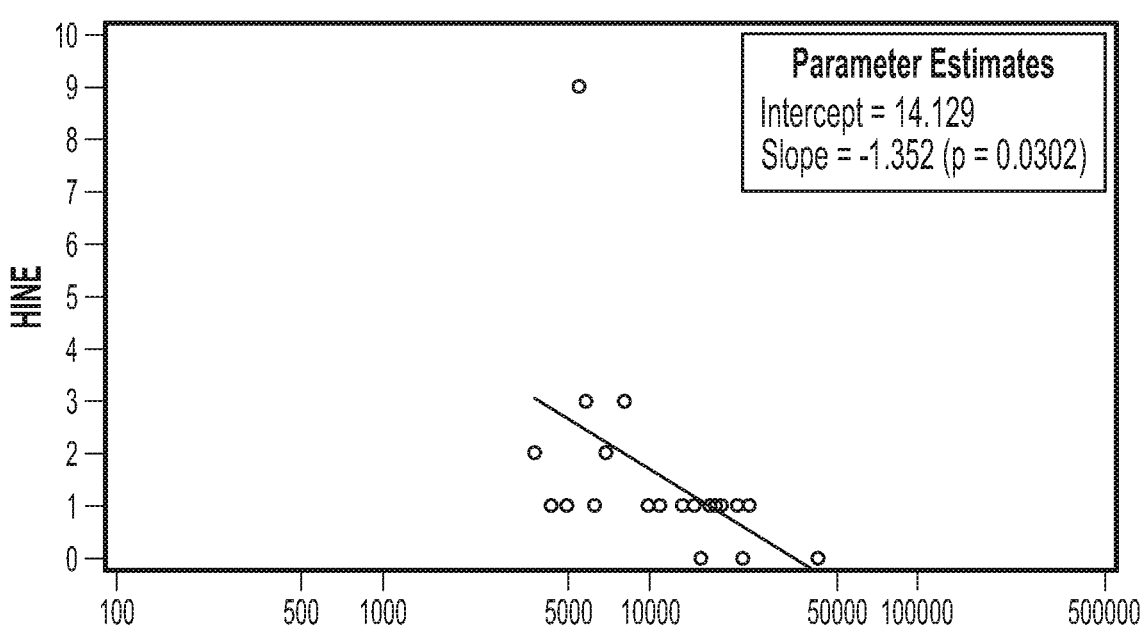
FIG. 28

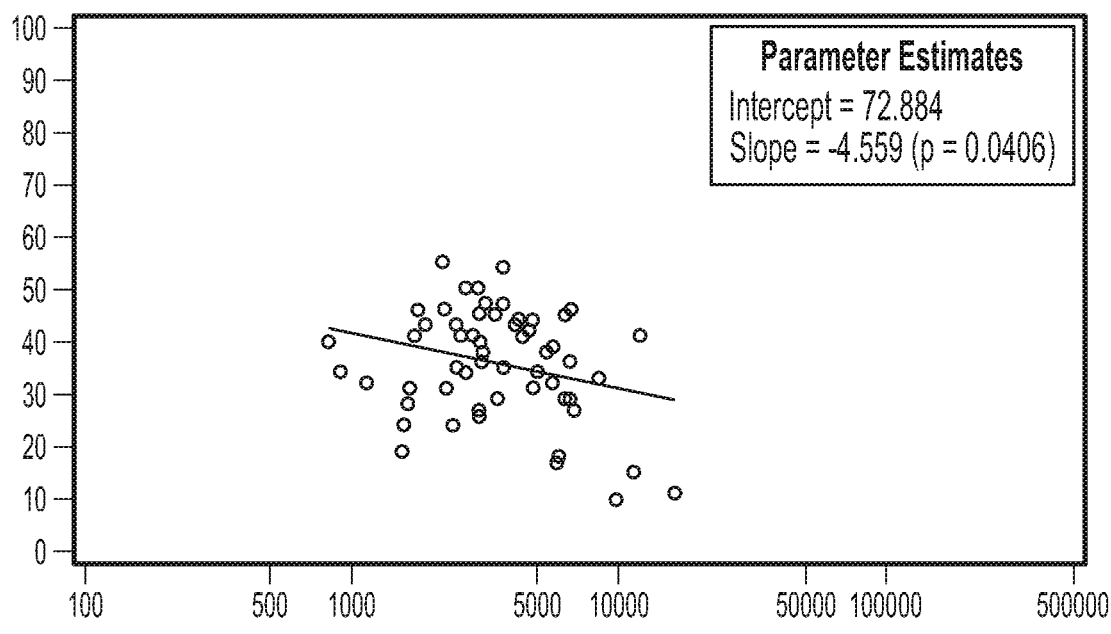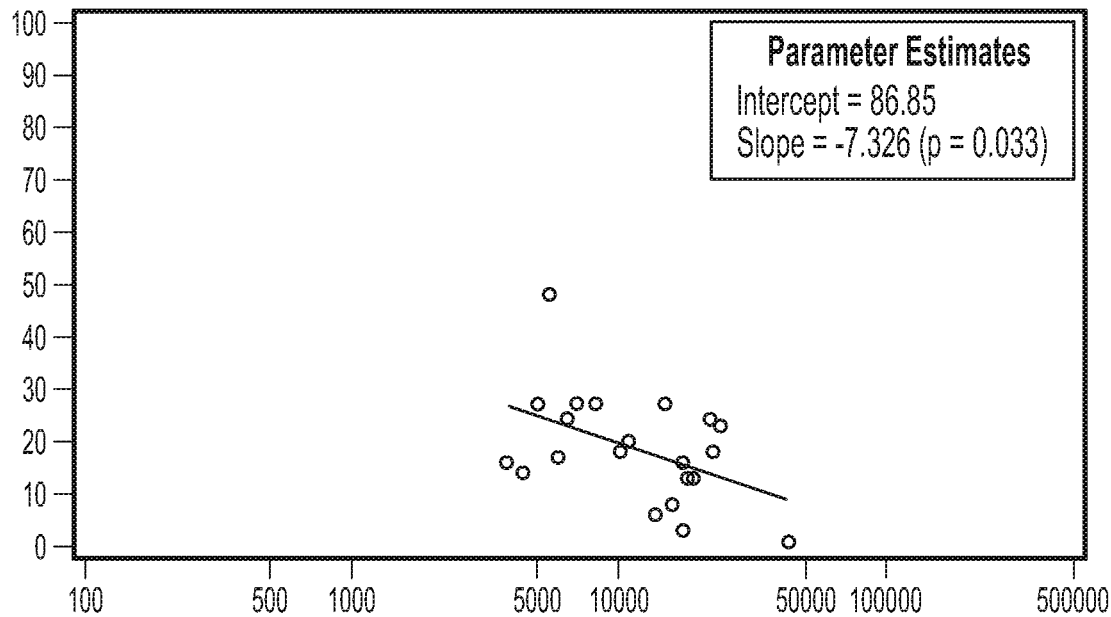
FIG. 29

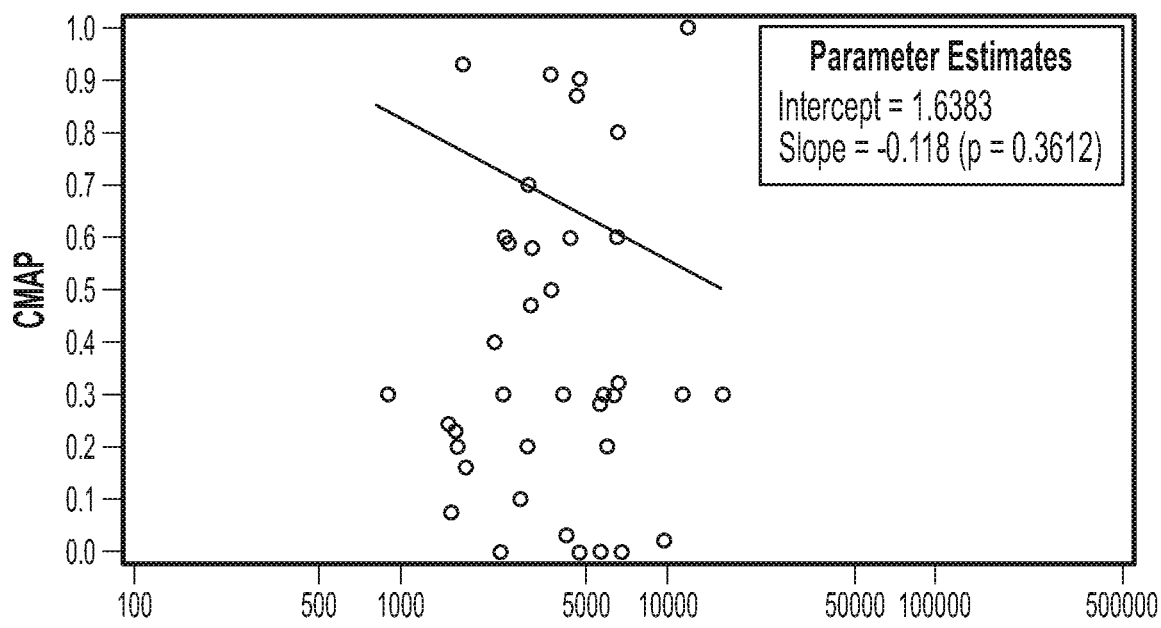
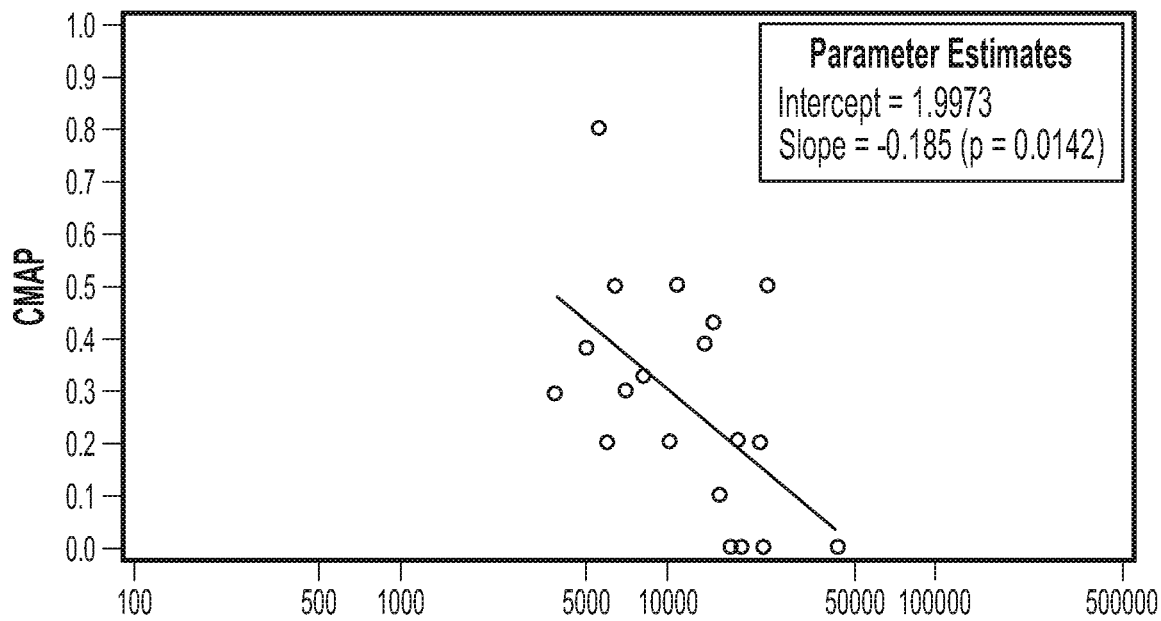
FIG. 33

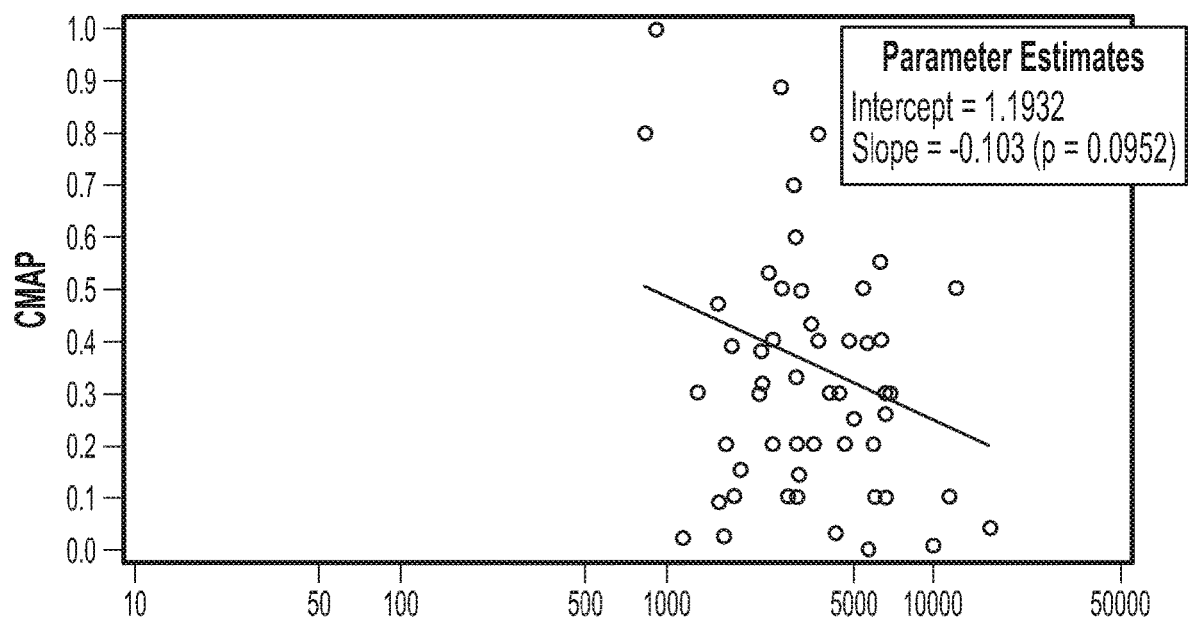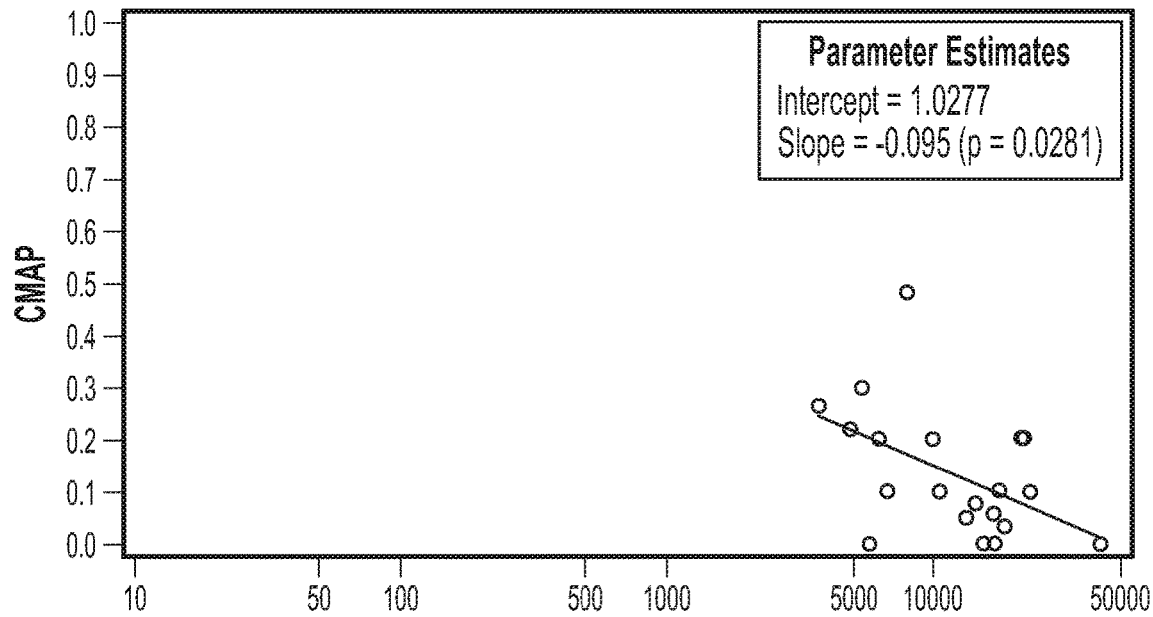
FIG. 35

SEQUENCE LISTING

```
<160> NUMBER OF SEQ ID NOS: 8

<210> SEQ ID NO 1
<211> LENGTH: 1026
<212> TYPE: PRT
<213> ORGANISM: Homo sapiens

<400> SEQUENCE: 1

Met Met Ser Phe Gly Gly Ala Asp Ala Leu Leu Gly Ala Pro Phe Ala
1               5                   10                  15

Pro Leu His Gly Gly Gly Ser Leu His Tyr Ala Leu Ala Arg Lys Gly
            20                  25                  30

Gly Ala Gly Gly Thr Arg Ser Ala Ala Gly Ser Ser Ser Gly Phe His
        35                  40                  45

Ser Trp Thr Arg Thr Ser Val Ser Ser Val Ser Ala Ser Pro Ser Arg
    50                  55                  60

Phe Arg Gly Ala Gly Ala Ala Ser Ser Thr Asp Ser Leu Asp Thr Leu
65                  70                  75                  80

Ser Asn Gly Pro Glu Gly Cys Met Val Ala Val Ala Thr Ser Arg Ser
                85                  90                  95

Glu Lys Glu Gln Leu Gln Ala Leu Asn Asp Arg Phe Ala Gly Tyr Ile
            100                 105                 110

Asp Lys Val Arg Gln Leu Glu Ala His Asn Arg Ser Leu Glu Gly Glu
        115                 120                 125

Ala Ala Ala Leu Arg Gln Gln Gln Ala Gly Arg Ser Ala Met Gly Glu
    130                 135                 140

Leu Tyr Glu Arg Glu Val Arg Glu Met Arg Gly Ala Val Leu Arg Leu
145                 150                 155                 160

Gly Ala Ala Arg Gly Gln Leu Arg Leu Glu Gln Glu His Leu Leu Glu
                165                 170                 175

Asp Ile Ala His Val Arg Gln Arg Leu Asp Asp Glu Ala Arg Gln Arg
            180                 185                 190
```

-continued

Glu Glu Ala Glu Ala Ala Arg Ala Leu Ala Arg Phe Ala Gln Glu
            195                 200                 205

Ala Glu Ala Ala Arg Val Asp Leu Gln Lys Lys Ala Gln Ala Leu Gln
    210                 215                 220

Glu Glu Cys Gly Tyr Leu Arg Arg His His Gln Glu Val Gly Glu
225                 230                 235                 240

Leu Leu Gly Gln Ile Gln Gly Ser Gly Ala Gln Ala Gln Met Gln
                245                 250                 255

Ala Glu Thr Arg Asp Ala Leu Lys Cys Asp Val Thr Ser Ala Leu Arg
        260                 265                 270

Glu Ile Arg Ala Gln Leu Glu Gly His Ala Val Gln Ser Thr Leu Gln
        275                 280                 285

Ser Glu Glu Trp Phe Arg Val Arg Leu Asp Arg Leu Ser Glu Ala Ala
    290                 295                 300

Lys Val Asn Thr Asp Ala Met Arg Ser Ala Gln Glu Glu Ile Thr Glu
305                 310                 315                 320

Tyr Arg Arg Gln Leu Gln Ala Arg Thr Thr Glu Leu Glu Ala Leu Lys
                325                 330                 335

Ser Thr Lys Asp Ser Leu Glu Arg Gln Arg Ser Glu Leu Glu Asp Arg
            340                 345                 350

His Gln Ala Asp Ile Ala Ser Tyr Gln Glu Ala Ile Gln Gln Leu Asp
        355                 360                 365

Ala Glu Leu Arg Asn Thr Lys Trp Glu Met Ala Ala Gln Leu Arg Glu
    370                 375                 380

Tyr Gln Asp Leu Leu Asn Val Lys Met Ala Leu Asp Ile Glu Ile Ala
385                 390                 395                 400

Ala Tyr Arg Lys Leu Leu Glu Gly Glu Glu Cys Arg Ile Gly Phe Gly
                405                 410                 415

Pro Ile Pro Phe Ser Leu Pro Glu Gly Leu Pro Lys Ile Pro Ser Val
            420                 425                 430

Ser Thr His Ile Lys Val Lys Ser Glu Glu Lys Ile Lys Val Val Glu
        435                 440                 445

Lys Ser Glu Lys Glu Thr Val Ile Val Glu Glu Gln Thr Glu Glu Thr
    450                 455                 460

Gln Val Thr Glu Glu Val Thr Glu Glu Glu Lys Glu Ala Lys Glu
465                 470                 475                 480

Glu Glu Gly Lys Glu Glu Gly Glu Glu Glu Ala Glu Gly
                485                 490                 495

Gly Glu Glu Glu Thr Lys Ser Pro Pro Ala Glu Glu Ala Ala Ser Pro
            500                 505                 510

Glu Lys Glu Ala Lys Ser Pro Val Lys Glu Glu Ala Lys Ser Pro Ala
        515                 520                 525

Glu Ala Lys Ser Pro Glu Lys Glu Glu Ala Lys Ser Pro Ala Glu Val
    530                 535                 540

Lys Ser Pro Glu Lys Ala Lys Ser Pro Ala Lys Glu Glu Ala Lys Ser
545                 550                 555                 560

Pro Pro Glu Ala Lys Ser Pro Glu Lys Glu Glu Ala Lys Ser Pro Ala
                565                 570                 575

Glu Val Lys Ser Pro Glu Lys Ala Lys Ser Pro Ala Lys Glu Glu Ala
            580                 585                 590

Lys Ser Pro Ala Glu Ala Lys Ser Pro Glu Lys Ala Lys Ser Pro Val
        595                 600                 605

Lys Glu Glu Ala Lys Ser Pro Ala Glu Ala Lys Ser Pro Val Lys Glu

```
          610                 615                 620
Glu Ala Lys Ser Pro Ala Val Lys Ser Pro Lys Ala Lys Ser
625                 630                 635                 640

Pro Thr Lys Glu Glu Ala Lys Ser Pro Glu Lys Ala Lys Ser Pro Glu
                    645                 650                 655

Lys Ala Lys Ser Pro Glu Lys Glu Glu Ala Lys Ser Pro Glu Lys Ala
                    660                 665                 670

Lys Ser Pro Val Lys Ala Glu Ala Lys Ser Pro Glu Lys Ala Lys Ser
                    675                 680                 685

Pro Val Lys Ala Glu Ala Lys Ser Pro Glu Lys Ala Lys Ser Pro Val
                    690                 695                 700

Lys Glu Glu Ala Lys Ser Pro Glu Lys Ala Lys Ser Pro Val Lys Glu
705                 710                 715                 720

Glu Ala Lys Ser Pro Glu Lys Ala Lys Ser Pro Val Lys Glu Glu Ala
                    725                 730                 735

Lys Thr Pro Glu Lys Ala Lys Ser Pro Val Lys Glu Glu Ala Lys Ser
                    740                 745                 750

Pro Glu Lys Ala Lys Ser Pro Glu Lys Ala Lys Thr Leu Asp Val Lys
                    755                 760                 765

Ser Pro Glu Ala Lys Thr Pro Ala Lys Glu Glu Ala Arg Ser Pro Ala
770                 775                 780

Asp Lys Phe Pro Glu Lys Ala Lys Ser Pro Val Lys Glu Glu Val Lys
785                 790                 795                 800

Ser Pro Glu Lys Ala Lys Ser Pro Leu Lys Glu Asp Ala Lys Ala Pro
                    805                 810                 815

Glu Lys Glu Ile Pro Lys Lys Glu Glu Val Lys Ser Pro Val Lys Glu
                    820                 825                 830

Glu Glu Lys Pro Gln Glu Val Lys Val Lys Glu Pro Pro Lys Lys Ala
                    835                 840                 845

Glu Glu Glu Lys Ala Pro Ala Thr Pro Lys Thr Glu Glu Lys Lys Asp
                    850                 855                 860

Ser Lys Lys Glu Glu Ala Pro Lys Lys Glu Ala Pro Lys Pro Lys Val
865                 870                 875                 880

Glu Glu Lys Lys Glu Pro Ala Val Glu Lys Pro Lys Glu Ser Lys Val
                    885                 890                 895

Glu Ala Lys Lys Glu Glu Ala Glu Asp Lys Lys Val Pro Thr Pro
                    900                 905                 910

Glu Lys Glu Ala Pro Ala Lys Val Glu Val Lys Glu Asp Ala Lys Pro
                    915                 920                 925

Lys Glu Lys Thr Glu Val Ala Lys Lys Glu Pro Asp Asp Ala Lys Ala
930                 935                 940

Lys Glu Pro Ser Lys Pro Ala Glu Lys Lys Lys Ala Ala Pro Glu Lys
945                 950                 955                 960

Lys Asp Thr Lys Glu Glu Lys Ala Lys Lys Pro Glu Glu Lys Pro Lys
                    965                 970                 975

Thr Glu Ala Lys Ala Lys Glu Asp Asp Lys Thr Leu Ser Lys Glu Pro
                    980                 985                 990

Ser Lys Pro Lys Ala Glu Lys Ala Glu Lys Ser Ser Ser Thr Asp Gln
                    995                1000                1005

Lys Asp Ser Lys Pro Pro Glu Lys Ala Thr Glu Asp Lys Ala Ala
                    1010                1015                1020

Lys Gly Lys
                    1025
```

<210> SEQ ID NO 2
<211> LENGTH: 543
<212> TYPE: PRT
<213> ORGANISM: Homo sapiens

<400> SEQUENCE: 2

```
Met Ser Ser Phe Ser Tyr Glu Pro Tyr Tyr Ser Thr Ser Tyr Lys Arg
1               5                   10                  15

Arg Tyr Val Glu Thr Pro Arg Val His Ile Ser Ser Val Arg Ser Gly
                20                  25                  30

Tyr Ser Thr Ala Arg Ser Ala Tyr Ser Ser Tyr Ser Ala Pro Val Ser
            35                  40                  45

Ser Ser Leu Ser Val Arg Arg Ser Tyr Ser Ser Ser Gly Ser Leu
        50                  55                  60

Met Pro Ser Leu Glu Asn Leu Asp Leu Ser Gln Val Ala Ala Ile Ser
65                  70                  75                  80

Asn Asp Leu Lys Ser Ile Arg Thr Gln Glu Lys Ala Gln Leu Gln Asp
                85                  90                  95

Leu Asn Asp Arg Phe Ala Ser Phe Ile Glu Arg Val His Glu Leu Glu
                100                 105                 110

Gln Gln Asn Lys Val Leu Glu Ala Glu Leu Leu Val Leu Arg Gln Lys
            115                 120                 125

His Ser Glu Pro Ser Arg Phe Arg Ala Leu Tyr Glu Gln Glu Ile Arg
        130                 135                 140

Asp Leu Arg Leu Ala Ala Glu Asp Ala Thr Asn Glu Lys Gln Ala Leu
145                 150                 155                 160

Gln Gly Glu Arg Glu Gly Leu Glu Glu Thr Leu Arg Asn Leu Gln Ala
                165                 170                 175

Arg Tyr Glu Glu Glu Val Leu Ser Arg Glu Asp Ala Glu Gly Arg Leu
                180                 185                 190

Met Glu Ala Arg Lys Gly Ala Asp Glu Ala Ala Leu Ala Arg Ala Glu
            195                 200                 205

Leu Glu Lys Arg Ile Asp Ser Leu Met Asp Glu Ile Ser Phe Leu Lys
        210                 215                 220

Lys Val His Glu Glu Glu Ile Ala Glu Leu Gln Ala Gln Ile Gln Tyr
225                 230                 235                 240

Ala Gln Ile Ser Val Glu Met Asp Val Thr Lys Pro Asp Leu Ser Ala
                245                 250                 255

Ala Leu Lys Asp Ile Arg Ala Gln Tyr Glu Lys Leu Ala Ala Lys Asn
                260                 265                 270

Met Gln Asn Ala Glu Glu Trp Phe Lys Ser Arg Phe Thr Val Leu Thr
            275                 280                 285

Glu Ser Ala Ala Lys Asn Thr Asp Ala Val Arg Ala Ala Lys Asp Glu
        290                 295                 300

Val Ser Glu Ser Arg Arg Leu Leu Lys Ala Lys Thr Leu Glu Ile Glu
305                 310                 315                 320

Ala Cys Arg Gly Met Asn Glu Ala Leu Glu Lys Gln Leu Gln Glu Leu
                325                 330                 335

Glu Asp Lys Gln Asn Ala Asp Ile Ser Ala Met Gln Asp Thr Ile Asn
                340                 345                 350

Lys Leu Glu Asn Glu Leu Arg Thr Thr Lys Ser Glu Met Ala Arg Tyr
            355                 360                 365

Leu Lys Glu Tyr Gln Asp Leu Leu Asn Val Lys Met Ala Leu Asp Ile
```

```
            370                 375                 380
Glu Ile Ala Ala Tyr Arg Lys Leu Leu Glu Gly Glu Thr Arg Leu
385                 390                 395                 400

Ser Phe Thr Ser Val Gly Ser Ile Thr Ser Gly Tyr Ser Gln Ser Ser
                    405                 410                 415

Gln Val Phe Gly Arg Ser Ala Tyr Gly Gly Leu Gln Thr Ser Ser Tyr
                420                 425                 430

Leu Met Ser Thr Arg Ser Phe Pro Ser Tyr Tyr Thr Ser His Val Gln
                435                 440                 445

Glu Glu Gln Ile Glu Val Glu Glu Thr Ile Glu Ala Ala Lys Ala Glu
            450                 455                 460

Glu Ala Lys Asp Glu Pro Pro Ser Glu Gly Glu Ala Glu Glu Glu Glu
465                 470                 475                 480

Lys Asp Lys Glu Glu Ala Glu Glu Glu Ala Ala Glu Glu Glu Glu
                    485                 490                 495

Ala Ala Lys Glu Glu Ser Glu Glu Ala Lys Glu Glu Glu Glu Gly Gly
                500                 505                 510

Glu Gly Glu Glu Gly Glu Glu Thr Lys Glu Ala Glu Glu Glu Glu Lys
            515                 520                 525

Lys Val Glu Gly Ala Gly Glu Glu Gln Ala Ala Lys Lys Lys Asp
            530                 535                 540

<210> SEQ ID NO 3
<211> LENGTH: 916
<212> TYPE: PRT
<213> ORGANISM: Homo sapiens

<400> SEQUENCE: 3

Met Ser Tyr Thr Leu Asp Ser Leu Gly Asn Pro Ser Ala Tyr Arg Arg
1               5                   10                  15

Val Thr Glu Thr Arg Ser Ser Phe Ser Arg Val Ser Gly Ser Pro Ser
                20                  25                  30

Ser Gly Phe Arg Ser Gln Ser Trp Ser Arg Gly Ser Pro Ser Thr Val
            35                  40                  45

Ser Ser Ser Tyr Lys Arg Ser Met Leu Ala Pro Arg Leu Ala Tyr Ser
        50                  55                  60

Ser Ala Met Leu Ser Ser Ala Glu Ser Ser Leu Asp Phe Ser Gln Ser
65                  70                  75                  80

Ser Ser Leu Leu Asn Gly Gly Ser Gly Pro Gly Gly Asp Tyr Lys Leu
                85                  90                  95

Ser Arg Ser Asn Glu Lys Glu Gln Leu Gln Gly Leu Asn Asp Arg Phe
                100                 105                 110

Ala Gly Tyr Ile Glu Lys Val His Tyr Leu Glu Gln Gln Asn Lys Glu
            115                 120                 125

Ile Glu Ala Glu Ile Gln Ala Leu Arg Gln Lys Gln Ala Ser His Ala
130                 135                 140

Gln Leu Gly Asp Ala Tyr Asp Gln Glu Ile Arg Glu Leu Arg Ala Thr
145                 150                 155                 160

Leu Glu Met Val Asn His Glu Lys Ala Gln Val Gln Leu Asp Ser Asp
                165                 170                 175

His Leu Glu Glu Asp Ile His Arg Leu Lys Glu Arg Phe Glu Glu Glu
            180                 185                 190

Ala Arg Leu Arg Asp Asp Thr Glu Ala Ala Ile Arg Ala Leu Arg Lys
        195                 200                 205
```

-continued

```
Asp Ile Glu Glu Ala Ser Leu Val Lys Val Glu Leu Asp Lys Lys Val
210                 215                 220
Gln Ser Leu Gln Asp Glu Val Ala Phe Leu Arg Ser Asn His Glu Glu
225                 230                 235                 240
Glu Val Ala Asp Leu Leu Ala Gln Ile Gln Ala Ser His Ile Thr Val
                245                 250                 255
Glu Arg Lys Asp Tyr Leu Lys Thr Asp Ile Ser Thr Ala Leu Lys Glu
            260                 265                 270
Ile Arg Ser Gln Leu Glu Ser His Ser Asp Gln Asn Met His Gln Ala
        275                 280                 285
Glu Glu Trp Phe Lys Cys Arg Tyr Ala Lys Leu Thr Glu Ala Ala Glu
290                 295                 300
Gln Asn Lys Glu Ala Ile Arg Ser Ala Lys Glu Glu Ile Ala Glu Tyr
305                 310                 315                 320
Arg Arg Gln Leu Gln Ser Lys Ser Ile Glu Leu Glu Ser Val Arg Gly
                325                 330                 335
Thr Lys Glu Ser Leu Glu Arg Gln Leu Ser Asp Ile Glu Glu Arg His
            340                 345                 350
Asn His Asp Leu Ser Ser Tyr Gln Asp Thr Ile Gln Gln Leu Glu Asn
        355                 360                 365
Glu Leu Arg Gly Thr Lys Trp Glu Met Ala Arg His Leu Arg Glu Tyr
370                 375                 380
Gln Asp Leu Leu Asn Val Lys Met Ala Leu Asp Ile Glu Ile Ala Ala
385                 390                 395                 400
Tyr Arg Lys Leu Leu Glu Gly Glu Glu Thr Arg Phe Ser Thr Phe Ala
                405                 410                 415
Gly Ser Ile Thr Gly Pro Leu Tyr Thr His Arg Pro Pro Ile Thr Ile
            420                 425                 430
Ser Ser Lys Ile Gln Lys Pro Lys Val Glu Ala Pro Lys Leu Lys Val
        435                 440                 445
Gln His Lys Phe Val Glu Glu Ile Ile Glu Glu Thr Lys Val Glu Asp
450                 455                 460
Glu Lys Ser Glu Met Glu Glu Ala Leu Thr Ala Ile Thr Glu Glu Leu
465                 470                 475                 480
Ala Val Ser Met Lys Glu Glu Lys Glu Ala Ala Glu Glu Lys Glu
                485                 490                 495
Glu Glu Pro Glu Ala Glu Glu Glu Val Ala Ala Lys Lys Ser Pro
            500                 505                 510
Val Lys Ala Thr Ala Pro Glu Val Lys Glu Glu Glu Gly Glu Lys Glu
        515                 520                 525
Glu Glu Glu Gly Gln Glu Glu Glu Glu Asp Glu Gly Ala Lys
530                 535                 540
Ser Asp Gln Ala Glu Glu Gly Gly Ser Glu Lys Glu Gly Ser Ser Glu
545                 550                 555                 560
Lys Glu Glu Gly Glu Gln Glu Glu Gly Glu Thr Glu Ala Glu Ala Glu
                565                 570                 575
Gly Glu Glu Ala Glu Ala Lys Glu Glu Lys Lys Val Glu Glu Lys Ser
            580                 585                 590
Glu Glu Val Ala Thr Lys Glu Glu Leu Val Ala Asp Ala Lys Val Glu
        595                 600                 605
Lys Pro Glu Lys Ala Lys Ser Pro Val Pro Lys Ser Pro Val Glu Glu
610                 615                 620
Lys Gly Lys Ser Pro Val Pro Lys Ser Pro Val Glu Glu Lys Gly Lys
```

```
                625                 630                 635                 640
        Ser Pro Val Pro Lys Ser Pro Val Glu Glu Lys Gly Lys Ser Pro Val
                        645                 650                 655
        Pro Lys Ser Pro Val Glu Glu Lys Gly Lys Ser Pro Val Ser Lys Ser
                        660                 665                 670
        Pro Val Glu Glu Lys Ala Lys Ser Pro Val Pro Lys Ser Pro Val Glu
                        675                 680                 685
        Glu Ala Lys Ser Lys Ala Glu Val Gly Lys Gly Glu Gln Lys Glu Glu
                        690                 695                 700
        Glu Glu Lys Glu Val Lys Glu Ala Pro Lys Glu Lys Val Glu Lys
        705                 710                 715                 720
        Lys Glu Glu Lys Pro Lys Asp Val Pro Glu Lys Lys Ala Glu Ser
                        725                 730                 735
        Pro Val Lys Glu Glu Ala Val Ala Glu Val Val Thr Ile Thr Lys Ser
                        740                 745                 750
        Val Lys Val His Leu Glu Lys Glu Thr Lys Glu Glu Gly Lys Pro Leu
        755                 760                 765
        Gln Gln Glu Lys Glu Lys Glu Lys Ala Gly Gly Glu Gly Gly Ser Glu
                770                 775                 780
        Glu Glu Gly Ser Asp Lys Gly Ala Lys Gly Ser Arg Lys Glu Asp Ile
        785                 790                 795                 800
        Ala Val Asn Gly Glu Val Glu Gly Lys Glu Glu Val Glu Gln Glu Thr
                        805                 810                 815
        Lys Glu Lys Gly Ser Gly Arg Glu Glu Lys Gly Val Val Thr Asn
                        820                 825                 830
        Gly Leu Asp Leu Ser Pro Ala Asp Glu Lys Lys Gly Gly Asp Lys Ser
                835                 840                 845
        Glu Glu Lys Val Val Val Thr Lys Thr Val Glu Lys Ile Thr Ser Glu
                        850                 855                 860
        Gly Gly Asp Gly Ala Thr Lys Tyr Ile Thr Lys Ser Val Thr Val Thr
        865                 870                 875                 880
        Gln Lys Val Glu Glu His Glu Glu Thr Phe Glu Glu Lys Leu Val Ser
                        885                 890                 895
        Thr Lys Lys Val Glu Lys Val Thr Ser His Ala Ile Val Lys Glu Val
                        900                 905                 910
        Thr Gln Ser Asp
                915

<210> SEQ ID NO 4
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
tcactttcat aatgctgg                                                   18

<210> SEQ ID NO 5
<211> LENGTH: 1020
<212> TYPE: PRT
<213> ORGANISM: Homo sapiens

<400> SEQUENCE: 5

Met Met Ser Phe Gly Gly Ala Asp Ala Leu Leu Gly Ala Pro Phe Ala
```

-continued

```
1               5               10              15
Pro Leu His Gly Gly Gly Ser Leu His Tyr Ala Leu Ala Arg Lys Gly
                20                  25                  30
Gly Ala Gly Gly Thr Arg Ser Ala Gly Ser Ser Ser Gly Phe His
            35                  40                  45
Ser Trp Thr Arg Thr Ser Val Ser Val Ser Ala Ser Pro Ser Arg
    50                  55                  60
Phe Arg Gly Ala Gly Ala Ala Ser Ser Thr Asp Ser Leu Asp Thr Leu
65                  70                  75                  80
Ser Asn Gly Pro Glu Gly Cys Met Val Ala Val Ala Thr Ser Arg Ser
                85                  90                  95
Glu Lys Glu Gln Leu Gln Ala Leu Asn Asp Arg Phe Ala Gly Tyr Ile
                100                 105                 110
Asp Lys Val Arg Gln Leu Glu Ala His Asn Arg Ser Leu Glu Gly Glu
            115                 120                 125
Ala Ala Ala Leu Arg Gln Gln Gln Ala Gly Arg Ser Ala Met Gly Glu
        130                 135                 140
Leu Tyr Glu Arg Glu Val Arg Glu Met Arg Gly Ala Val Leu Arg Leu
145                 150                 155                 160
Gly Ala Ala Arg Gly Gln Leu Arg Leu Glu Gln Glu His Leu Leu Glu
                165                 170                 175
Asp Ile Ala His Val Arg Gln Arg Leu Asp Asp Glu Ala Arg Gln Arg
            180                 185                 190
Glu Glu Ala Glu Ala Ala Ala Arg Ala Leu Ala Arg Phe Ala Gln Glu
        195                 200                 205
Ala Glu Ala Ala Arg Val Asp Leu Gln Lys Lys Ala Gln Ala Leu Gln
210                 215                 220
Glu Glu Cys Gly Tyr Leu Arg Arg His His Gln Glu Glu Val Gly Glu
225                 230                 235                 240
Leu Leu Gly Gln Ile Gln Gly Ser Gly Ala Ala Gln Ala Gln Met Gln
                245                 250                 255
Ala Glu Thr Arg Asp Ala Leu Lys Cys Asp Val Thr Ser Ala Leu Arg
            260                 265                 270
Glu Ile Arg Ala Gln Leu Glu Gly His Ala Val Gln Ser Thr Leu Gln
        275                 280                 285
Ser Glu Glu Trp Phe Arg Val Arg Leu Asp Arg Leu Ser Glu Ala Ala
        290                 295                 300
Lys Val Asn Thr Asp Ala Met Arg Ser Ala Gln Glu Glu Ile Thr Glu
305                 310                 315                 320
Tyr Arg Arg Gln Leu Gln Ala Arg Thr Thr Glu Leu Glu Ala Leu Lys
                325                 330                 335
Ser Thr Lys Asp Ser Leu Glu Arg Gln Arg Ser Glu Leu Glu Asp Arg
            340                 345                 350
His Gln Ala Asp Ile Ala Ser Tyr Gln Glu Ala Ile Gln Gln Leu Asp
        355                 360                 365
Ala Glu Leu Arg Asn Thr Lys Trp Glu Met Ala Ala Gln Leu Arg Glu
        370                 375                 380
Tyr Gln Asp Leu Leu Asn Val Lys Met Ala Leu Asp Ile Glu Ile Ala
385                 390                 395                 400
Ala Tyr Arg Lys Leu Leu Glu Gly Glu Glu Cys Arg Ile Gly Phe Gly
                405                 410                 415
Pro Ile Pro Phe Ser Leu Pro Glu Gly Leu Pro Lys Ile Pro Ser Val
            420                 425                 430
```

```
Ser Thr His Ile Lys Val Lys Ser Glu Glu Lys Ile Lys Val Val Glu
        435                 440                 445
Lys Ser Glu Lys Glu Thr Val Ile Val Glu Glu Gln Thr Glu Glu Thr
    450                 455                 460
Gln Val Thr Glu Glu Val Thr Glu Glu Glu Lys Glu Ala Lys Glu
465                 470                 475                 480
Glu Glu Gly Lys Glu Glu Gly Gly Glu Glu Glu Ala Glu Gly
                    485                 490                 495
Gly Glu Glu Glu Thr Lys Ser Pro Pro Ala Glu Glu Ala Ala Ser Pro
                500                 505                 510
Glu Lys Glu Ala Lys Ser Pro Val Lys Glu Glu Ala Lys Ser Pro Ala
            515                 520                 525
Glu Ala Lys Ser Pro Glu Lys Glu Ala Lys Ser Pro Ala Glu Val
        530                 535                 540
Lys Ser Pro Glu Lys Ala Lys Ser Pro Ala Lys Glu Ala Lys Ser
545                 550                 555                 560
Pro Pro Glu Ala Lys Ser Pro Glu Lys Glu Ala Lys Ser Pro Ala
                565                 570                 575
Glu Val Lys Ser Pro Glu Lys Ala Lys Ser Pro Ala Lys Glu Glu Ala
            580                 585                 590
Lys Ser Pro Ala Glu Ala Lys Ser Pro Glu Lys Ala Lys Ser Pro Val
        595                 600                 605
Lys Glu Glu Ala Lys Ser Pro Ala Glu Ala Lys Ser Pro Val Lys Glu
    610                 615                 620
Glu Ala Lys Ser Pro Ala Glu Val Lys Ser Pro Glu Lys Ala Lys Ser
625                 630                 635                 640
Pro Thr Lys Glu Glu Ala Lys Ser Pro Glu Lys Ala Lys Ser Pro Glu
                645                 650                 655
Lys Glu Glu Ala Lys Ser Pro Glu Lys Ala Lys Ser Pro Val Lys Ala
            660                 665                 670
Glu Ala Lys Ser Pro Glu Lys Ala Lys Ser Pro Val Lys Ala Glu Ala
        675                 680                 685
Lys Ser Pro Glu Lys Ala Lys Ser Pro Val Lys Glu Glu Ala Lys Ser
    690                 695                 700
Pro Glu Lys Ala Lys Ser Pro Val Lys Glu Glu Ala Lys Ser Pro Glu
705                 710                 715                 720
Lys Ala Lys Ser Pro Val Lys Glu Glu Ala Lys Thr Pro Glu Lys Ala
                725                 730                 735
Lys Ser Pro Val Lys Glu Glu Ala Lys Ser Pro Glu Lys Ala Lys Ser
            740                 745                 750
Pro Glu Lys Ala Lys Thr Leu Asp Val Lys Ser Pro Glu Ala Lys Thr
        755                 760                 765
Pro Ala Lys Glu Glu Ala Arg Ser Pro Ala Asp Lys Phe Pro Glu Lys
    770                 775                 780
Ala Lys Ser Pro Val Lys Glu Glu Val Lys Ser Pro Glu Lys Ala Lys
785                 790                 795                 800
Ser Pro Leu Lys Glu Asp Ala Lys Ala Pro Glu Lys Glu Ile Pro Lys
                805                 810                 815
Lys Glu Glu Val Lys Ser Pro Val Lys Glu Glu Lys Pro Gln Glu
            820                 825                 830
Val Lys Val Lys Glu Pro Pro Lys Lys Ala Glu Glu Lys Ala Pro
        835                 840                 845
```

```
Ala Thr Pro Lys Thr Glu Glu Lys Asp Ser Lys Lys Glu Glu Ala
850                 855                 860

Pro Lys Lys Glu Ala Pro Lys Pro Lys Val Glu Glu Lys Lys Glu Pro
865                 870                 875                 880

Ala Val Glu Lys Pro Lys Glu Ser Lys Val Glu Ala Lys Lys Glu
                885                 890                 895

Ala Glu Asp Lys Lys Val Pro Thr Pro Glu Lys Glu Ala Pro Ala
                900                 905                 910

Lys Val Glu Val Lys Glu Asp Ala Lys Pro Lys Glu Lys Thr Glu Val
                915                 920                 925

Ala Lys Lys Glu Pro Asp Asp Ala Lys Ala Lys Glu Pro Ser Lys Pro
930                 935                 940

Ala Glu Lys Lys Glu Ala Ala Pro Glu Lys Lys Asp Thr Lys Glu Glu
945                 950                 955                 960

Lys Ala Lys Lys Pro Glu Glu Pro Lys Thr Glu Ala Lys Ala Lys
                965                 970                 975

Glu Asp Asp Lys Thr Leu Ser Lys Glu Pro Ser Lys Pro Lys Ala Glu
                980                 985                 990

Lys Ala Glu Lys Ser Ser Ser Thr Asp Gln Lys Asp Ser Lys Pro Pro
                995                 1000                1005

Glu Lys Ala Thr Glu Asp Lys Ala Ala Lys Gly Lys
                1010                1015                1020

<210> SEQ ID NO 6
<211> LENGTH: 540
<212> TYPE: PRT
<213> ORGANISM: Homo sapiens

<400> SEQUENCE: 6

Met Ala Arg His Leu Arg Glu Tyr Gln Asp Leu Leu Asn Val Lys Met
1               5                   10                  15

Ala Leu Asp Ile Glu Ile Ala Ala Tyr Arg Lys Leu Leu Glu Gly Glu
                20                  25                  30

Glu Thr Arg Phe Ser Thr Phe Ala Gly Ser Ile Thr Gly Pro Leu Tyr
            35                  40                  45

Thr His Arg Pro Pro Ile Thr Ile Ser Ser Lys Ile Gln Lys Pro Lys
        50                  55                  60

Val Glu Ala Pro Lys Leu Lys Val Gln His Lys Phe Val Glu Glu Ile
65                  70                  75                  80

Ile Glu Glu Thr Lys Val Glu Asp Glu Lys Ser Glu Met Glu Glu Ala
                85                  90                  95

Leu Thr Ala Ile Thr Glu Glu Leu Ala Val Ser Met Lys Glu Glu Lys
                100                 105                 110

Lys Glu Ala Ala Glu Glu Lys Glu Glu Glu Pro Glu Ala Glu Glu Glu
                115                 120                 125

Glu Val Ala Ala Lys Lys Ser Pro Val Lys Ala Thr Ala Pro Glu Val
                130                 135                 140

Lys Glu Glu Glu Gly Glu Lys Glu Glu Glu Gly Gln Glu Glu Glu
145                 150                 155                 160

Glu Glu Glu Asp Glu Gly Ala Lys Ser Asp Gln Ala Glu Glu Gly Gly
                165                 170                 175

Ser Glu Lys Glu Gly Ser Ser Glu Lys Glu Glu Gly Glu Gln Glu Glu
                180                 185                 190

Gly Glu Thr Glu Ala Glu Ala Glu Gly Glu Glu Ala Glu Ala Lys Glu
                195                 200                 205
```

Glu Lys Lys Val Glu Lys Ser Glu Glu Val Ala Thr Lys Glu
    210                 215                 220

Leu Val Ala Asp Ala Lys Val Glu Lys Pro Glu Lys Ala Lys Ser Pro
225                 230                 235                 240

Val Pro Lys Ser Pro Val Glu Glu Lys Gly Lys Ser Pro Val Pro Lys
                245                 250                 255

Ser Pro Val Glu Glu Lys Gly Lys Ser Pro Val Pro Lys Ser Pro Val
                260                 265                 270

Glu Glu Lys Gly Lys Ser Pro Val Pro Lys Ser Pro Val Glu Glu Lys
            275                 280                 285

Gly Lys Ser Pro Val Ser Lys Ser Pro Val Glu Glu Lys Ala Lys Ser
290                 295                 300

Pro Val Pro Lys Ser Pro Val Glu Glu Ala Lys Ser Lys Ala Glu Val
305                 310                 315                 320

Gly Lys Gly Glu Gln Lys Glu Glu Glu Lys Glu Val Lys Glu Ala
            325                 330                 335

Pro Lys Glu Glu Lys Val Glu Lys Lys Glu Glu Lys Pro Lys Asp Val
                340                 345                 350

Pro Glu Lys Lys Lys Ala Glu Ser Pro Val Lys Glu Glu Ala Val Ala
            355                 360                 365

Glu Val Val Thr Ile Thr Lys Ser Val Lys Val His Leu Glu Lys Glu
    370                 375                 380

Thr Lys Glu Glu Gly Lys Pro Leu Gln Gln Glu Lys Glu Lys Glu Lys
385                 390                 395                 400

Ala Gly Gly Glu Gly Ser Glu Glu Gly Ser Asp Lys Gly Ala
                405                 410                 415

Lys Gly Ser Arg Lys Glu Asp Ile Ala Val Asn Gly Glu Val Glu Gly
            420                 425                 430

Lys Glu Glu Val Glu Gln Glu Thr Lys Glu Lys Gly Ser Gly Arg Glu
            435                 440                 445

Glu Glu Lys Gly Val Val Thr Asn Gly Leu Asp Leu Ser Pro Ala Asp
    450                 455                 460

Glu Lys Lys Gly Gly Asp Lys Ser Glu Glu Lys Val Val Val Thr Lys
465                 470                 475                 480

Thr Val Glu Lys Ile Thr Ser Glu Gly Gly Asp Gly Ala Thr Lys Tyr
                485                 490                 495

Ile Thr Lys Ser Val Thr Val Thr Gln Lys Val Glu Glu His Glu Glu
            500                 505                 510

Thr Phe Glu Glu Lys Leu Val Ser Thr Lys Lys Val Glu Lys Val Thr
    515                 520                 525

Ser His Ala Ile Val Lys Glu Val Thr Gln Ser Asp
    530                 535                 540

<210> SEQ ID NO 7
<211> LENGTH: 499
<212> TYPE: PRT
<213> ORGANISM: Homo sapiens

<400> SEQUENCE: 7

Met Ser Phe Gly Ser Glu His Tyr Leu Cys Ser Ser Ser Tyr Arg
1               5                   10                  15

Lys Val Phe Gly Asp Gly Ser Arg Leu Ser Ala Arg Leu Ser Gly Ala
                20                  25                  30

Gly Gly Ala Gly Gly Phe Arg Ser Gln Ser Leu Ser Arg Ser Asn Val

```
                    35                  40                  45
Ala Ser Ser Ala Ala Cys Ser Ser Ala Ser Ser Leu Gly Leu Gly Leu
 50                  55                  60
Ala Tyr Arg Arg Pro Pro Ala Ser Asp Gly Leu Asp Leu Ser Gln Ala
 65                  70                  75                  80
Ala Ala Arg Thr Asn Glu Tyr Lys Ile Ile Arg Thr Asn Glu Lys Glu
                     85                  90                  95
Gln Leu Gln Gly Leu Asn Asp Arg Phe Ala Val Phe Ile Glu Lys Val
                100                 105                 110
His Gln Leu Glu Thr Gln Asn Arg Ala Leu Glu Ala Glu Leu Ala Ala
                115                 120                 125
Leu Arg Gln Arg His Ala Glu Pro Ser Arg Val Gly Glu Leu Phe Gln
                130                 135                 140
Arg Glu Leu Arg Asp Leu Arg Ala Gln Leu Glu Ala Ser Ser Ala
145                 150                 155                 160
Arg Ser Gln Ala Leu Leu Glu Arg Asp Gly Leu Ala Glu Glu Val Gln
                    165                 170                 175
Arg Leu Arg Ala Arg Cys Glu Glu Ser Arg Gly Arg Glu Gly Ala
                    180                 185                 190
Glu Arg Ala Leu Lys Ala Gln Gln Arg Asp Val Asp Gly Ala Thr Leu
                    195                 200                 205
Ala Arg Leu Asp Leu Glu Lys Lys Val Glu Ser Leu Leu Asp Glu Leu
210                 215                 220
Ala Phe Val Arg Gln Val His Asp Glu Glu Val Ala Glu Leu Leu Ala
225                 230                 235                 240
Thr Leu Gln Ala Ser Ser Gln Ala Ala Glu Val Asp Val Thr Val
                    245                 250                 255
Ala Lys Pro Asp Leu Thr Ser Ala Leu Arg Glu Ile Arg Ala Gln Tyr
                    260                 265                 270
Glu Ser Leu Ala Ala Lys Asn Leu Gln Ser Ala Glu Glu Trp Tyr Lys
                    275                 280                 285
Ser Lys Phe Ala Asn Leu Asn Glu Gln Ala Ala Arg Ser Thr Glu Ala
                    290                 295                 300
Ile Arg Ala Ser Arg Glu Glu Ile His Glu Tyr Arg Arg Gln Leu Gln
305                 310                 315                 320
Ala Arg Thr Ile Glu Ile Glu Gly Leu Arg Gly Ala Asn Glu Ser Leu
                    325                 330                 335
Glu Arg Gln Ile Leu Glu Leu Glu Glu Arg His Ser Ala Glu Val Ala
                    340                 345                 350
Gly Tyr Gln Asp Ser Ile Gly Gln Leu Glu Asn Asp Leu Arg Asn Thr
                    355                 360                 365
Lys Ser Glu Met Ala Arg His Leu Arg Glu Tyr Gln Asp Leu Leu Asn
                    370                 375                 380
Val Lys Met Ala Leu Asp Ile Glu Ile Ala Ala Tyr Arg Lys Leu Leu
385                 390                 395                 400
Glu Gly Glu Glu Thr Arg Phe Ser Thr Ser Gly Leu Ser Ile Ser Gly
                    405                 410                 415
Leu Asn Pro Leu Pro Asn Pro Ser Tyr Leu Leu Pro Pro Arg Ile Leu
                    420                 425                 430
Ser Ala Thr Thr Ser Lys Val Ser Ser Thr Gly Leu Ser Leu Lys Lys
                    435                 440                 445
Glu Glu Glu Glu Glu Glu Ala Ser Lys Val Ala Ser Lys Lys Thr Ser
                    450                 455                 460
```

Gln Ile Gly Glu Ser Phe Glu Glu Ile Leu Glu Thr Val Ile Ser
465                 470                 475                 480

Thr Lys Lys Thr Glu Lys Ser Asn Ile Glu Thr Thr Ile Ser Ser
                485                 490                 495

Gln Lys Ile

<210> SEQ ID NO 8
<211> LENGTH: 470
<212> TYPE: PRT
<213> ORGANISM: Homo sapiens

<400> SEQUENCE: 8

Met Ser His His Pro Ser Gly Leu Arg Ala Gly Phe Ser Ser Thr Ser
1               5                   10                  15

Tyr Arg Arg Thr Phe Gly Pro Pro Ser Leu Ser Pro Gly Ala Phe
                20                  25                  30

Ser Tyr Ser Ser Ser Arg Phe Ser Ser Arg Leu Leu Gly Ser
                35                  40                  45

Ala Ser Pro Ser Ser Val Arg Leu Gly Ser Phe Arg Ser Pro Arg
50                  55                  60

Ala Gly Ala Gly Ala Leu Leu Arg Leu Pro Ser Glu Arg Leu Asp Phe
65                  70                  75                  80

Ser Met Ala Glu Ala Leu Asn Gln Glu Phe Leu Ala Thr Arg Ser Asn
                85                  90                  95

Glu Lys Gln Glu Leu Gln Glu Leu Asn Asp Arg Phe Ala Asn Phe Ile
                100                 105                 110

Glu Lys Val Arg Phe Leu Glu Gln Gln Asn Ala Ala Leu Arg Gly Glu
                115                 120                 125

Leu Ser Gln Ala Arg Gly Gln Glu Pro Ala Arg Ala Asp Gln Leu Cys
130                 135                 140

Gln Gln Glu Leu Arg Glu Leu Arg Arg Glu Leu Glu Leu Leu Gly Arg
145                 150                 155                 160

Glu Arg Asp Arg Val Gln Val Glu Arg Asp Gly Leu Ala Glu Asp Leu
                165                 170                 175

Ala Ala Leu Lys Gln Arg Leu Glu Glu Glu Thr Arg Lys Arg Glu Asp
                180                 185                 190

Ala Glu His Asn Leu Val Leu Phe Arg Lys Asp Val Asp Ala Thr
                195                 200                 205

Leu Ser Arg Leu Glu Leu Glu Arg Lys Ile Glu Ser Leu Met Asp Glu
210                 215                 220

Ile Glu Phe Leu Lys Lys Leu His Glu Glu Glu Leu Arg Asp Leu Gln
225                 230                 235                 240

Val Ser Val Glu Ser Gln Gln Val Gln Gln Val Glu Val Glu Ala Thr
                245                 250                 255

Val Lys Pro Glu Leu Thr Ala Ala Leu Arg Asp Ile Arg Ala Gln Tyr
                260                 265                 270

Glu Ser Ile Ala Ala Lys Asn Leu Gln Glu Ala Glu Glu Trp Tyr Lys
                275                 280                 285

Ser Lys Tyr Ala Asp Leu Ser Asp Ala Ala Asn Arg Asn His Glu Ala
                290                 295                 300

Leu Arg Gln Ala Lys Gln Glu Met Asn Glu Ser Arg Arg Gln Ile Gln
305                 310                 315                 320

Ser Leu Thr Cys Glu Val Asp Gly Leu Arg Gly Thr Asn Glu Ala Leu
                325                 330                 335

```
Leu Arg Gln Leu Arg Glu Leu Glu Glu Gln Phe Ala Leu Glu Ala Gly
            340             345             350

Gly Tyr Gln Ala Gly Ala Ala Arg Leu Glu Glu Glu Leu Arg Gln Leu
            355             360             365

Lys Glu Glu Met Ala Arg His Leu Arg Glu Tyr Gln Glu Leu Leu Asn
    370             375             380

Val Lys Met Ala Leu Asp Ile Glu Ile Ala Thr Tyr Arg Lys Leu Leu
385             390             395             400

Glu Gly Glu Glu Ser Arg Ile Ser Val Pro Val His Ser Phe Ala Ser
                405             410             415

Leu Asn Ile Lys Thr Thr Val Pro Glu Val Glu Pro Pro Gln Asp Ser
            420             425             430

His Ser Arg Lys Thr Val Leu Ile Lys Thr Ile Glu Thr Arg Asn Gly
            435             440             445

Glu Val Val Thr Glu Ser Gln Lys Glu Gln Arg Ser Glu Leu Asp Lys
    450             455             460

Ser Ser Ala His Ser Tyr
465             470
```

METHODS OF TREATING SPINAL MUSCULAR ATROPHY

CROSS-REFERENCE TO RELATED APPLICATIONS

This application is the U.S. national stage of application number PCT/US2019/015185, filed on Jan. 25, 2019, which claims priority to U.S. Provisional Appl. No. 62/622,027, filed Jan. 25, 2018, U.S. Provisional Appl. No. 62/684,507, filed Jun. 13, 2018, and U.S. Provisional Appl. No. 62/738,134, filed Sep. 28, 2018. The content of the prior applications are incorporated by reference herein in their entirety.

TECHNICAL FIELD

This disclosure relates generally to biomarkers of spinal muscular atrophy.

BACKGROUND

Spinal Muscular Atrophy (SMA) is an autosomal recessive genetic disorder resulting in a deficiency in the SMN protein, which in turn leads to the loss of anterior horn motor neurons, axonal degradation, and a phenotype of progressive muscle wasting, mobility impairment, and respiratory failure. Disease severity is categorized into five types (0-4) with type 0 patients having the most severe (neonatal lethal) phenotype and type 4 patients having only the mildest symptoms and normal lifespan.

Timely and proper treatment of subjects with SMA requires the ability to select presymptomatic subjects in need of treatment with a therapy for treating SMA and determine whether the SMA therapy is effective. Thus, there is a need for biomarkers of SMA.

SUMMARY

Neurofilaments are a major component of the neuronal cytoskeleton, particularly in axons where they are essential for growth and maintenance. Structurally, they consist of three intertwined core subunits: neurofilament heavy (NF-H), medium/intermediate (NF-M) and light (NF-L) polypeptides that form the "neurofilament triplet." This disclosure is based, at least in part, on the finding that neurofilament levels serve as effective biomarkers for spinal muscular atrophy (SMA).

In one aspect, the disclosure features a method of treating SMA in a human subject in need thereof. The method involves administering to the human subject a therapeutically effective amount of an SMA therapy, wherein the human subject has been previously determined to have, in a biological sample obtained from the human subject, a neurofilament level prior to initiation of the SMA therapy that is higher than a control. This method can be used, for example, in treating a subject who is presymptomatic.

In another aspect, the disclosure provides a method of treating SMA in a human subject in need thereof. The method involves measuring a neurofilament level in a biological sample obtained from the human subject before initiation of an SMA therapy and administering a therapeutically effective amount of the SMA therapy to the human subject.

In some embodiments of the above two aspects, the neurofilament level (e.g., phosphorylated neurofilament heavy (pNF-H) level) in the biological sample is above a control level. In some embodiments, the neurofilament level (e.g., pNF-H level) in the biological sample is above 300 pg/mL. In some embodiments the neurofilament level (e.g., pNF-H level) in the biological sample is above 400 pg/mL. In some embodiments, the neurofilament level (e.g., pNF-H level) in the biological sample is above 500 pg/mL. In some embodiments, the neurofilament level (e.g., pNF-H level) in the biological sample is above 600 pg/mL. In some embodiments, the neurofilament level (e.g., pNF-H level) in the biological sample is above 700 pg/mL. In some embodiments, the neurofilament level (e.g., pNF-H level) in the biological sample is above 800 pg/mL. In some embodiments, the neurofilament level (e.g., pNF-H level) in the biological sample is above 900 pg/mL. In some embodiments, the neurofilament level (e.g., pNF-H level) in the biological sample is above 1,000 pg/mL. In some embodiments, the neurofilament level (e.g., pNF-H level) in the biological sample is above 1,100 pg/mL. In some embodiments, the neurofilament level (e.g., pNF-H level) in the biological sample is above 1,200 pg/mL. In some embodiments, the neurofilament level (e.g., pNF-H level) in the biological sample is above 1,300 pg/mL. In some embodiments, the neurofilament level (e.g., pNF-H level) in the biological sample is above 1,400 pg/mL. In some embodiments, the neurofilament level (e.g., pNF-H level) in the biological sample is above 1,500 pg/mL. In some embodiments, the neurofilament level (e.g., pNF-H level) in the biological sample is above 2,000 pg/mL. In some embodiments, the neurofilament level (e.g., pNF-H level) in the biological sample is above 3,000 pg/mL. In some embodiments, the neurofilament level (e.g., pNF-H level) in the biological sample is above 4,000 pg/mL. In some embodiments, the neurofilament level (e.g., pNF-H level) in the biological sample is above 5,000 pg/mL. These neurofilament levels can be obtained using assays described in the examples section of this application. It should be understood that if a different neurofilament assay is used that provides a different read out (e.g., O.D. or International Units), the values for neurofilament levels could be different.

In another aspect, the disclosure features a method of treating SMA in a human subject in need thereof. The method involves: measuring a neurofilament level (e.g., pNF-H level) in a first biological sample obtained from the human subject before initiation of an SMA therapy; administering an SMA therapy (e.g., a therapeutically effective amount of the SMA therapy) to the human subject; and measuring a neurofilament level (e.g., pNF-H level) in a second biological sample obtained from the human subject after initiation of the SMA therapy.

In another aspect, the disclosure features a method of treating SMA in a human subject in need thereof. The method involves: measuring a neurofilament level (e.g., pNF-H level) in a first biological sample obtained from the human subject before administration of a candidate amount of an SMA therapy; measuring a neurofilament level (e.g., pNF-H level) in a second biological sample obtained from the human subject after administration of the candidate amount of the SMA therapy, wherein the neurofilament level in the second biological sample is lower than the neurofilament level in the first biological sample, thereby indicating that the candidate amount of the SMA therapy is a therapeutically effective amount; and administering the therapeutically effective amount of the SMA therapy to the human subject after having measured the lowered neurofilament level in the second biological sample.

In certain embodiments, neurofilament level (e.g., pNF-H level) in a first biological sample is above 300 pg/mL, above 400 pg/mL, above 500 pg/mL, above 600 pg/mL, above 700 pg/mL, above 800 pg/mL, above 900 pg/mL, above 1,000 pg/mL, above 1,500 pg/mL, above 2,000 pg/mL, above 3,000 pg/mL, above 4,000 pg/mL, or above 5,000 pg/mL. In certain embodiments, the neurofilament level (e.g., pNF-H level) measured in the second biological sample is lower than the neurofilament level measured in the first biological sample. In some embodiments, the neurofilament level (e.g., pNF-H level) measured in the second biological sample shows a greater than 30% decline relative to the neurofilament level measured in the first biological sample. In some embodiments, the neurofilament level (e.g., pNF-H level) measured in the second biological sample is between 10% to 80% of the neurofilament level measured in the first biological sample. In some embodiments, the neurofilament level (e.g., pNF-H level) measured in the second biological sample is between 20% to 95% of the neurofilament level measured in the first biological sample. In some embodiments, the neurofilament level (e.g., pNF-H level) measured in the second biological sample is between 30% to 90% of the neurofilament level measured in the first biological sample. In some embodiments, the neurofilament level (e.g., pNF-H level) measured in the second biological sample is between 30% to 95% of the neurofilament level measured in the first biological sample. In such instances, administration of the SMA therapy is continued. In certain embodiments, the neurofilament level (e.g., pNF-H level) measured in the second biological sample is higher than the neurofilament level measured in the first biological sample. In such instances, administration of the SMA therapy is discontinued.

In some embodiments, the second biological sample is obtained from the human subject 40-90 days after initiation of the SMA therapy. In some embodiments, the second biological sample is obtained from the human subject 50-80 days after initiation of the SMA therapy. In some embodiments, the second biological sample is obtained from the human subject 60-70 days after initiation of the SMA therapy. In some embodiments, the second biological sample is obtained from the human subject about 64 days after initiation of the SMA therapy.

In some embodiments where the second biological sample is obtained from the human subject 40-90 days, 50-80 days, 60-70 days, or about 64 days after initiation of the SMA therapy, the neurofilament level measured in the second biological sample is reduced by at least 50% compared to the neurofilament level measured in the first biological sample. In some embodiments where the second biological sample is obtained from the human subject 40-90 days, 50-80 days, 60-70 days, or about 64 days after initiation of the SMA therapy, the neurofilament level measured in the second biological sample is reduced by at least 60% compared to the neurofilament level measured in the first biological sample. In some embodiments where the second biological sample is obtained from the human subject 40-90 days, 50-80 days, 60-70 days, or about 64 days after initiation of the SMA therapy, the neurofilament level measured in the second biological sample is reduced by at least 70% compared to the neurofilament level measured in the first biological sample.

In some embodiments where the second biological sample is obtained from the human subject 40-90 days, 50-80 days, 60-70 days, or about 64 days after initiation of the SMA therapy, the neurofilament level measured in the second biological sample is reduced by less than 50% compared to the neurofilament level measured in the first biological sample. In some embodiments where the second biological sample is obtained from the human subject 40-90 days, 50-80 days, 60-70 days, or about 64 days after initiation of the SMA therapy, the neurofilament level measured in the second biological sample is reduced by less than 40% compared to the neurofilament level measured in the first biological sample.

In some embodiments where the second biological sample is obtained from the human subject 40-90 days, 50-80 days, 60-70 days, or about 64 days after initiation of the SMA therapy, the dose of the SMA therapy is changed for a subsequent administration to the human subject based upon the percent reduction in neurofilament level measured in the second biological sample as compared to the neurofilament level measured in the first biological sample.

In another aspect, the disclosure relates to a method of predicting the prognosis of SMA. The method involves measuring a neurofilament level (e.g., pNF-H level) in a biological sample obtained from a human subject having mutations in both copies of the SMN1 gene (the mutations can be homozygous or heterozygous) that lead to functional SMN protein deficiency. The method further involves comparing the neurofilament level (e.g., pNF-H level) measured in the biological sample to a control. The neurofilament level (e.g., pNF-H level) measured in the biological sample, as compared to the control, is predictive of the severity or type of SMA that the subject will develop.

In certain embodiments, the biological sample is obtained from the human subject before initiation of an SMA therapy, and the neurofilament level (e.g., pNF-H level) measured in the biological sample, as compared to the control, is predictive of the severity or type of SMA that the human subject will develop in the absence of treatment.

In some embodiments, the biological sample is obtained from the human subject after initiation of an SMA therapy, and the neurofilament level (e.g., pNF-H level) measured in the biological sample, as compared to the control, is predictive of the severity or type of SMA that the subject will develop while receiving the SMA therapy. In certain instances, the biological sample is obtained from the human subject at least two weeks after initiation of the SMA therapy. In certain instances, the biological sample is obtained from the human subject at least four weeks after initiation of the SMA therapy. In certain instances, the biological sample is obtained from the human subject at least six weeks after initiation of the SMA therapy. In certain instances, the biological sample is obtained from the human subject at least eight weeks after initiation of the SMA therapy. In certain instances, the biological sample is obtained from the human subject at least ten weeks after initiation of the SMA therapy. In certain instances, the biological sample is obtained from the human subject at least twelve weeks after initiation of the SMA therapy. In certain instances, the biological sample is obtained from the human subject at least two months after initiation of the SMA therapy. In certain instances, the biological sample is obtained from the human subject at least three months after initiation of the SMA therapy. In certain instances, the biological sample is obtained from the human subject at least four months after initiation of the SMA therapy. In certain instances, the biological sample is obtained from the human subject at least five months after initiation of the SMA therapy. In certain instances, the biological sample is obtained from the human subject at least six months after initiation of the SMA therapy.

In another aspect, the disclosure relates to a method of predicting the prognosis of SMA. The method involves measuring, before initiation of an SMA therapy, a neurofilament level (e.g., pNF-H level) in a first biological sample obtained from a human subject having mutations in both copies of the SMN1 gene (the mutations can be homozygous or heterozygous) that lead to functional SMN protein deficiency. The method further involves measuring a neurofilament level (e.g., pNF-H level) in a second biological sample obtained from the human subject after initiation of the SMA therapy. The method further involves comparing the neurofilament level (e.g., pNF-H level) measured in the second biological sample to the neurofilament level (e.g., pNF-H level) measured in the first biological sample. The neurofilament level (e.g., pNF-H level) measured in the second biological sample, as compared to the neurofilament level (e.g., pNF-H level) measured in the first biological sample, is predictive of the severity or type of SMA that the subject will develop. In general, the greater the percent reduction in neurofilament level (e.g., pNF-H level) in the second biological sample, as compared to the neurofilament level (e.g., pNF-H level) measured in the first biological sample, the better the prognosis for the human subject's future motor function.

In some embodiments, the second biological sample is obtained from the human subject 40-90 days after initiation of the SMA therapy. In some embodiments, the second biological sample is obtained from the human subject 50-80 days after initiation of the SMA therapy. In some embodiments, the second biological sample is obtained from the human subject 60-70 days after initiation of the SMA therapy. In some embodiments, the second biological sample is obtained from the human subject about 64 days after initiation of the SMA therapy.

In some embodiments where the second biological sample is obtained from the human subject 40-90 days, 50-80 days, 60-70 days, or about 64 days after initiation of the SMA therapy, the neurofilament level measured in the second biological sample is reduced by at least 50% compared to the neurofilament level measured in the first biological sample. In some embodiments where the second biological sample is obtained from the human subject 40-90 days, 50-80 days, 60-70 days, or about 64 days after initiation of the SMA therapy, the neurofilament level measured in the second biological sample is reduced by at least 60% compared to the neurofilament level measured in the first biological sample. In some embodiments where the second biological sample is obtained from the human subject 40-90 days, 50-80 days, 60-70 days, or about 64 days after initiation of the SMA therapy, the neurofilament level measured in the second biological sample is reduced by at least 70% compared to the neurofilament level measured in the first biological sample.

In some embodiments where the second biological sample is obtained from the human subject 40-90 days, 50-80 days, 60-70 days, or about 64 days after initiation of the SMA therapy, the neurofilament level measured in the second biological sample is reduced by less than 50% compared to the neurofilament level measured in the first biological sample. In some embodiments where the second biological sample is obtained from the human subject 40-90 days, 50-80 days, 60-70 days, or about 64 days after initiation of the SMA therapy, the neurofilament level measured in the second biological sample is reduced by less than 40% compared to the neurofilament level measured in the first biological sample.

The following embodiments apply to any of the above aspects. In certain instances, the SMA therapy comprises nusinersen or a nusinersen salt. In some instances, the SMA therapy comprises nusinersen sodium. In certain instances, nusinersen sodium is administered by intrathecal injection of 5 mL of a 2.4 mg/mL solution. In certain instances, the SMA therapy comprises one or more of SPINRAZA®, olesoxime, AVX-101, CK-2127107, RG7916, RG7800, RO7034067, LMI070, or SRK-015. In certain instances, the SMA therapy comprises a small molecule. In certain instances, the SMA therapy comprises gene therapy. In certain instances, the SMA therapy comprises a p38aDMAPK inhibitor. In certain instances, the SMA therapy comprises a DcpS inhibitor. In certain instances, the SMA therapy comprises a JNK inhibitor. In certain instances, the control is a pre-established neurofilament cut-off value. In some instances, the control is the neurofilament level (e.g., pNF-H level) in a biological sample or biological samples obtained from one or more human subjects that do not have SMA.

In another aspect, the disclosure features a method for measuring a neurofilament level (e.g., pNF-H level). The method involves providing a biological sample obtained from a human subject having mutations in both copies of the SMN1 gene that lead to functional SMN protein deficiency; and measuring a neurofilament level (e.g., pNF-H level) in the biological sample.

These embodiments apply to any of the above aspects. In certain instances, the neurofilament is a neurofilament heavy chain (e.g., phosphorylated NF-H). In certain instances, the neurofilament is a neurofilament medium/intermediate chain. In certain instances, the neurofilament is a neurofilament light chain. In certain instances, the neurofilament is internexin. In certain instances, the neurofilament is peripherin. In certain instances, the biological sample is blood, serum, plasma, or cerebrospinal fluid. In some instances, NF-H is detected using a polyclonal anti-NF-H antibody. In some instances, NF-H is detected using a polyclonal anti-NF-H antibody that specifically detects the hyper-phosphorylated form of NF-H (e.g., Encor Biotechnology Cat #RPCA-NF-H; and/or Cat #CPCA-NF-H). In some cases, NF-H is detected using a monoclonal anti-NF-H antibody. In certain embodiments, the human subject is a fetus. In certain embodiments, the human subject is an infant. In certain embodiments, the human subject is less than 6 months of age. In certain embodiments, the human subject is older than 6 months of age. In certain embodiments, the human subject is a child less than 12 years of age. In certain embodiments, the human subject is a child less than 18 years of age. In certain embodiments, the human subject is an adult 18 years or older.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description and from the claims.

BRIEF DESCRIPTION OF THE DRAWINGS

FIG. 6 is a table providing baseline characteristics and SMA History by baseline pNF-H level.

FIG. 7 is a table providing baseline characteristics and SMA History by baseline pNF-H level.

FIG. 8 is a table providing baseline characteristics and SMA History by baseline pNF-H level.

FIG. 10 is a table showing the ability to correlate phenotypes at baseline by pNF-H levels in ENDEAR.

FIG. 17 shows the association of HINE-2 Score on Day 183 with pNF-H levels on Day 64 (with Covariates).

FIG. 19 shows the association of CHOP INTEND Score on Day 183 with pNF-H levels on Day 64 (with Covariates).

FIG. 28 are graphs depicting the association of HINE-2 score on Day 183 with pNF-H levels on Day 64. For top graph: Root MSE: 2.87069; R-square: 0.0184; Adjusted R-square: 0.0002. For bottom graph: Root MSE: 1.70576; R-square: 0.224; Adjusted R-square: 0.1831. DF=degrees of freedom; MSE=mean square error.

FIG. 29 are graphs depicting the association of CHOP INTEND score on Day 183 with pNF-H levels on Day 64. For top graph: Root MSE: 10.09399; R-square: 0.0754; Adjusted R-square: 0.0583. For bottom graph: Root MSE: 9.41166; R-square: 0.2176; Adjusted R-square: 0.1764. DF=degrees of freedom; MSE=mean square error.

FIG. 33 are graphs depicting the association of Peroneal CMAP Amplitude on Day 183 with pNF-H levels on Day 64. For top graph: Root MSE: 0.56401; R-square: 0.0164; Adjusted R-square: −0.0029. For bottom graph: Root MSE: 0.18933; R-square: 0.2906; Adjusted R-square: 0.2512. DF=degrees of freedom; MSE=mean square error.

FIG. 35 are graphs depicting the association of Ulnar CMAP Amplitude on Day 183 with pNF-H levels on Day 64. For top graph: Root MSE: 0.2824; R-square: 0.0517; Adjusted R-square: 0.0338. For bottom graph: Root MSE: 0.11118; R-square: 0.2406; Adjusted R-square: 0.1984. DF=degrees of freedom; MSE=mean square error.

DETAILED DESCRIPTION

Figure 1:
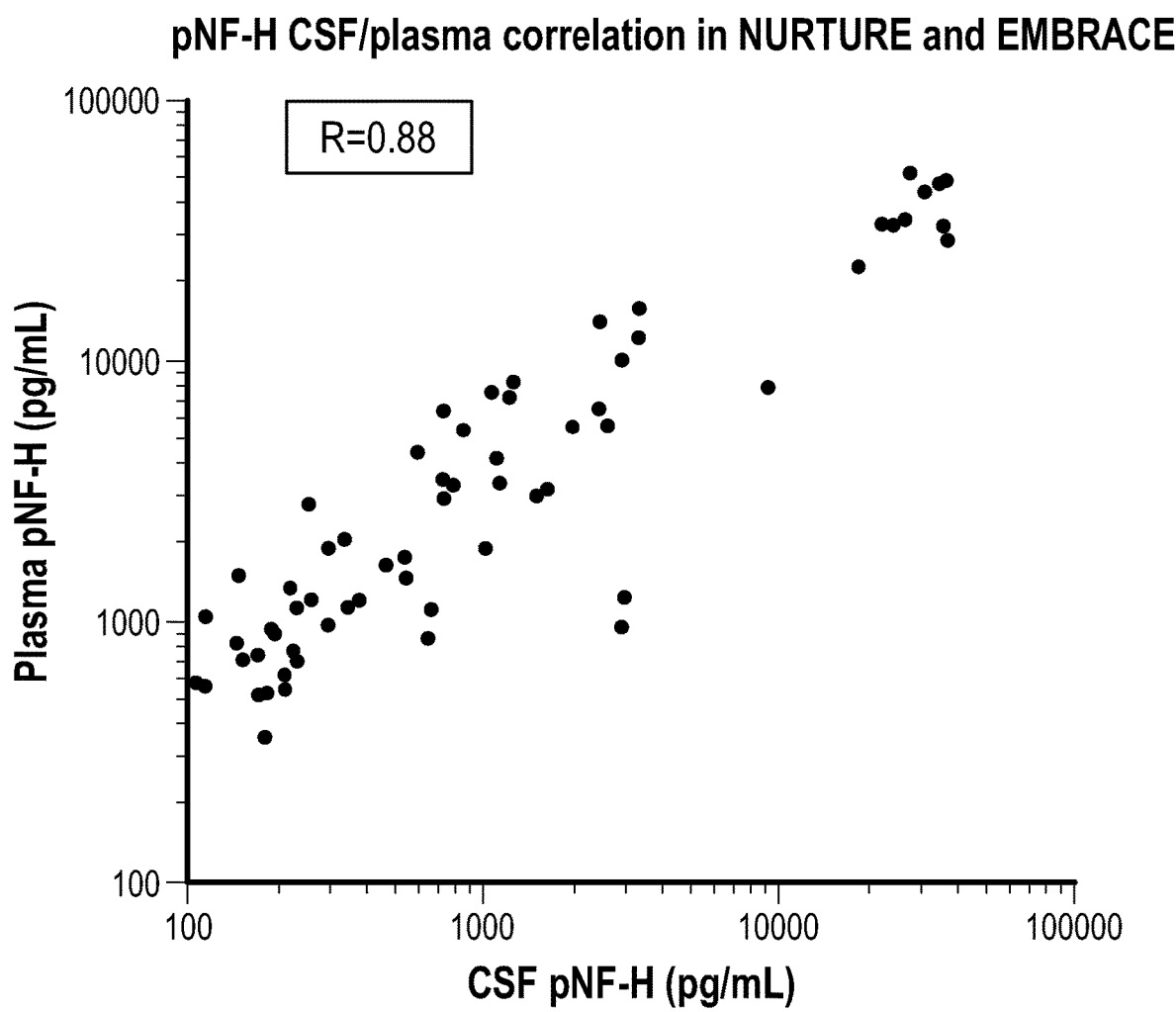
FIG. 1 shows the levels of phosphorylated neurofilament heavy chain (pNF-H) levels in plasma and CSF samples at the same timepoint and in the same subject from EMBRACE and NURTURE clinical studies.

This disclosure is based, in part, on the surprising finding that neurofilament (NF) levels can serve as an effective biomarker for SMA.

1. Spinal Muscular Atrophy

After cystic fibrosis, spinal muscular atrophy (SMA) is the second most common lethal autosomal recessive disorder among Caucasians. This disease is characterized by the progressive degeneration of the alpha motoneurons in the anterior horn of the spinal cord, which leads to muscle atrophy, paralysis, and sometimes even death. The most common form of SMA is caused by mutations in the 5q13 survival of the motor neuron (SMN1) gene. This disorder affects 1 in 6,000 to 10,000 infants, with a carrier frequency of 1 in 40. Several clinical types have been described for SMA, which group the disorder according to the age onset and the progression of the symptoms.

According to the above classification, there are five types of SMA: type 0 (embryonic form), type I (Werdning-Hoffman), type II (intermediate), type III (Kugeleberg-Welander), and type IV (adult form). Type 0, the most severe, is characterized by reduced movement of the fetus between 30-36 weeks of the pregnancy and a very short life expectancy. Type I is the next most severe form, with an onset before the age of 6 months and a life expectation of around 2 years. Types II and III are known as chronic forms and are less severe, with an onset between 6-18 months (type II) and respectively after 18 months (for type III). In many cases, Type IV mimics the symptoms of type III, but the onset is after 18 years of age (typically around 30 years old). A normal life expectancy is characteristic for this adult form.

The SMA determining gene, SMN1, was mapped to the 5q11.2-13.3 region. The homozygous deletion of SMN1 exon 7 is the most common mutation found in SMA patients; however, there are several cases of compound heterozygous patients in whom deletions and different point mutations have been detected. In humans, two forms of the SMN gene exist on each allele: a telomeric form (SMN1) and a centromeric form (SMN2). Transcription of the SMN1 gene produces full-length messenger RNA (mRNA) transcripts that encode the SMN protein. The SMN2 gene is identical to the SMN1 gene with the exception of a C to T substitution at position 840 that results in the exclusion of exon 7 during transcription. The resultant truncated protein is not functional and is rapidly degraded. Importantly, the exclusion of exon 7 from SMN2 mRNAs is not complete, and so a small fraction of the total mRNA transcripts (approximately 10% to 15%) arising from the SMN2 gene contain exon 7, which encodes the normal SMN protein. But the full length SMN protein is synthesized in such a small quantity that it is unable to sustain motor neuron survival.

All patients with SMA lack a functioning SMN1 gene and are thus dependent on their SMN2 gene to produce the SMN protein necessary for survival. Thus, SMA is caused by a deficiency in the SMN protein that results in selective motor neuron loss. Several genotype/phenotype analyses have shown a positive correlation between SMN2 copy number and a milder SMA phenotype. Although SMN2 copy number is a primary determinant of SMA severity, it is clearly not the only phenotypic modifier. The art has described at least three adult patients with mild 3b phenotypes and only 2 copies of SMN2. This seemingly incongruous finding was explained by the fact that these individuals had a c.859G>C exon 7 mutation that created an exon splice—enhancing element that resulted in increased full-length SMN protein production and a milder phenotype. Other modifiers have been described and more are expected as the understanding of the molecular pathogenesis of SMA is refined. These findings show that the SMA phenotype cannot always be deduced solely from the SMN2 copy number determination.

2. Therapies for SMA

One therapy for the treatment of SMA is SPINRAZA®, a compound containing nusinersen (also known as ASO-10-27 ISIS 396443 ISIS SMNRx/ISIS-396443/ISIS-SMNRx). Nusinersen is a modified antisense oligonucleotide compound (modified in that the 2'-hydroxy groups of the ribofuranosyl rings are replaced with 2'-O-2-methoxyethyl groups and the phosphate linkages are replaced with phosphorothioate linkages) that binds to a specific sequence of the SMN2 transcript in the intron downstream of exon 7. The sodium salt of nusinersen (nusinersen sodium) is marketed under the trade name SPINRAZA®. Nusinersen is designed to treat SMA caused by mutations in chromosome 5q that lead to SMN protein deficiency. Using in vitro assays and studies in transgenic animal models of SMA, nusinersen was shown to increase exon 7 inclusion in SMN2 messenger ribonucleic acid (mRNA) transcripts and production of full-length SMN protein. Nusinersen acts to counteract the SMN protein deficit that causes SMA, by increasing the splicing efficiency of the SMN2 pre-mRNA.

Nusinersen is an 18-mer 2'-MOE phosphorothioate antisense oligonucleotide. Nusinersen was designed to pair with a specific target sequence on the SMN2 pre-mRNA to displace heterogeneous ribonucleoproteins (hnRNPs) at the intronic splice silencing site-1 (ISS-1) between exons 7 and 8 to allow for more complete translation of SMN protein from the paralogous gene SMN2. Intrathecal injection of nusinersen into the cerebrospinal fluid (CSF) allows it to be distributed from the CSF to the target central nervous system (CNS) tissues. The full sequence of nusinersen is [2'-O-(2-methoxyethyl)](3'-5)(P-thio) (T-5mC-A-5mC-T-T-T-5mC-A-T-A-A-T-G-5mC-T-G-G) (SEQ ID NO:4). The antisense oligonucleotide contains 2'-O-(2-methoxyethyl) (2'-MOE)-oligoribonucleotides to reduce nuclease degradation and to enhance binding affinity towards the complementary RNA.

There are several other therapies for the treatment of SMA. These include, compounds that increase SMN levels such as historic deacetylase inhibitors; aminoglycosides, and quinazoline derivatives. Histone deacetylase inhibitors such as valproic acid, sodium butyrate, phenylbutyrate, and trichostatin A activate the SMN2 promoter, resulting in increased full-length SMN protein. Other therapies include CK-2127107 (a fast skeletal muscle troponin activator), LM1070 (branaplan, formerly known as NVS-SM1), olesoxime (a cholesterol oximes family member), RG7916 (a splicing modifier), SMN gene therapy (AAV9-SMN1; AVXS-101 (AAV-human SMN transgene)), and SRK-015 (selective and local inhibitor antibody of the latent form of myostatin). In some instances, one or more of these agents are used in combination for the treatment of SMA. The present methods are intended to cover any treatment of SMA.

3. Biomarkers for SMA

In order to identify subjects who would benefit from treatment with an SMA therapy (such as the one or more of the SMA therapies described above) or to determine if a therapy is working it is helpful to have a biomarker. A biomarker is a characteristic that can be objectively measured and evaluated as an indicator of normal biologic processes, pathologic processes, or pharmacological responses to a therapeutic intervention. Biomarkers can be biological (e.g., small molecules, metabolites, peptides, proteins, RNA, DNA), physiological (e.g., blood pressure, electromyography, respiratory function), or structural measures (e.g., ultrasound, magnetic resonance imaging, or histological assessment). The biomarkers may be prognostic biomarkers that predict a future clinical outcome; disease progression biomarkers that are indicative of the severity of disease impact; predictive biomarkers that predict a future clinical response to therapy and helps stratify therapies; pharmacodynamic biomarkers that monitor or quantify a therapeutic effect; and surrogate end point biomarkers that predict a future clinical response to therapy wherein a change in the end point is associated with a future clinical response.

There are several known biomarkers for SMA. These include prognostic biomarkers such as SMN2 copy number as an indicator of disease severity; disease progression biomarkers such as Compound Muscle Action Potential (CMAP) amplitude that serves as an indicator of motor neuron loss; predictive biomarkers such as reduced CMAP amplitude that is indicative of less response to SMN restoring therapies; pharmacodynamic biomarkers such as increased full-length SMN transcripts and/or increased SMN protein as indicators of effective induction of the SMN2 gene; and surrogate end point biomarkers such as increased Motor unit number estimation (MUNE) as an indicator of improved physical function.

This disclosure illustrates the use of neurofilament levels as a novel biomarker for SMA. Neurofilaments (NFs) are the predominant cystokeletal element in nerve cells and play a role not only in conferring mechanical stability but also in determining axonal caliber. Human NFs are composed of three protein subunits, NF-L, NF-M, and NF-H. These proteins share the same basic architecture as other intermediate filament subunit proteins. Neurofilaments in the mammalian nervous system also contain the protein internexin and neurofilaments in the peripheral nervous system can also contain the protein peripherin. Thus, as used herein, by "a neurofilament protein" is meant neurofilament heavy chain (NF-H), neurofilament medium/intermediate chain (NF-M), neurofilament light chain (NF-L), internexin, or peripherin. The SMA biomarker can be one or more of NF-H, NF-M, NF-L, internexin, and peripherin. In certain instances, the SMA biomarker is a phosphorylated NF-H (pNF-H). In certain instances, the SMA biomarker is a phosphorylated NF-L. The levels of the neurofilament biomarker can be assessed using RNA (e.g., mRNA) or protein.

The amino acid sequences of human NF-H are provided in SEQ ID NO:1 and SEQ ID NO:5 and in Lees et al., *EMBO J*, 7(7); 1947-1955 (1988), UniProtKB-P12036, NCBI Reference Sequence: NG_008404.1, NCBI Reference Sequence: NP_066554.2.

SEQ ID NO: 1
MMSFGGADALLGAPFAPLHGGGSLHYALARKGGAGGTRSAAGSSSGFHSW
TRTSVSSVSASPSRFRGAGAASSTDSLDTLSNGPEGCMVAVATSRSEKEQ
LQALNDRFAGYIDKVRQLEAHNRSLEGEAAALRQQQAGRSAMGELYEREV
REMRGAVLRLGAARGQLRLEQEHLLEDIAHVRQRLDDEARQREEAEAAAR
ALARFAQEAEAARVDLQKKAQALQEECGYLRRHHQEEVGELLGQIQGSGA
AQAQMQAETRDALKCDVTSALREIRAQLEGHAVQSTLQSEEWFRVRLDRL
SEAAKVNTDAMRSAQEEITEYRRQLQARTTELEALKSTKDSLERQRSELE
DRHQADIASYQEAIQQLDAELRNTKWEMAAQLREYQDLLNVKMALDIEIA
AYRKLLEGEECRIGFGPIPFSLPEGLPKIPSVSTHIKVKSEEKIKVVEKS
EKETVIVEEQTEETQVTEEVTEEEEKEAKEEEGKEEEGGEEEEAEGGEEE
TKSPPAEEAASPEKEAKSPVKEEAKSPAEAKSPEKEEAKSPAEVKSPEKA
KSPAKEEAKSPPEAKSPEKEEAKSPAEVKSPEKAKSPAKEEAKSPAEAKS
PEKAKSPVKEEAKSPAEAKSPVKEEAKSPAEVKSPEKAKSPTKEEAKSPE
KAKSPEKEEAKSPEKAKSPVKAEAKSPEKAKSPVKAEAKSPEKAKSPVKE
EAKSPEKAKSPVKEEAKSPEKAKSPVKEEAKTPEKAKSPVKEEAKSPEKA
KSPEKAKSPEKAKTLDVKSPEAKTPAKEEARSPADKFPEKAKSPVKEEVK
SPEKAKSPLKEDAKAPEKEIPKKEEVKSPVKEEEKPQEVKVKEPPKKAEE
EKAPATPKTEEKKDSKKEEAPKKEAPKPKVEEKKEPAVEKPKESKVEAKK
EEAEDKKKVPTPEKEAPAKVEVKEDAKPKEKTEVAKKEPDDAKAKEPSKP
AEKKEAAPEKKDTKEEKAKKPEEKPKTEAKAKEDDKTLSKEPSKPKAEKA
EKSSSTDQKDSKPPEKATEDKAAKGK

SEQ ID NO: 5
MMSFGGADALLGAPFAPLHGGGSLHYALARKGGAGGTRSAAGSSSGFHSW
TRTSVSSVSASPSRFRGAGAASSTDSLDTLSNGPEGCMVAVATSRSEKEQ
LQALNDRFAGYIDKVRQLEAHNRSLEGEAAALRQQQAGRSAMGELYEREV
REMRGAVLRLGAARGQLRLEQEHLLEDIAHVRQRLDDEARQREEAEAAAR
ALARFAQEAEAARVDLQKKAQALQEECGYLRRHHQEEVGELLGQIQGSGA
AQAQMQAETRDALKCDVTSALREIRAQLEGHAVQSTLQSEEWFRVRLDRL
SEAAKVNTDAMRSAQEEITEYRRQLQARTTELEALKSTKDSLERQRSELE
DRHQADIASYQEAIQQLDAELRNTKWEMAAQLREYQDLLNVKMALDIEIA
AYRKLLEGEECRIGFGPIPFSLPEGLPKIPSVSTHIKVKSEEKIKVVEKS
EKETVIVEEQTEETQVTEEVTEEEEKEAKEEEGKEEEGGEEEEAEGGEEE
TKSPPAEEAASPEKEAKSPVKEEAKSPAEAKSPEKEEAKSPAEVKSPEKA
KSPAKEEAKSPPEAKSPEKEEAKSPAEVKSPEKAKSPAKEEAKSPAEAKS
PEKAKSPVKEEAKSPAEAKSPVKEEAKSPAEVKSPEKAKSPTKEEAKSPE
KAKSPEKEEAKSPEKAKSPVKAEAKSPEKAKSPVKAEAKSPEKAKSPVKE
EAKSPEKAKSPVKEEAKSPEKAKSPVKEEAKTPEKAKSPVKEEAKSPEKA
KSPEKAKTLDVKSPEAKTPAKEEARSPADKFPEKAKSPVKEEVKSPEKAK
SPLKEDAKAPEKEIPKKEEVKSPVKEEEKPQEVKVKEPPKKAEEEKAPAT
PKTEEKKDSKKEEAPKKEAPKPKVEEKKEPAVEKPKESKVEAKKEEAEDK
KKVPTPEKEAPAKVEVKEDAKPKEKTEVAKKEPDDAKAKEPSKPAEKKEA
APEKKDTKEEKAKKPEEKPKTEAKAKEDDKTLSKEPSKPKAEKAEKSSST
DQKDSKPPEKATEDKAAKGK

The amino acid sequence of human NF-L is provided in SEQ ID NO:2 and in Julien et al., *Biochimica et Biohysica Acta*, 909:10-20 (1987), UniProtKB-P07196, NCBI Reference Sequence: NP_006149.2, and NCBI Reference Sequence: NG_008492.1.

SEQ ID NO: 2
MSSFSYEPYYSTSYKRRYVETPRVHISSVRSGYSTARSAYSSYSAPVSSS
LSVRRSYSSSSGSLMPSLENLDLSQVAAISNDLKSIRTQEKAQLQDLNDR
FASFIERVHELEQQNKVLEAELLVLRQKHSEPSRFRALYEQEIRDLRLAA
EDATNEKQALQGEREGLEETLRNLQARYEEEVLSREDAEGRLMEARKGAD
EAALARAELEKRIDSLMDEISFLKKVHEEEIAELQAQIQYAQISVEMDVT
KPDLSAALKDIRAQYEKLAAKNMQNAEEWFKSRFTVLTESAAKNTDAVRA
AKDEVSESRRLLKAKTLEIEACRGMNEALEKQLQELEDKQNADISAMQDT

INKLENELRTTKSEMARYLKEYQDLLNVKMALDIEIAAYRKLLEGEETRL

SFTSVGSITSGYSQSSQVFGRSAYGGLQTSSYLMSTRSFPSYYTSHVQEE

QIEVEETIEAAKAEEAKDEPPSEGEAEEEEKDKEEAEEEEAAEEEEAAKE

ESEEAKEEEGGEGEEGEETKEAEEEEKKVEGAGEEQAAKKKD

The amino acid sequences of human NF-M are provided in SEQ ID NO:3 and SEQ ID NO:6 and in Myers et al., *EMBO J*, 6(6):1617-1626 (1987) and in UniProtKB-P07197.

SEQ ID NO: 3
MSYTLDSLGNPSAYRRVTETRSSFSRVSGSPSSGFRSQSWSRGSPSTVSS

SYKRSMLAPRLAYSSAMLSSAESSLDFSQSSSLLNGGSGPGGDYKLSRSN

EKEQLQGLNDRFAGYIEKVHYLEQQNKEIEAEIQALRQKQASHAQLGDAY

DQEIRELRATLEMVNHEKAQVQLDSDHLEEDIHRLKERFEEEARLRDDTE

AAIRALRKDIEEASLVKVELDKKVQSLQDEVAFLRSNHEEEVADLLAQIQ

ASHITVERKDYLKTDISTALKEIRSQLESHSDQNMHQAEEWFKCRYAKLT

EAAEQNKEAIRSAKEEIAEYRRQLQSKSIELESVRGTKESLERQLSDIEE

RHNHDLSSYQDTIQQLENELRGTKWEMARHLREYQDLLNVKMALDIEIAA

YRKLLEGEETRFSTFAGSITGPLYTHRPPITISSKIQKPKVEAPKLKVQH

KFVEEIIEETKVEDEKSEMEEALTAITEELAVSMKEEKKEAAEEKEEEPE

AEEEEVAAKKSPVKATAPEVKEEEGEKEEEEGQEEEEEEDEGAKSDQAEE

GGSEKEGSSEKEEGEQEEGETEAEAEGEEAEAKEEKKVEEKSEEVATKEE

LVADAKVEKPEKAKSPVPKSPVEEKGKSPVPKSPVEEKGKSPVPKSPVEE

KGKSPVPKSPVEEKGKSPVSKSPVEEKAKSPVPKSPVEEAKSKAEVGKGE

QKEEEEKEVKEAPKEEKVEKKEEKPKDVPEKKKAESPVKEEAVAEVVTIT

KSVKVHLEKETKEEGKPLQQEKEKEKAGGEGGSEEEGSDKGAKGSRKEDI

AVNGEVEGKEEVEQETKEKGSGREEEKGVVTNGLDLSPADEKKGGDKSEE

KVVVTKTVEKITSEGGDGATKYITKSVTVTQKVEEHEETFEEKLVSTKKV

EKVTSHAIVKEVTQSD

SEQ ID NO: 6
MARHLREYQDLLNVKMALDIEIAAYRKLLEGEETRFSTFAGSITGPLYTH

RPPITISSKIQKPKVEAPKLKVQHKFVEEIIEETKVEDEKSEMEEALTAI

TEELAVSMKEEKKEAAEEKEEEPEAEEEEVAAKKSPVKATAPEVKEEEGE

KEEEEGQEEEEEEDEGAKSDQAEEGGSEKEGSSEKEEGEQEEGETEAEAE

GEEAEAKEEKKVEEKSEEVATKEELVADAKVEKPEKAKSPVPKSPVEEKG

KSPVPKSPVEEKGKSPVPKSPVEEKGKSPVPKSPVEEKGKSPVSKSPVEE

KAKSPVPKSPVEEAKSKAEVGKGEQKEEEEKEVKEAPKEEKVEKKEEKPK

DVPEKKKAESPVKEEAVAEVVTITKSVKVHLEKETKEEGKPLQQEKEKEK

AGGEGGSEEEGSDKGAKGSRKEDIAVNGEVEGKEEVEQETKEKGSGREEE

KGVVTNGLDLSPADEKKGGDKSEEKVVVTKTVEKITSEGGDGATKYITKS

VTVTQKVEEHEETFEEKLVSTKKVEKVTSHAIVKEVTQSD

The amino acid sequence of human internexin is provided in SEQ ID NO:7.

SEQ ID NO: 7
MSFGSEHYLCSSSSYRKVFGDGSRLSARLSGAGGAGGFRSQSLSRSNVAS

SAACSSASSLGLGLAYRRPPASDGLDLSQAAARTNEYKIIRTNEKEQLQG

LNDRFAVFIEKVHQLETQNRALEAELAALRQRHAEPSRVGELFQRELRDL

RAQLEEASSARSQALLERDGLAEEVQRLRARCEEESRGREGAERALKAQQ

RDVDGATLARLDLEKKVESLLDELAFVRQVHDEEVAELLATLQASSQAAA

EVDVTVAKPDLTSALREIRAQYESLAAKNLQSAEEWYKSKFANLNEQAAR

STEAIRASREEIHEYRRQLQARTIEIEGLRGANESLERQILELEERHSAE

VAGYQDSIGQLENDLRNTKSEMARHLREYQDLLNVKMALDIEIAAYRKLL

EGEETRFSTSGLSISGLNPLPNPSYLLPPRILSATTSKVSSTGLSLKKEE

EEEEASKVASKKTSQIGESFEEILEETVISTKKTEKSNIEETTISSQKI

The amino acid sequence of human peripherin is provided in SEQ ID NO:8.

SEQ ID NO: 8
MSHHPSGLRAGFSSTSYRRTFGPPPSLSPGAFSYSSSSRFSSSRLLGSAS

PSSSVRLGSFRSPRAGAGALLRLPSERLDFSMAEALNQEFLATRSNEKQE

LQELNDRFANFIEKVRFLEQQNAALRGELSQARGQEPARADQLCQQELRE

LRRELELLGRERDRVQVERDGLAEDLAALKQRLEEETRKREDAEHNLVLF

RKDVDDATLSRLELERKIESLMDEIEFLKKLHEEELRDLQVSVESQQVQQ

VEVEATVKPELTAALRDIRAQYESIAAKNLQEAEEWYKSKYADLSDAANR

NHEALRQAKQEMNESRRQIQSLTCEVDGLRGTNEALLRQLRELEEQFALE

AGGYQAGAARLEEELRQLKEEMARHLREYQELLNVKMALDIEIATYRKLL

EGEESRISVPVHSFASLNIKTTVPEVEPPQDSHSRKTVLIKTIETRNGEV

VTESQKEQRSELDKSSAHSY

In certain instances, the level of NF (e.g., pNF-H) is used in combination with one or more other SMA biomarkers.

4. Diagnosing SMA

The disclosure features methods of diagnosing whether a subject (e.g., a presymptomatic subject) has biologically active disease (i.e., whether the SMA is active and its severity). The method involves measuring a neurofilament level in a biological sample obtained from the subject. SMA is diagnosed if the neurofilament level in the subject is higher than a control level. The neurofilament level also predicts the severity of the disease: the higher the NF level relative to a control the more severe the SMA.

In some instances, the method involves measuring a NF-H level in the biological sample obtained from the subject. In some instances, the method involves measuring a pNF-H level in the biological sample obtained from the subject. In some instances, the method involves measuring a NF-M level in the biological sample obtained from the subject. In some instances, the method involves measuring a NF-L level in the biological sample obtained from the subject.

The biological sample can be e.g., blood, serum, plasma, or cerebrospinal fluid. In some instances, the biological sample is plasma.

In certain instances, the subject is a human fetus. In certain instances, the subject is a human who is a new born. In certain instances, the subject is a human who is less than or equal to 6 months of age (e.g., 2 days old, 3 days old, 4 days old, 5 days old, 6 days old, 1 week old, 2 weeks old, 3 weeks old, 1 month old, 2 months old, 3 months old, 4 months old, 5 months old, or 6 months old). In certain instances, the subject is a human who is greater than 6 months of age and less than equal to 18 months of age (e.g., 7 months old, 8 months old, 9 months old, 10 months old, 11 months old, 12 months old, 13 months old, 14 months old, 15 months old, 16 months old, 17 months old, or 18 months old). In some instances, the subject is a human who is greater than 18 months of age. In some instances, the subject is a human who is greater than 18 years of age.

In some instances, the NF level is measured by assessing the level of NF RNA (e.g., mRNA) in the biological sample.

In some instances, the NF level is measured by assessing the level of an NF protein (NF-H, NF-M, or NF-L protein) in the biological sample. In certain instances, the NF protein is pNF-H. The concentration of the protein or proteins of interest can be measured using any method known in the art such as an immunological assay. Non-limiting examples of such methods include enzyme immunoassay, radioimmunoassay, chemiluminescent immunoassay, electrochemiluminescence immunoassay, latex turbidimetric immunoassay, latex photometric immunoassay, immuno-chromatographic assay, and western blotting. In certain embodiments, the concentration of the protein or proteins of interest is measured by mass spectrometry.

In some embodiments, the neurofilament level (e.g., pNF-H) in the biological sample is above a control level. In some embodiments, the neurofilament level in the biological sample is above 300 pg/mL. In some embodiments the neurofilament level in the biological sample is above 400 pg/mL. In some embodiments, the neurofilament level in the biological sample is above 500 pg/mL. In some embodiments, the neurofilament level in the biological sample is above 600 pg/mL. In some embodiments, the neurofilament level in the biological sample is above 700 pg/mL. In some embodiments, the neurofilament level in the biological sample is above 800 pg/mL. In some embodiments, the neurofilament level in the biological sample is above 900 pg/mL. In some embodiments, the neurofilament level in the biological sample is above 1,000 pg/mL. In some embodiments, the neurofilament level in the biological sample is above 1,100 pg/mL. In some embodiments, the neurofilament level in the biological sample is above 1,200 pg/mL. In some embodiments, the neurofilament level in the biological sample is above 1,300 pg/mL. In some embodiments, the neurofilament level in the biological sample is above 1,400 pg/mL. In some embodiments, the neurofilament level in the biological sample is above 1,500 pg/mL. In some embodiments, the neurofilament level in the biological sample is above 2,000 pg/mL. In some embodiments, the neurofilament level in the biological sample is above 3,000 pg/mL. In some embodiments, the neurofilament level in the biological sample is above 4,000 pg/mL. In some embodiments, the neurofilament level in the biological sample is above 5,000 pg/mL.

A human subject who is diagnosed as having SMA can be administered any SMA therapy. In certain cases, a human subject who is previously determined to have SMA (e.g., by measuring NF levels in a biological sample from the subject) is administered a SMA therapy. In some instances, the therapy is SPINRAZA®. In some cases, SPINRAZA® is administered intrathecally at a dose of 12 mg per administration. In some instances, the SMA therapy is a combination therapy.

Exemplary levels of pNF-H in subjects having SMA are provided in the table below:

| Clinical Trial | Age (days) | pNF-H Level (pg/mL) (SMN2 = 2 copies) | pNF-H Level (pg/mL) (SMN2 = 3 copies) |
|---|---|---|---|
| NURTURE | 3-42 | 1,498-52,943 | 959-7,950 |
| ENDEAR | 30-262 | 2,390-50,100 | 13,600 |

5. Responsiveness to Treatment

The levels of NF can also be used to determine if a subject receiving a SMA therapy is responding to the treatment. This can be assessed by obtaining a first biological sample from the subject before and a second biological sample after administering a SMA therapy to the subject and measuring the level of NF (e.g., NF-H, NF-M, or NF-L) in such samples. In one instance, the level of NF is a level of pNF-H. In some instances, the therapy is SPINRAZA®. In some cases, SPINRAZA® is administered intrathecally at a dose of 12 mg per administration. In some instances, the SMA therapy is a combination therapy.

In certain instances, the first biological sample or samples can be collected from the subject any time before treatment, e.g., a week before, several days before, a day before, several hours before, an hour before, or less than an hour before, administering the SMA therapy. Similarly, the second biological sample or samples can be collected from the subject any time after administration of the SMA treatment, e.g., less than an hour after, an hour after, several hours after, a day after, several days after, a week after, several weeks after, a month after, two months after, three months after, four months after, five months after, 6 months after, 7 months after, or 8 months after, administering the SMA therapy. A reduction in NF level after commencing SMA therapy is indicative of the effectiveness of the SMA therapy. In such instances, continuation of the SMA therapy is indicated. Failure to reduce NF level after commencing an SMA therapy is indicative of the need for altering the dose (e.g., increasing the dose) of the SMA therapy, or the lack of effectiveness of that particular SMA therapy. In the latter instance, discontinuation of that particular SMA therapy may be suggested and the use of a different SMA therapy or therapies is to be considered.

The level of NF can be assessed by measuring RNA or protein levels. In some instances, the level of pNF-H is determined. The concentration of the NF protein or proteins of interest can be measured using any method known in the art such as an immunological assay. Non-limiting examples of such methods include enzyme immunoassay, radioimmunoassay, chemiluminescent immunoassay, electrochemiluminescence immunoassay, latex turbidimetric immunoassay, latex photometric immunoassay, immuno-chromatographic assay, and western blotting. In certain embodiments, the concentration of the protein or proteins of interest is measured by mass spectrometry.

In certain instances, a neurofilament level (e.g., pNF-H) in the first biological sample is above 300 pg/mL, above 400 pg/mL, above 500 pg/mL, above 600 pg/mL, above 700 pg/mL, above 800 pg/mL, above 900 pg/mL, above 1,000 pg/mL, above 1,500 pg/mL, above 2,000 pg/mL, above 3,000 pg/mL, above 4,000 pg/mL, or above 5,000 pg/mL. In certain embodiments, the neurofilament level measured in the second biological sample is lower than the neurofilament level measured in the first biological sample. In some embodiments, the neurofilament level measured in the second biological sample shows a greater than 30% (e.g., greater than 31%, 35%, 40%, 45%, 50%, 55%, 60%, 65%, 70%, 80%, 85%, 90%, or 95%) decline relative to the neurofilament level measured in the first biological sample. In some embodiments, the neurofilament level measured in the second biological sample is between 10% to 80% of the neurofilament level measured in the first biological sample. In some embodiments, the neurofilament level measured in the second biological sample is between 20% to 80% of the neurofilament level measured in the first biological sample. In some embodiments, the neurofilament level measured in the second biological sample is between 20% to 85% of the neurofilament level measured in the first biological sample. In some embodiments, the neurofilament level measured in the second biological sample is between 20% to 90% of the neurofilament level measured in the first biological sample. In some embodiments, the neurofilament level measured in the second biological sample is between 20% to 95% of the neurofilament level measured in the first biological sample. In some embodiments, the neurofilament level measured in the second biological sample is between 30% to 80% of the neurofilament level measured in the first biological sample. In some embodiments, the neurofilament level measured in the second biological sample is between 30% to 85% of the neurofilament level measured in the first biological sample. In some embodiments, the neurofilament level measured in the second biological sample is between 30% to 90% of the neurofilament level measured in the first biological sample. In some embodiments, the neurofilament level measured in the second biological sample is between 30% to 95% of the neurofilament level measured in the first biological sample.

In certain instances, the subject is a presymptomatic human. In certain instances, the subject is a human who is a new born. In certain instances, the subject is a human who is less than or equal to 6 months of age (e.g., 2 days old, 3 days old, 4 days old, 5 days old, 6 days old, 1 week old, 2 weeks old, 3 weeks old, 1 month old, 2 months old, 3 months old, 4 months old, 5 months old, or 6 months old). In certain instances, the subject is a human who is greater than 6 months of age and less than equal to 18 months of age (e.g., 7 months old, 8 months old, 9 months old, 10 months old, 11 months old, 12 months old, 13 months old, 14 months old, 15 months old, 16 months old, 17 months old, or 18 months old). In some instances, the subject is a human who is greater than 18 months of age. In some instances, the subject is a human who is greater than 18 years of age.

6. Predicting Disease Progression

The levels of NF in a biological sample from a subject can also serve to predict future phenotypes. For example, the level of NF can predict future motor function. As an illustration, the level of pNF-H one to two months after commencement of therapy can predict motor function ten months after commencement of therapy. The lower the pNF-H level one to two months after commencement of therapy relative to a control, the more likely the subject will have improved motor function relative to a subject with higher pNF-H levels one to two months after commencement of therapy. This predictive possibility allows the healthcare practitioner to modify or adjust dosing and treatment of the subject.

7. Controls

As described above, the methods of the present disclosure can involve, measuring the expression level (e.g., mRNA or protein concentration) of one or more NF genes or proteins in a biological sample from a subject (e.g., a presymptomatic human subject), wherein the expression level of one or more of the NF genes or proteins, compared to a control, predicts whether a subject has SMA; the severity of the SMA; future phenotypes; and whether or not a subject is a responder to treatment comprising a SMA therapy (e.g., SPINRAZA®).

In certain embodiments, when diagnosing whether a subject has SMA, where the concentration of a NF protein (e.g., pNF-H) in a biological sample from a subject is higher than the control, the subject is identified as likely to have SMA. In this context, the term "control" includes a sample (from the same source—e.g., blood, plasma, serum, CSF) obtained from a subject of the same or similar age who is known to not have SMA. For example, if a subject who is a newborn is being tested, then the control is also from a newborn who does not have SMA; if a subject who is 6-18 months of age is being tested, then the control is also from a subject who is 6-18 months in age who do not have SMA. The term "control" also includes a sample (from the same tissue) obtained in the past from a subject who is known to not have SMA and used as a reference for future comparisons to test samples taken from subjects for whom SMA is to be predicted. The "control" expression level/concentration for a particular NF protein may also be pre-established by an analysis of protein expression in one or more (e.g., two, three, four, five, six, seven, eight, nine, 10, 15, 20, 25, 30, 35, or 40 or more) human subjects of similar age that do not have SMA. This pre-established reference value (which may be an average or median expression level/concentration taken from multiple subjects that do not have SMA) may then be used for the "control" concentration/expression level of the protein or nucleic acid in the comparison with the test sample. In such a comparison, the subject is predicted to have SMA if the expression level of the NF being analyzed is higher than the pre-established reference.

The methods of the present disclosure can involve, measuring the expression level (e.g., mRNA or protein concentration) of one or more genes (e.g., one or more NF genes) in a biological sample from a subject having or suspected of having SMA, wherein the expression level of one or more of the NF genes, compared to a control, predicts the responsiveness of a subject to treatment comprising a SMA therapy (e.g., SPINRAZA®). In certain embodiments, when the concentration of a NF protein (e.g., pNF-H) in a biological sample from a subject having or suspected of having SMA is lower than the control, the subject is identified as likely to respond to a therapy comprising a SMA therapy. In this context, the term "control" includes a sample (from the same source—e.g., plasma, blood, serum, CSF) obtained from a subject of the same or similar age who is known to not respond to that SMA therapy. The term "control" also includes a sample (from the same tissue) obtained in the past from a subject who is known to not respond to that SMA therapy and used as a reference for future comparisons to test samples taken from subjects for which therapeutic responsiveness is to be predicted. The "control" expression level/concentration for a particular NF protein in a particular cell type or tissue may be pre-established by an analysis of protein expression in one or more (e.g., two, three, four, five, six, seven, eight, nine, 10, 15, 20, 25, 30, 35, or 40 or more) human subjects of the same or similar age that have not responded to treatment with a SMA therapy (e.g., SPINRAZA®). This pre-established reference value (which may be an average or median expression level/concentration taken from multiple subjects that have not responded to the therapy) may then be used for the "control" concentration/ expression level of the protein or nucleic acid in the comparison with the test sample. In such a comparison, the subject is predicted to respond to a therapy comprising a SMA therapy (e.g., SPINRAZA®) if the expression level of the NF gene being analyzed is lower than the pre-established reference.

The "control" concentration for a particular protein (e.g., NF-H) in a particular biological fluid, cell type, or tissue may alternatively be pre-established by an analysis of gene expression in one or more subjects that have responded to treatment with a SMA therapy (e.g., SPINRAZA®). This pre-established reference value (which may be an average or median expression level taken from multiple subjects that have responded to the therapy) may then be used as the "control" expression level in the comparison with the test sample. In such a comparison, the subject is predicted to respond to a SMA therapy (e.g., SPINRAZA®) if the concentration of the protein being analyzed is the same as, or comparable to (at least 85% but less than 100% of), the pre-established reference.

In certain embodiments, the "control" is a pre-determined cut-off value.

In some embodiments, the methods described herein include determining if the concentration of a NF protein(s) of interest falls above or below a predetermined cut-off value.

A cut-off value is typically a concentration of a protein above or below which is considered predictive of something—e.g., likely to develop SMA; or responsiveness of a subject to a therapy of interest. Thus, in accordance with the methods described herein, a reference concentration of a NF protein (e.g., pNF-H) is identified as a cut-off value, above or below of which is predictive of a subject having SMA, or of a subject who shows responsiveness to a SMA therapy (e.g., SPINRAZA®). Some cut-off values are not absolute in that clinical correlations can still remain significant over a range of values on either side of the cutoff; however, it is possible to select an optimal cut-off value (e.g. varying H-scores) of concentration of NF proteins for a particular sample type. Cut-off values determined for use in the methods described herein can be compared with, e.g., published ranges of NF concentrations, but can be individualized to the methodology used and patient population. It is understood that improvements in optimal cut-off values could be determined depending on the sophistication of statistical methods used and on the number and source of samples used to determine reference level values for the different proteins, genes, and sample types. Therefore, established cut-off values can be adjusted up or down, on the basis of periodic re-evaluations or changes in methodology or population distribution.

The reference concentration of one or more NF proteins can be determined by a variety of methods. The reference level can be determined by comparison of the concentration of a NF protein of interest in, e.g., populations of subjects (e.g., patients) that are responsive to a SMA therapy (e.g., SPINRAZA®) or not responsive to a SMA therapy. This can be accomplished, for example, by histogram analysis, in which an entire cohort of patients is graphically presented, wherein a first axis represents the concentration of a protein of interest and a second axis represents the number of subjects in the cohort whose sample contain one or more concentrations. Determination of the reference concentration of a protein can then be made based on an amount or concentration which best distinguishes these separate groups. The reference level can be a single number, equally applicable to every subject, or the reference level can vary, according to specific subpopulations of subjects. For example, older subjects can have a different reference level than younger subjects. In addition, a subject with more severe disease can have a different reference value than one with a milder form of the disease (e.g., Type I vs. Type IV SMA; Type I vs. Type III SMA; Type I vs. Type II SMA).

The pre-established cut-off value can be a NF protein concentration (e.g., pNF-H) that is determined based on receiver operating characteristic (ROC) analysis. ROC curves are used to determine a cut-off value for a clinical test. Consider the situation where there are two groups of patients and by using an established standard technique one group is known to be responsive to a SMA therapy, and the other is known to not respond to the SMA therapy. A measurement using a biological sample from all members of the two groups is used to test for responsiveness to a SMA therapy. The test will find some, but not all, responders to respond to a SMA therapy. The ratio of the responders found by the test to the total number of responders (known by the established standard technique) is the true positive rate (also known as sensitivity). The test will find some, but not all, non-responders to not respond to a SMA therapy. The ratio of the non-responders found by the test to the total number of non-responders (known by the established standard technique) is the true negative rate (also known as specificity). The hope is that the ROC curve analysis of the SMA therapy-responsiveness test will find a cut-off value that will minimize the number of false positives and false negatives. A ROC is a graphical plot which illustrates the performance of a binary class stratifier system as its discrimination threshold is varied. It is created by plotting the fraction of true positives out of the positives versus the fraction of false positives out of the negatives, at various threshold settings.

In one embodiment, the NF protein concentration is determined based on ROC analysis predicting response to a SMA therapy with a positive predictive value, wherein a concentration of a protein of interest (e.g., pNF-H) equal to or below the pre-established cut-off value is a low concentration of the protein of interest and a value higher than the pre-established cut-off value is a high concentration of the protein of interest. The positive predictive value is the proportion of positive test results that are true positives; it reflects the probability that a positive test reflects the underlying condition being tested for. Methods of constructing ROC curves and determining positive predictive values are well known in the art.

In another embodiment, the pre-established cut-off value can be a NF protein concentration that is determined based on simulation models predicting responsiveness to SMA therapy, and wherein a concentration of the protein of interest (e.g., pNF-H) equal to or below the pre-established cut-off value is a low concentration of the protein of interest and a value higher than the pre-established cut-off value is a high concentration of the protein of interest.

8. Biological Samples

Suitable biological samples for the methods described herein include any biological fluid, cell, tissue, or fraction thereof, which includes analyte biomolecules of interest such as NF protein or nucleic acid (e.g., RNA (mRNA)). A biological sample can be, for example, a specimen obtained from a human subject or can be derived from such a subject. For example, a sample can be a tissue section obtained by biopsy, archived biological fluid, or cells that are placed in or adapted to tissue culture. In some instances, a biological sample is a biological fluid such as blood, plasma, serum, cerebrospinal fluid (CSF), urine, or such a sample absorbed onto a substrate (e.g., glass, polymer, paper). A biological sample can be further fractionated, if desired, to a fraction containing particular cell types. For example, a blood sample can be fractionated into serum or into fractions containing particular types of blood cells such as red blood cells or white blood cells (leukocytes). If desired, a sample can be a combination of samples from a subject such as a combination of a tissue and fluid sample.

The biological samples can be obtained from a subject having, suspected of having, or at risk of developing, SMA. In certain embodiments, the subject is a human fetus. In certain embodiments, the subject is a presymptomatic human infant. In certain embodiments, the subject is a presymptomatic human child. In certain embodiments, the subject is a presymptomatic human adult.

Any suitable methods for obtaining the biological samples can be employed, although exemplary methods include, e.g., phlebotomy, fine needle aspirate biopsy procedure. Samples can also be collected, e.g., by microdissection (e.g., laser capture microdissection (LCM) or laser microdissection (LMD)).

Methods for obtaining and/or storing samples that preserve the activity or integrity of molecules (e.g., nucleic acids or proteins) in the sample are well known to those skilled in the art. For example, a biological sample can be further contacted with one or more additional agents such as buffers and/or inhibitors, including one or more of nuclease, protease, and phosphatase inhibitors, which preserve or minimize changes in the molecules (e.g., nucleic acids or proteins) in the sample. Such inhibitors include, for example, chelators such as ethylenediamine tetraacetic acid (EDTA), ethylene glycol bis(P-aminoethyl ether) N,N,N1,N1-tetraacetic acid (EGTA), protease inhibitors such as phenylmethylsulfonyl fluoride (PMSF), aprotinin, leupeptin, antipain, and the like, and phosphatase inhibitors such as phosphate, sodium fluoride, vanadate, and the like. Suitable buffers and conditions for isolating molecules are well known to those skilled in the art and can be varied depending, for example, on the type of molecule in the sample to be characterized (see, e.g., Ausubel et al. Current Protocols in Molecular Biology (Supplement 47), John Wiley & Sons, New York (1999); Harlow and Lane, Antibodies: A Laboratory Manual (Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999)). A sample also can be processed to eliminate or minimize the presence of interfering substances. For example, a biological sample can be fractionated or purified to remove one or more materials that are not of interest. Methods of fractionating or purifying a biological sample include, but are not limited to, chromatographic methods such as liquid chromatography, ion-exchange chromatography, size-exclusion chromatography, or affinity chromatography. For use in the methods described herein, a sample can be in a variety of physical states. For example, a sample can be a liquid or solid, can be dissolved or suspended in a liquid, can be in an emulsion or gel, or can be absorbed onto a material.

9. Determining Expression Levels/Concentrations of Biomarkers

Gene expression can be detected as, e.g., protein or RNA expression of a target gene. That is, the presence or expression level (amount) of a gene can be determined by detecting and/or measuring the level of mRNA or protein expression of the gene. In some embodiments, gene expression can be detected as the activity of a protein encoded by a NF gene.

In one embodiment, the expression of a gene can be determined by detecting and/or measuring expression or concentration of a protein encoded by the gene. Methods of determining protein expression/concentration are well known in the art. A generally used method involves the use of antibodies specific for the target protein of interest. For example, methods of determining protein expression include, but are not limited to, western blot or dot blot analysis, immunohistochemistry (e.g., quantitative immunohistochemistry), immunocytochemistry, enzyme-linked immunosorbent assay (ELISA), enzyme-linked immunosorbent spot (ELISPOT; Coligan, J. E., et al., eds. (1995) Current Protocols in Immunology. Wiley, New York), radioimmunoassay, chemiluminescent immunoassay, electrochemiluminescence immunoassay, latex turbidimetric immunoassay, latex photometric immunoassay, immunochromatographic assay, and antibody array analysis (see, e.g., U.S. Publication Nos. 2003/0013208 and 2004/171068, the disclosures of each of which are incorporated herein by reference in their entirety). Further description of many of the methods above and additional methods for detecting protein expression can be found in, e.g., Sambrook et al. (supra).

In one example, the presence or amount of NF protein expression of a NF gene (e.g., NF-H) can be determined using a western blotting technique. For example, a lysate can be prepared from a biological sample, or the biological sample itself, can be contacted with Laemmli buffer and subjected to sodium-dodecyl sulfate polyacrylamide gel electrophoresis (SDS-PAGE). SDS-PAGE-resolved proteins, separated by size, can then be transferred to a filter membrane (e.g., nitrocellulose) and subjected to immunoblotting techniques using a detectably-labeled antibody specific to the protein of interest. The presence or amount of bound detectably-labeled antibody indicates the presence or amount of protein in the biological sample.

In one embodiment, the SimplePlex platform is used to measure the levels of NF-H (e.g., phosphorylated NF-H). SimplePlex is commercially available from Protein Simple (San Jose, Calif., USA) (See Dysinger M, et al. J. Immunol. Methods. 451:1-10, 2017).

In one embodiment, an assay for measuring NF-L (e.g., phosphorylated NF-L) is employed. Assays for measuring NF-L in serum have been described (see, e.g., Gaiottino et al., PLoS ONE 8: e75091, 2013; Kuhle et al., J. Neurol. Neurosurg. Psychiatry 86(3): 273-279, 2014). In one example, blood serum from a subject is centrifuged at 1000 g for 10 minutes at room temperature and stored at −80° C. within 2 hours of collection. Serum NF-L concentrations can be measured (e.g., in duplicate) using ready-to-use enzyme linked immunosorbent assay (ELISA) (Mabtech AB, Nacka Strand, Sweden) or an electrochemiluminescence (ECL) immunoassay described in Gaiottino et al., PLoS ONE 8: e75091, 2013, or a single molecule array (SIMOA) method described in Disanto et al., Ann. Neurol. 81(6): 857-870, 2017. The assay methods have been compared in Kuhl et al., Clinical Chemistry and Laboratory Medicine 54 (10): 1655-1661, 2016. The SIMOA assay (particularly called the Simoa NF-light Advantage kit) is commercially available from Quanterix Corp. (Lexington, Mass., USA).

In another example, an immunoassay can be used for detecting and/or measuring the protein expression of a gene (e.g., NF-H gene). As above, for the purposes of detection, an immunoassay can be performed with an antibody that bears a detection moiety (e.g., a fluorescent agent or enzyme). Proteins from a biological sample can be conjugated directly to a solid-phase matrix (e.g., a multi-well assay plate, nitrocellulose, agarose, sepharose, encoded particles, or magnetic beads) or it can be conjugated to a first member of a specific binding pair (e.g., biotin or streptavidin) that attaches to a solid-phase matrix upon binding to a second member of the specific binding pair (e.g., streptavidin or biotin). Such attachment to a solid-phase matrix allows the proteins to be purified away from other interfering or irrelevant components of the biological sample prior to contact with the detection antibody and also allows for subsequent washing of unbound antibody. Here, as above, the presence or amount of bound detectably-labeled antibody indicates the presence or amount of protein in the biological sample.

There is no particular restriction as to the form of the antibody and the present disclosure includes polyclonal antibodies, as well as monoclonal antibodies. The antiserum obtained by immunizing animals, such as rabbits with a protein or fragment thereof of the invention (i.e., a protein or an immunological fragment thereof of a NF protein), as well polyclonal and monoclonal antibodies of all classes, human antibodies, and humanized antibodies produced by genetic recombination, are also included.

An intact protein or its partial peptide may be used as the antigen for immunization. As partial peptides of the proteins, for example, the amino (N)-terminal fragment of the protein and the carboxy (C)-terminal fragment can be given.

A gene encoding a protein of interest or a fragment thereof (e.g., an immunological fragment) is inserted into a known expression vector, and, by transforming the host cells with the vector described herein, the desired protein or a fragment thereof is recovered from outside or inside the host cells using standard methods. This protein can be used as the sensitizing antigen. Also, cells expressing the protein, cell lysates, or a chemically synthesized protein of the invention may be also used as a sensitizing antigen.

The mammal that is immunized by the sensitizing antigen is not restricted; however, it is preferable to select animals by considering the compatibility with the parent cells used in cell fusion. Generally, animals belonging to the orders rodentia, lagomorpha, or primates are used. Examples of animals belonging to the order of rodentia that may be used include, for example, mice, rats, and hamsters. Examples of animals belonging to the order of lagomorpha that may be used include, for example, rabbits. Examples of animals belonging to the order of primates that may be used include, for example, monkeys. Examples of monkeys to be used include the infraorder catarrhini (old world monkeys), for example, *Macaca fascicularis*, rhesus monkeys, sacred baboons, and chimpanzees.

Well-known methods may be used to immunize animals with the sensitizing antigen. For example, the sensitizing antigen is injected intraperitoneally or subcutaneously into mammals. Specifically, the sensitizing antigen is suitably diluted and suspended in physiological saline, phosphate-buffered saline (PBS), and so on, and mixed with a suitable amount of general adjuvant if desired, for example, with Freund's complete adjuvant. Then, the solution is emulsified and injected into the mammal. Thereafter, the sensitizing antigen suitably mixed with Freund's incomplete adjuvant is preferably given several times every 4 to 21 days. A suitable carrier can also be used when immunizing and animal with the sensitizing antigen. After the immunization, the elevation in the level of serum antibody is detected by usual methods.

Polyclonal antibodies against the proteins of the present disclosure can be prepared as follows. After verifying that the desired serum antibody level has been reached, blood is withdrawn from the mammal sensitized with antigen. Serum is isolated from this blood using conventional methods. The serum containing the polyclonal antibody may be used as the polyclonal antibody, or according to needs, the polyclonal antibody-containing fraction may be further isolated from the serum. For example, a fraction of antibodies that specifically recognize the protein of the invention may be prepared by using an affinity column to which the protein is coupled. Then, the fraction may be further purified by using a Protein A or Protein G column in order to prepare immunoglobulin G or M.

To obtain monoclonal antibodies, after verifying that the desired serum antibody level has been reached in the mammal sensitized with the above-described antigen, immunocytes are taken from the mammal and used for cell fusion. For this purpose, splenocytes can be mentioned as preferable immunocytes. As parent cells fused with the above immunocytes, mammalian myeloma cells are preferably used. More preferably, myeloma cells that have acquired the feature, which can be used to distinguish fusion cells by agents, are used as the parent cell.

The cell fusion between the above immunocytes and myeloma cells can be conducted according to known methods, for example, the method by Milstein et al. (Galfre et al., *Methods Enzymol.* 73:3-46, 1981).

The hybridoma obtained from cell fusion is selected by culturing the cells in a standard selection medium, for example, HAT culture medium (medium containing hypoxanthine, aminopterin, and thymidine). The culture in this HAT medium is continued for a period sufficient enough for cells (non-fusion cells) other than the objective hybridoma to perish, usually from a few days to a few weeks. Then, the usual limiting dilution method is carried out, and the hybridoma producing the objective antibody is screened and cloned.

Other than the above method for obtaining hybridomas, by immunizing an animal other than humans with the antigen, a hybridoma producing the objective human antibodies having the activity to bind to proteins can be obtained by the method of sensitizing human lymphocytes, for example, human lymphocytes infected with the EB virus, with proteins, protein-expressing cells, or lysates thereof in vitro and fusing the sensitized lymphocytes with myeloma cells derived from human, for example, U266, having a permanent cell division ability.

The monoclonal antibodies obtained by transplanting the obtained hybridomas into the abdominal cavity of a mouse and extracting ascites can be purified by, for example, ammonium sulfate precipitation, protein A or protein G column, DEAE ion exchange chromatography, an affinity column to which the protein of the present disclosure is coupled, and so on.

Monoclonal antibodies can be also obtained as recombinant antibodies produced by using the genetic engineering technique (see, for example, Borrebaeck C. A. K. and Larrick, J. W., THERAPEUTIC MONOCLONAL ANTIBODIES, Published in the United Kingdom by MACMILLAN PUBLISHERS LTD (1990)). Recombinant antibodies are produced by cloning the encoding DNA from immunocytes, such as hybridoma or antibody-producing sensitized lymphocytes, incorporating into a suitable vector, and introducing this vector into a host to produce the antibody. The present disclosure encompasses such recombinant antibodies as well.

Antibodies or antibody fragments specific for a protein encoded by one or more biomarkers can also be generated by in vitro methods such as phage display.

Moreover, the antibody of the present disclosure may be an antibody fragment or modified-antibody, so long as it binds to a protein encoded by a biomarker of the invention. For instance, Fab, F (ab') 2, Fv, or single chain Fv (scFv) in which the H chain Fv and the L chain Fv are suitably linked by a linker (Huston et al., *Proc. Natl. Acad. Sci. USA,*

85:5879-5883, (1988)) can be given as antibody fragments. Specifically, antibody fragments are generated by treating antibodies with enzymes, for example, papain or pepsin. Alternatively, they may be generated by constructing a gene encoding an antibody fragment, introducing this into an expression vector, and expressing this vector in suitable host cells (see, for example, Co et al., *J. Immunol.*, 152:2968-2976, 1994; Better et al., *Methods Enzymol.*, 178:476-496, 1989; Pluckthun et al., *Methods Enzymol.*, 178:497-515, 1989; Lamoyi, *Methods Enzymol.*, 121:652-663, 1986; Rousseaux et al., *Methods Enzymol.*, 121:663-669, 1986; Bird et al., *Trends Biotechnol.*, 9:132-137, 1991).

The antibodies may be conjugated to various molecules, such as fluorescent substances, radioactive substances, and luminescent substances. Methods to attach such moieties to an antibody are already established and conventional in the field (see, e.g., U.S. Pat. Nos. 5,057,313 and 5,156,840).

Examples of methods that assay the antigen-binding activity of the antibodies include, for example, measurement of absorbance, enzyme-linked immunosorbent assay (ELISA), enzyme immunoassay (EIA), radioimmunoassay (RIA), and/or immunofluorescence. For example, when using ELISA, a protein encoded by a biomarker of the invention is added to a plate coated with the antibodies of the present disclosure, and then, the antibody sample, for example, culture supernatants of antibody-producing cells, or purified antibodies are added. Then, secondary antibody recognizing the primary antibody, which is labeled by alkaline phosphatase and such enzymes, is added, the plate is incubated and washed, and the absorbance is measured to evaluate the antigen-binding activity after adding an enzyme substrate such as p-nitrophenyl phosphate. As the protein, a protein fragment, for example, a fragment comprising a C-terminus, or a fragment comprising an N-terminus may be used. To evaluate the activity of the antibody of the invention, BIAcore (Pharmacia) may be used.

By using these methods, the antibody of the invention and a sample presumed to contain a protein of the invention are contacted, and the protein encoded by a biomarker of the invention is detected or assayed by detecting or assaying the immune complex formed between the above-mentioned antibody and the protein.

Mass spectrometry based quantitation assay methods, for example, but not limited to, multiple reaction monitoring (MRM)-based approaches in combination with stable-isotope labeled internal standards, are an alternative to immunoassays for quantitative measurement of proteins. These approaches do not require the use of antibodies and so the analysis can be performed in a cost- and time-efficient manner (see, for example, Addona et al., *Nat. Biotechnol.*, 27:633-641, 2009; Kuzyk et al., *Mol. Cell Proteomics*, 8:1860-1877, 2009; Paulovich et al., *Proteomics Clin. Appl.*, 2:1386-1402, 2008). In addition, MRM offers superior multiplexing capabilities, allowing for the simultaneous quantification of numerous proteins in parallel. The basic theory of these methods has been well-established and widely utilized for drug metabolism and pharmacokinetics analysis of small molecules.

In another embodiment, the expression level of a NF gene of interest is determined by measuring RNA levels. A variety of suitable methods can be employed to detect and/or measure the level of mRNA expression of a gene. For example, mRNA expression can be determined using Northern blot or dot blot analysis, reverse transcriptase-PCR (RT-PCR; e.g., quantitative RT-PCR), in situ hybridization (e.g., quantitative in situ hybridization) or nucleic acid array (e.g., oligonucleotide arrays or gene chips) analysis. Details of such methods are described below and in, e.g., Sambrook et al., *Molecular Cloning: A Laboratory Manual* Second Edition vol. 1, 2 and 3. Cold Spring Harbor Laboratory Press: Cold Spring Harbor, N.Y., USA, November 1989; Gibson et al. (1999) *Genome Res.*, 6(10):995-1001; and Zhang et al. (2005) *Environ. Sci. Technol.*, 39(8):2777-2785; U.S. Publication No. 2004086915; European Patent No. 0543942; and U.S. Pat. No. 7,101,663; the disclosures of each of which are incorporated herein by reference in their entirety.

In one example, the presence or amount of one or more discrete mRNA populations in a biological sample can be determined by isolating total mRNA from the biological sample (see, e.g., Sambrook et al. (supra) and U.S. Pat. No. 6,812,341) and subjecting the isolated mRNA to agarose gel electrophoresis to separate the mRNA by size. The size-separated mRNAs are then transferred (e.g., by diffusion) to a solid support such as a nitrocellulose membrane. The presence or amount of one or more mRNA populations in the biological sample can then be determined using one or more detectably-labeled-polynucleotide probes, complementary to the mRNA sequence of interest, which bind to and thus render detectable their corresponding mRNA populations. Detectable-labels include, e.g., fluorescent (e.g., umbelliferone, fluorescein, fluorescein isothiocyanate, rhodamine, dichlorotriazinylamine fluorescein, dansyl chloride, allophycocyanin (APC), or phycoerythrin), luminescent (e.g., europium, terbium, Qdot™ nanoparticles supplied by the Quantum Dot Corporation, Palo Alto, Calif.), radiological (e.g., $^{125}I$, $^{131}I$, $^{35}S$, $^{32}P$, $^{33}P$, or $^{3}H$), and enzymatic (horseradish peroxidase, alkaline phosphatase, beta-galactosidase, or acetylcholinesterase) labels.

In another example, the presence or amount of discrete populations of mRNA (e.g., mRNA encoded by one or more NF genes) in a biological sample can be determined using nucleic acid (or oligonucleotide) arrays. For example, isolated mRNA from a biological sample can be amplified using RT-PCR with, e.g., random hexamer or oligo(dT)-primer mediated first strand synthesis. The amplicons can be fragmented into shorter segments. The RT-PCR step can be used to detectably-label the amplicons, or, optionally, the amplicons can be detectably-labeled subsequent to the RT-PCR step. For example, the detectable-label can be enzymatically (e.g., by nick-translation or kinase such as T4 polynucleotide kinase) or chemically conjugated to the amplicons using any of a variety of suitable techniques (see, e.g., Sambrook et al., supra). The detectably-labeled-amplicons are then contacted with a plurality of polynucleotide probe sets, each set containing one or more of a polynucleotide (e.g., an oligonucleotide) probe specific for (and capable of binding to) a corresponding amplicon, and where the plurality contains many probe sets each corresponding to a different amplicon. Generally, the probe sets are bound to a solid support and the position of each probe set is predetermined on the solid support. The binding of a detectably-labeled amplicon to a corresponding probe of a probe set indicates the presence or amount of a target mRNA in the biological sample. Additional methods for detecting mRNA expression using nucleic acid arrays are described in, e.g., U.S. Pat. Nos. 5,445,934; 6,027,880; 6,057,100; 6,156,501; 6,261,776; and 6,576,424; the disclosures of each of which are incorporated herein by reference in their entirety.

Methods of detecting and/or for quantifying a detectable label depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Methods for detecting or measuring gene expression (e.g., protein or mRNA expression) can optionally be performed in formats that allow for rapid preparation, processing, and analysis of multiple samples. This can be, for example, in multi-welled assay plates (e.g., 96 wells or 386 wells) or arrays (e.g., nucleic acid chips or protein chips). Stock solutions for various reagents can be provided manually or robotically, and subsequent sample preparation (e.g., RT-PCR, labeling, or cell fixation), pipetting, diluting, mixing, distribution, washing, incubating (e.g., hybridization), sample readout, data collection (optical data) and/or analysis (computer aided image analysis) can be done robotically using commercially available analysis software, robotics, and detection instrumentation capable of detecting the signal generated from the assay. Examples of such detectors include, but are not limited to, spectrophotometers, luminometers, fluorimeters, and devices that measure radioisotope decay. Exemplary high-throughput cell-based assays (e.g., detecting the presence or level of a target protein in a cell) can utilize ArrayScan® VTI HCS Reader or KineticScan® HCS Reader technology (Cellomics Inc., Pittsburgh, Pa.).

In some embodiments, the expression level of one NF gene, two NF genes, or three NF genes can be assessed and/or measured.

To aid in detecting the presence or level of expression of one or more of the NF genes, any part of the nucleic acid sequence of the genes can be used, e.g., as hybridization polynucleotide probes or primers (e.g., for amplification or reverse transcription). The probes and primers can be oligonucleotides of sufficient length to provide specific hybridization to an RNA, DNA, cDNA, or fragments thereof isolated from a biological sample. Depending on the specific application, varying hybridization conditions can be employed to achieve varying degrees of selectivity of a probe or primer towards target sequence. The primers and probes can be detectably-labeled with reagents that facilitate detection (e.g., fluorescent labels, chemical labels (see, e.g., U.S. Pat. Nos. 4,582,789 and 4,563,417), or modified bases).

Standard stringency conditions are described by Sambrook, et al. (supra) and Haymes, et al. Nucleic Acid Hybridization, A Practical Approach, IRL Press, Washington, D.C. (1985). In order for a nucleic acid molecule to serve as a primer or probe it need only be sufficiently complementary in sequence to be able to form a stable double-stranded structure under the particular hybridization conditions (e.g., solvent and salt concentrations) employed.

Hybridization can be used to assess homology between two nucleic acid sequences. A nucleic acid sequence described herein, or a fragment thereof, can be used as a hybridization probe according to standard hybridization techniques. The hybridization of a probe of interest (e.g., a probe containing a portion of a nucleotide sequence described herein or its complement) to DNA, RNA, cDNA, or fragments thereof from a test source is an indication of the presence of DNA or RNA corresponding to the probe in the test source. Hybridization conditions are known to those skilled in the art and can be found in Current Protocols in Molecular Biology, John Wiley & Sons, N.Y., 6.3.1-6.3.6, 1991. Moderate hybridization conditions are defined as hybridization in 2× sodium chloride/sodium citrate (SSC) at 30° C., followed by a wash in 1×SSC, 0.1% SDS at 50° C. Highly stringent conditions are defined as hybridization in 6×SSC at 45° C., followed by a wash in 0.2×SSC, 0.1% SDS at 65° C.

Primers can be used in a variety of PCR-type methods. For example, polymerase chain reaction (PCR) techniques can be used to amplify specific sequences from DNA as well as RNA, including sequences from total genomic DNA or total cellular RNA. The PCR primers are designed to flank the region that one is interested in amplifying. Primers can be located near the 5' end, the 3' end or anywhere within the nucleotide sequence that is to be amplified. The amplicon length is dictated by the experimental goals. For qPCR, the target length is closer to 100 base pairs and for standard PCR, it is near 500 base pairs. Generally, sequence information from the ends of the region of interest or beyond is employed to design oligonucleotide primers that are identical or similar in sequence to opposite strands of the template to be amplified. PCR primers can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair.

In addition, the nucleic acid sequences or fragments thereof (e.g., oligonucleotide probes) can be used in nucleic acid arrays for detection and/or quantitation of gene expression.

10. Methods of Treatment

The methods disclosed herein enable the assessment of whether or not a subject having or suspected of having SMA is likely to respond to a SMA therapy (e.g., SPINRAZA®). A subject having or suspected of having SMA who is likely to respond to the SMA therapy can be administered the SMA therapy (e.g., SPINRAZA®). Conversely, a subject having or suspected of having SMA who is not likely to respond to a SMA therapy can be administered a different SMA therapy that is suitable for treatment of SMA.

The methods of this disclosure also enable the stratification of subjects having or suspected of having SMA into groups of subjects that are more likely to benefit, and groups of subjects that are less likely to benefit, from treatment comprising a SMA therapy (e.g., SPINRAZA®). The ability to select such subjects from a pool of SMA subjects who are being considered for treatment with a SMA therapy is beneficial for administering an effective treatment to the subject.

The subjects who are considered for treatment comprising a SMA therapy include, but are not limited to, subjects having, suspected of having, or likely to develop SMA. In one embodiment, the subject to be treated with an SMA therapy has, is suspected of having, or is likely to develop Type 0 SMA. In one embodiment, the subject to be treated with an SMA therapy has, is suspected of having, or is likely to develop Type I SMA. In one embodiment, the subject to be treated with an SMA therapy has, is suspected of having, or is likely to develop Type II SMA. In one embodiment, the subject to be treated with an SMA therapy has, is suspected of having, or is likely to develop Type III SMA. In one embodiment, the subject to be treated with an SMA therapy has, is suspected of having, or is likely to develop Type IV SMA.

If the subject having SMA is more likely to respond to a SMA therapy (based on concentrations of one or more of the biomarkers described above (e.g., pNF-H protein)), the subject can then be administered an effective amount of the SMA therapy (e.g., SPINRAZA®). An effective amount of the compound can suitably be determined by a health care practitioner taking into account, for example, the characteristics of the patient (age, sex, weight, race, etc.), the progression of the disease, and prior exposure to the drug. If the subject is less likely to respond to one SMA therapy, the subject can then be optionally administered a different SMA therapy.

Subjects of all ages can be affected by SMA. Therefore, a biological sample used in a method described herein can be obtained from a human subject of any age, including a fetus, an infant, a child, an adolescent, or an adult, such as an adult having, or suspected of having, SMA.

The methods can also be applied to individuals at risk of developing SMA treatable by a SMA therapy (e.g., SPINRAZA®). Such individuals include those who have (i) a family history of (a genetic predisposition for) such disorders or (ii) one or more risk factors for developing such disorders.

After stratifying or selecting a subject based on whether the subject will be more likely or less likely to respond to a SMA therapy (e.g., SPINRAZA®), a medical practitioner (e.g., a doctor) can administer the appropriate therapeutic modality to the subject. Methods of administering SMA therapies are known in the art.

It is understood that any therapy described herein (e.g., a therapy comprising SPINRAZA® or a therapy that does not comprise SPINRAZA®) can include one or more additional therapeutic agents. That is, any therapy described herein can be co-administered (administered in combination) with one or more additional therapeutic agents such as, but not limited to, other SMA therapies described herein. Furthermore, any therapy described herein can include one or more agents for treating, or more side-effects of a therapy comprising the SMA therapy (e.g., SPINRAZA®).

Combination therapies (e.g., co-administration of a SMA therapy comprising (e.g., SPINRAZA®) and one or more additional SMA therapies or additional therapeutic agents) can be, e.g., simultaneous or successive. For example, a SMA therapy and the additional therapeutic agent(s) can be administered at the same time or at different times. In some embodiments, the one or more additional therapeutic agents can be administered first in time and the SMA therapy (e.g., SPINRAZA®) administered second in time.

In cases where the subject having SMA and predicted to respond to a SMA therapy (e.g., SPINRAZA®) has been previously administered the SMA therapy, the therapy can replace or augment a previously or currently administered therapy. For example, upon treating with SPINRAZA®, administration of a non-SPINRAZA® therapy can cease or diminish, e.g., be administered at lower levels. Administration of the previous therapy can be maintained while the therapy comprising SPINRAZA® is administered. In some embodiments, a previous therapy can be maintained until the level of SPINRAZA® reaches a level sufficient to provide a therapeutic effect.

In some cases, the method of treatment involves treating a fetus in utero. The fetus to be treated is determined to be in need of treatment with a SMA therapy based on high NF levels (e.g., pNF-H or NF-L) relative to a control. If, for example, the fetus has been identified as having SMA based on genetic testing and has been identified as having elevated NF levels, the fetus can be treated with a SMA therapy (e.g., SPINRAZA®). In some instances, the method of treatment relates to Type 0 patients. If a fetus is identified with very high NF levels and one SMN2 copy, the chances are high that the fetus has Type 0 SMA. Treating such a fetus prenatally with an SMA therapy (e.g., SPINRAZA®) can effectively treat that fetus.

11. Kits

This disclosure also provides kits. In certain embodiments, the kit can include an antibody or antibodies that can be used to detect one or more of the biomarkers disclosed herein or their concentration or expression levels. For example, the kit can include an antibody that specifically binds NF-H (e.g., pNF-H). The antibodies in the kit may be monoclonal or polyclonal and can be further conjugated with a detectable label. In some embodiments, the kit includes probes that can be used to identify or detect any of the biomarkers disclosed herein. In some embodiments, the kit includes any of the nucleic acid arrays. In some embodiments, the kit includes probes and antibodies that can be used to identify or detect any of the biomarkers disclosed herein or their expression or expression levels. The kits can, optionally, contain instructions for detecting and/or measuring the concentration of one or more proteins or the levels of mRNA in a biological sample.

The kits can optionally include, e.g., a control (e.g., a concentration standard for the protein being assessed) or control labeled-amplicon set containing known amounts of one or more amplicons recognized by nucleic acid probes of the array. In some instances, the control can be an insert (e.g., a paper insert or electronic medium such as a CD, DVD, or floppy disk) containing an expression level or expression level ranges of one or more proteins (e.g., pNF-H) or RNAs predictive of SMA, or of responsiveness to a SMA therapy (e.g., SPINRAZA®).

In some embodiments, the kits can include one or more reagents for processing a biological sample (e.g., calibration reagents, buffers, diluents, color reagents, reagents to stop a reaction). For example, a kit can include reagents for isolating a protein from a biological sample and/or reagents for detecting the presence and/or amount of a protein in a biological sample (e.g., an antibody that binds to the protein that is the subject of the detection assay and/or an antibody that binds the antibody that binds to the protein).

In certain embodiments, the kit includes at least one microplate (e.g., a 96 well plate; i.e., 12 strips of 8 wells). The microplate can be provided with its corresponding plate cover. The microplate can be polystyrene or of any other suitable material. The microplate can have the antibody that is used to identify the presence of a particular biomarker coated inside each well. The antibody may be conjugated to a detectable label. The kit may also include at least one adhesive strip.

In some embodiments, the kits can include a software package for analyzing the results of, e.g., expression profile or a microarray analysis.

The kits can also include one or more antibodies for detecting the protein expression of any of the genes described herein (e.g., NF-H). For example, a kit can include (or in some cases consist of) one or a plurality of antibodies capable of specifically binding to one or more proteins encoded by any of the genes described herein and optionally, instructions for detecting and/or measuring the concentration of one or more proteins and/or a detection antibody comprising a detectably-labeled antibody that is capable of binding to at least one antibody of the plurality. In some embodiments, the kits can include antibodies that recognize NF-H, NF-L, and/or NF-M. In some embodiments, the kits can include antibodies that recognize pNF-H.

In certain embodiments, the kit can also optionally include one or more unit doses of a SMA therapy (e.g., SPINRAZA®).

The kits described herein can also, optionally, include instructions for administering a SMA therapy, where the concentration of one or more proteins or expression level of one or more RNAs predicts that a subject having or suspected of having SMA will respond to a SMA therapy (e.g., SPINRAZA®).

In a specific embodiment, the kit comprises one or more of the following:

(i) a microplate (e.g., a 96 well plate). The microplate can be coated with an anti-NF-H antibody that is conjugated with a detectable label. The anti-NF-H antibody may monoclonal or polyclonal. The antibody can be e.g., from mouse, rabbit, rat, or guinea pig. The detectable label can be e.g., horse radish peroxidase, biotin, a fluorescent moiety, a radioactive moiety, a histidine tag, or a peptide tag. The microplate can be provided with a cover and optionally, one or more adhesive strips.

(ii) a vial containing anti-NF-H conjugated with a detectable label. The detectable label can be e.g., horse radish peroxidase, biotin, a fluorescent moiety, a histidine tag, a peptide tag. The vial can also include a preservative.

(iii) a vial containing an NF-H standard of known concentration. The NF-H can be a recombinant human NF-H.

(iv) a vial containing an assay diluent.

(v) a vial containing a calibrator diluent.

(vi) a vial containing wash buffer. The buffer may be provided as a concentrate.

(vii) one or more vials containing color reagents.

(viii) a vial containing a stop solution to stop the colorimetric reaction.

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

EXAMPLES

The Examples below refer to several clinical studies designated: NURTURE, ENDEAR, EMBRACE, and CHERISH.

ENDEAR, was a Phase 3, multicenter, randomized, double-blind, sham-procedure-controlled study of ISIS 396443 in subjects with symptomatic infantile-onset SMA. Results of the final analysis for this study provide clear evidence that subjects treated with intrathecal (IT) ISIS 396443 achieved statistically significant and clinically meaningful improvement in the acquisition of motor milestones as well as sustained and clinically meaningful improvements in event-free survival, overall survival, motor function, and motor neuron health in comparison with a control group of subjects who received a sham procedure. Improvement relative to control was seen as early as 2 months after the initiation of treatment (end of the loading dose period), with clear separation from control at 6 months after the initiation of treatment.

At the time of the final analysis, 121 subjects had received at least 1 dose of ISIS 396443 administered as IT injection by lumbar puncture (LP) [n=80] or sham procedure (n=41). Among these subjects, 89 subjects (65 in the ISIS 396443 arm and 24 in the control arm) had completed the study. A total of 42 subjects (32 subjects in the ISIS 396443 arm and 10 subjects in the control arm) remained in the study at the time the study was closed and were recorded as having discontinued treatment due to early study closure. Two subjects in the ISIS 396443 group and 1 subject in the control group voluntarily withdrew from the study prior to the transition to open label treatment, and 29 subjects (13 in the ISIS 396443 group and 16 in the control group) died.

The demographics and SMA history of the 121 subjects in this Study were consistent with a Type I SMA population.

There were 45% males and 55% females; 86% of subjects were white.

Most subjects (86%) had symptom onset at less than 12 weeks of age. Median age was 8.0 weeks (range: 1 to 20 weeks) at SMA symptom onset, 12.0 weeks (range: 0 to 30 weeks) at SMA diagnosis, and 166 days (range: 20 to 211 days) at screening. Median disease duration at the time of enrollment was 13.1 weeks (range: 0.0 to 25.86 weeks).

Most subjects (99%) had 2 SMN2 gene copies by local laboratory testing at study entry.

Among the 80 subjects in the ISIS 396443 group, 73 (91%) had received at least 4 doses of ISIS 396443 (i.e., completed the loading dose phase); 32 subjects (40%) received all 6 planned doses. Of the 41 subjects in the control group, 34 subjects (83%) had at least 4 sham procedures, with 14 subjects (34%) undergoing all 6 procedures.

CHERISH, was a Phase 3, double-blind, randomized, sham-procedure controlled study of ISIS 396443 in subjects with later-onset SMA. Approximately 117 subjects were enrolled into the study and allocated to treatment with ISIS 396443 or sham control in a 2:1 ratio. ISIS 396443 was administered IT using a loading regimen (dosing on Days 1, 29, and 85), followed by a maintenance dose 6 months thereafter (dosing on Day 274).

Results of the interim analysis provide clear evidence that subjects treated with IT ISIS 396443 achieved statistically significant gains in motor function as well as sustained and clinically meaningful improvements in motor milestones in comparison with a control group of subjects who received a sham procedure. Although improvement in motor function was seen at all timepoints, separation from the control group clearly occurred at 6 months after the initiation of treatment. Based on an assessment of risk-benefit of ISIS 396443, the Sponsor decided to terminate the study early, and subjects were given the opportunity to enroll into an open-label extension study.

As of the interim analysis, 126 subjects had received at least 1 dose of ISIS 396443 (n=84) or sham procedure (n=42). No subjects discontinued treatment or withdrew from the study. As of the data cutoff date, 49 of 84 subjects (58%) in the ISIS 396443 group and 23 of 42 subjects (55%) in the control group were continuing in the study. The primary analysis of change from baseline in HFMSE score at 15 months was based on the ITT Set composed of 126 subjects, 84 treated with ISIS 396443 and 42 who underwent the sham procedure. The main analysis of WHO motor milestones was performed using the Interim Efficacy Set, which was composed of 54 subjects (35 subjects treated with ISIS 396443 and 19 subjects who underwent the sham procedure) who had the opportunity to be assessed at the Day 456 Visit (i.e., Month 15). All other secondary and tertiary endpoint analyses were performed on the ITT Set.

The demographics and baseline disease characteristics, including SMA and medical history, of the 126 subjects in this Study were consistent with a population highly likely to develop Type II or III SMA.

- There were 47% males and 53% females; 75% were white.
- The median age was 11 months (range: 6 to 20) at SMA symptom onset, 18 months (range: 0 to 48 months) at SMA diagnosis, and 3.0 years (range: 2 to 9 years) at screening. The median disease duration at the time of enrollment was 35.7 months (range: 8 to 94 months).
- Most subjects (88%) had 3 SMN2 gene copies by laboratory testing at study entry and 8% of subjects had 2 copies.
- Among the 84 subjects in the ISIS 396443 group, all had received at least 3 doses of ISIS 396443 (i.e., completed the loading doses), 76 subjects (90%) received all 4 doses. Of the 42 subjects in the control group, all subjects had received at least 3 sham procedures, with 40 subjects (95%) undergoing all 4 procedures.
- Median time on study was similar between the 2 treatment groups (i.e., 412.5 and 419.5 days for the ISIS 396443 and control groups, respectively). The total number of subject-years on study was 134.06 (88.84 subject-years in the ISIS 396443 group and 45.22 subject-years in the control group).

Subjects treated with ISIS 396443 realized clinically meaningful benefits as compared to subjects who received a sham procedure. These benefits included statistically significantly greater gains in motor function as measured by HFMSE, as well as an improvement in upper limb functional ability.

NURTURE, is an ongoing Phase 2, open-label, multicenter, single-arm study to assess the efficacy, safety, tolerability, and PK of ISIS 396443 in presymptomatic SMA. The study is being conducted in subjects who were ≤6 weeks of age at the time of enrollment with genetic documentation of 5q SMA, 2 or 3 copies of the SMN2 gene, CMAP≥1 mV, and the absence of signs or symptoms of SMA. Up to 25 subjects are planned. Efficacy data available to date indicate that the development and achievement of motor milestones for most subjects has been more consistent with normal development than with the natural history of Type I SMA.

At the time of the data cutoff for NURTURE, 20 subjects had been enrolled and received at least 1 dose of ISIS 396443. All subjects are continuing in the study. Eighteen subjects who have received all 4 loading doses or have had the opportunity to complete the Day 64 visit comprise the efficacy set.

- Most subjects are male (55%) and white (50%).
- Age at the first dose ranged from 3 to 42 days, with a median of 19 days.
- Of the 18 subjects, 13 subjects (72%) have 2 copies of the SMN2 gene and 5 subjects (28%) have 3 copies.

Efficacy data were available for 18 subjects at Day 64, 16 subjects at Day 183, 11 subjects at Day 302, 9 subjects at Day 365, and 5 subjects at Day 421. Results at the later of these visits demonstrate development that is inconsistent with Type I SMA and the experience of subjects' affected siblings and consistent with age-matched expectations for healthy infants.

EMBRACE, is a Phase 2, randomized, sham-procedure controlled, multicenter study of ISIS 396443 in subjects with SMA who are not eligible to participate in ENDEAR or CHERISH. This study evaluated a unique set of subjects who exhibited symptoms of infantile-onset SMA, at an age too young to be eligible for CHERISH, or subjects who exhibited later-onset symptoms of SMA, at an age too old to be eligible for ENDEAR, and were screened at an age too old or had too many copies of SMN2 to be eligible for ENDEAR. Thus, the population in this study provided the opportunity to explore the safety, tolerability, and efficacy of ISIS 396443 in the context of both infantile-onset and later-onset SMA in subjects with up to 3 copies of SMN2.

This study was initially designed as a double-blind study but evolved into a 2-part study, including a double blind phase (Part 1) and an open-label extension phase (Part 2), after the positive and robust efficacy results from a pivotal study in the ISIS 396443 clinical development program were observed. Part 1 was a randomized, double blind, sham-procedure controlled study. Twenty-one subjects were enrolled into the study from 7 sites in the United States and Germany. Randomization of subjects was stratified based on age of SMA (infantile onset [≤6 months] vs. later onset [>6 months]). Subjects were scheduled to receive a total of 6 intrathecal (IT) injections or 6 sham procedures over the dosing period of approximately 10 months. However, Part 1 of the study was terminated early because of the positive and robust efficacy results observed in an interim analysis of one of the pivotal studies for the ISIS 396443 clinical development program. As a result of the decision by the study Sponsor to terminate Part 1 of the study early based on the assessment of the risk-benefit of ISIS 396443, all subjects were invited to complete the End of Part 1 Evaluation assessments early and participate in Part 2 of the study. The total duration of subject participation in Part 1 was planned to be approximately 15 months, but because Part 1 of the study was terminated early, eligible subjects were given the opportunity to enroll into Part 2 of the study immediately following their End of Part 1 Evaluation assessments.

A total of 21 subjects were enrolled in this study. Subjects were randomized to ISIS 396443 or control (sham procedure) in a 2:1 ratio. Randomization was stratified based on age at onset of clinical signs and symptoms consistent with SMA (≤6 months [infantile onset] vs. >6 months [later onset]). Fourteen subjects received ISIS 396443 in Part 1 of the study and 7 subjects received the sham procedure.

A total of 21 subjects were screened and enrolled in Part 1 of this study. All subjects were randomized in a 2:1 ratio: 14 subjects received ISIS 396443, and 7 subjects received control treatment (sham procedure). In addition, randomization was stratified based on age at onset of clinical signs and symptoms consistent with infantile onset (≤6 months) and later onset (>6 months) SMA. The first subject was treated on 19 Aug. 2015, and the end of study (Part 1) was on 20 Dec. 2016. All subjects received study treatment according to their randomization assignment.

The 21 subjects randomized and dosed who comprised the ITT set were enrolled at 7 study sites in 2 countries. Sixteen subjects (76%) were enrolled at 6 sites in the United States, and 5 subjects (24%) were enrolled at 1 site in Germany. Subjects were randomized across sites. Of the 21 randomized subjects, 13 had SMA onset at ≤6 months and the remaining 8 subjects had SMA onset at >6 months.

Twenty-one subjects received treatment, and of these, 14 subjects completed due to early termination of the study (6 subjects [86%] in the control group and 8 subjects [57%] in the ISIS 396443 group). Nine subjects (43%) completed treatment up to Day 302 (2 subjects [29%] in the control group and 7 subjects [50%] in the ISIS 396443 group). Six subjects (29%), all in the ISIS 396443 group, completed the Part 1 Final Follow-up Evaluation (Day 422). One subject (5%) assigned to the control group died due to brain death on Study Day 289.

Demographics and Baseline Disease Characteristics:

Of the 21 subjects in the study, 11 (52%) were male and 10 (48%) were female. Age at first dose ranged from 7 to 53 months (median: 17 months). Eleven subjects (52%) were between 7 and 18 months of age, and 10 subjects (48%) were greater than 18 months of age. Nine subjects (43%) were White, 5 subjects (24%) were Asian, and 2 subjects (10%) were Other.

Efficacy and Pharmacokinetics

Subjects in the ISIS 396443 group required less ventilator use than did subjects in the control group.

The proportion of HINE motor milestone responders was greater in the ISIS 396443 group than in the control group, and there was at least 1 responder in each HINE motor milestone category from the ISIS 396443 group, with the greatest number of subjects showing improvement in the categories of head control, rolling, and sitting.

Safety

In this study, ISIS 396443 was well tolerated when administered as multiple IT injections (4 loading doses followed by maintenance doses every 4 months). No new safety concerns were identified in the overall safety profile of ISIS 396443.

Results from Part 1 of this Phase 2, randomized, sham-procedure controlled study of ISIS 396443 have shown clear evidence that intrathecal administration of ISIS 396443 is effective in a population of subjects with either infantile onset or later-onset SMA. When compared with a control group of study subjects who received only sham administration, subjects treated with ISIS 396443 achieved and sustained gains in motor milestones and, based on Investigator and caregiver assessments, generally appeared to grow and thrive. A positive correlation was observed between CSF ISIS 396443 concentration and HINE motor milestone total score, which increased over time. The dosing regimen if ISIS 396443 was safe and well tolerated in this study, as no new safety concerns were identified, and the safety results were consistent with results from other studies in the ISIS 396443 clinical development program. Based on the results observed across all primary safety and exploratory efficacy parameters, and in contrast with the results observed in the untreated control group, ISIS 396443 improves motor function in subjects with infantile-onset and later-onset SMA.

Methods

The plasma at selected time points was assayed to detect the pNF-H concentration. All plasma samples were frozen at −70° C. until ready for use. Plasma samples at selected schedule time were diluted at the minimum required dilution (MRD) using assay dilution buffer.

NF-H was assayed using polyclonal anti-NF-H antibodies from Encor Biotechnology (Cat #RPCA-NF-H; and/or Cat #CPCA-NF-H). These antibodies specifically detect the hyper-phosphorylated form of NF-H.

A qualification experiment was conducted before any patient samples were assayed. Such experiment aimed to evaluate the reproducibility and variability of the pNF-H concentration generated by Ella technology platform developed by ProteinSimple®. Ella technology utilizes microfluidic cartridges that include pre-loaded reagents so only the samples and wash buffer are loaded onto the cartridge. Once the cartridge is loaded, the platform will automatically calculate the pNF-H concentration by using its build-in factory-calibrated standard curve.

To evaluate the quality of each cartridge as well as any unforeseen potential confound effects in real-time, 4 quality control (QC) samples are included in each cartridge: three buffer spiked QC, high, middle and low, and an endogenous quality control (EQC) sample from a commercially available Multiple Sclerosis (MS) patient (Bioreclamation) is run. These four QCs are used to monitor the performance of the bioanalytical method and to assess the integrity and validity of the results of the unknown samples analyzed in an individual batch.

Samples from same subjects were analyzed on the same cartridge. Two aliquots for each sample were placed on the same cartridge in a randomized order to ensure that the samples analysis take into account possible placement effect.

Example 1: Correlation of CSF Vs. Plasma pNF-H Levels

Plasma and CSF samples from the clinical studies NURTURE and EMBRACE were analyzed at the same timepoint and in the same subject to determine the correlation in pNF-H levels. A high correlation (R=0.88) between CSF and plasma levels of pNF-H were identified (FIG. 1). This result suggests that plasma levels of pNF-H and other subunits of neurofilament are highly predictive of CSF levels of these same proteins.

Example 2: Plasma Levels of pNF-H as Predictor of Disease and Severity

Plasma samples from clinical studies NURTURE, ENDEAR, EMBRACE, and CHERISH were analyzed for levels of pNF-H at baseline (prior to treatment with ISIS 396443 (NURTURE, ENDEAR, EMBRACE, and CHERISH) or SHAM procedure (ENDEAR, EMBRACE, and CHERISH)). Plasma samples from healthy volunteers (age 4-18 years) were also analyzed for levels of pNF-H.

Figure 2:
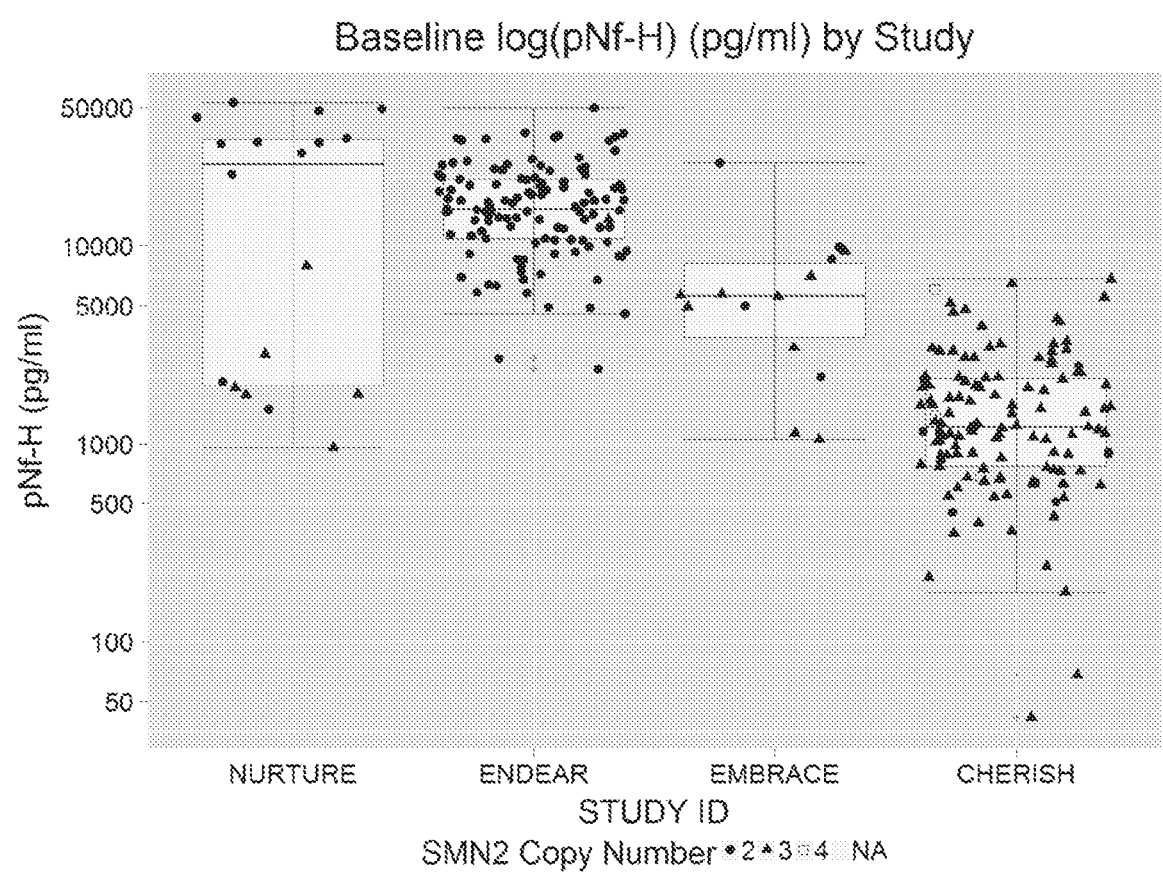
FIG. 2 shows the levels of pNF-H levels in plasma samples in subjects from NURTURE, ENDEAR, EMBRACE and CHERISH clinical studies who have two, three, or four copies of SMN2.

Results from health volunteers demonstrated pNF-H<300 pg/mL for all ages. Results from NURTURE, ENDEAR, EMBRACE, CHERISH demonstrate that plasma levels of pNF-H in clinical trial subjects with SMA are almost all >300 pg/mL. Some subjects have levels up to approximately 50,000 pg/mL. In general, subjects with two SMN2 copies have higher levels than subjects with three SMN2 copies. Furthermore, subjects with symptom onset ≤6 months of age (ENDEAR) have higher levels than subjects with symptom onset >6 months of age (CHERISH). See FIG. 2.

However, important exceptions are observed. Within NURTURE, one subject has two SMN2 copies and a pNF-H level more consistent with subjects with 3 SMN2 copies. This subject has a sibling also with two SMN2 copies who developed Type II SMA. So, although this subject has an SMN2 copy number that suggests the subject should develop Type I SMA, the subject has a family history that suggests the subject will develop Type II SMA. The pNF-H level may provide additional diagnostic acumen beyond SMN1 deletion and SMN2 copy number. Within ENDEAR, one subject has three SMN2 copies and a pNF-H levels more consistent with subjects with 2 SMN2 copies. This subject had symptom onset ≤6 months of age and therefore was more consistent with Type I SMA (most often 2 SMN2 copies) than Type II SMA (most often 3 SMN2 copies).

Overall, the results demonstrate that among subjects with SMA, plasma levels of pNF-H are markedly elevated compared to healthy volunteers. And, among subjects with SMA, subjects with a more severe phenotype have higher plasma pNF-H levels than subjects with a less severe phenotype.

Example 3: Correlation of pNF-H Versus Age
(SMN2 Copy Number=2)

Figure 3:
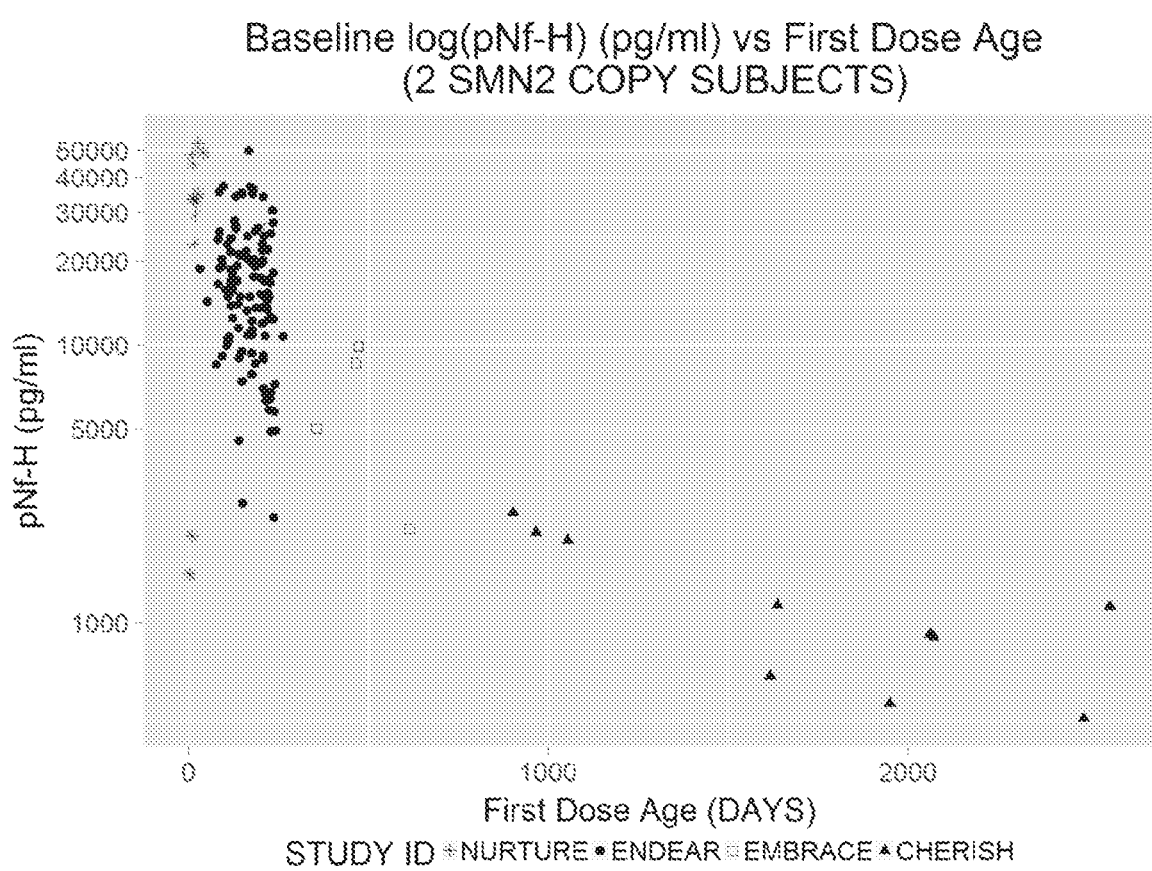
FIG. 3 is a depiction of the levels of pNF-H in subjects who have two SMN2 copies with increasing age.

Plasma samples from clinical studies NURTURE, ENDEAR, EMBRACE, and CHERISH were analyzed for levels of pNF-H at baseline (prior to treatment with ISIS 396443 (NURTURE, ENDEAR, EMBRACE, and CHERISH) or SHAM procedure (ENDEAR, EMBRACE, and CHERISH)). For this analysis, subjects were limited to those with two SMN2 copies. Baseline log transformed pNF-H levels were plotted versus age at first dose (or SHAM procedure). In general, younger subjects had higher pNF-H levels than older subjects. See FIG. 3.

This result suggests that pNF-H levels decline with increasing age among subjects with 2 SMN2 copies.

Example 4: Correlation of pNF-H Versus Age
(SMN2 Copy Number=3)

Figure 4:
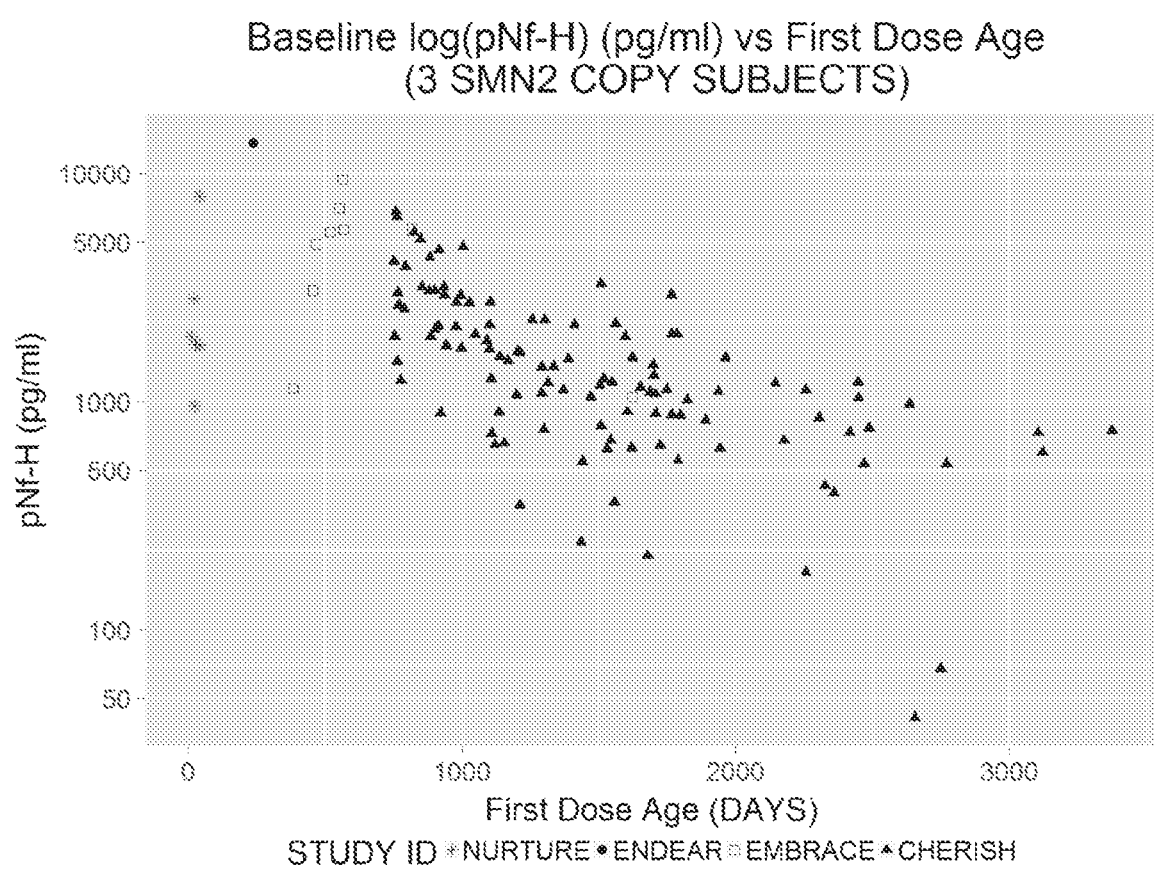
FIG. 4 is a depiction of the levels of pNF-H in subjects who have three SMN2 copies with increasing age.

Plasma samples from clinical studies NURTURE, ENDEAR, EMBRACE, and CHERISH were analyzed for levels of pNF-H at baseline (prior to treatment with ISIS 396443 (NURTURE, ENDEAR, EMBRACE, and CHERISH) or SHAM procedure (ENDEAR, EMBRACE, and CHERISH)). For this analysis, subjects were limited to those with three SMN2 copies. Baseline log transformed pNF-H levels were plotted versus age at first dose (or SHAM procedure). In general, younger subjects had higher pNF-H levels than older subjects. See FIG. 4.

This result suggests that pNF-H levels decline with increasing age among subjects with three SMN2 copies.

Example 5: Correlation of pNF-H Versus Age

Figure 5:
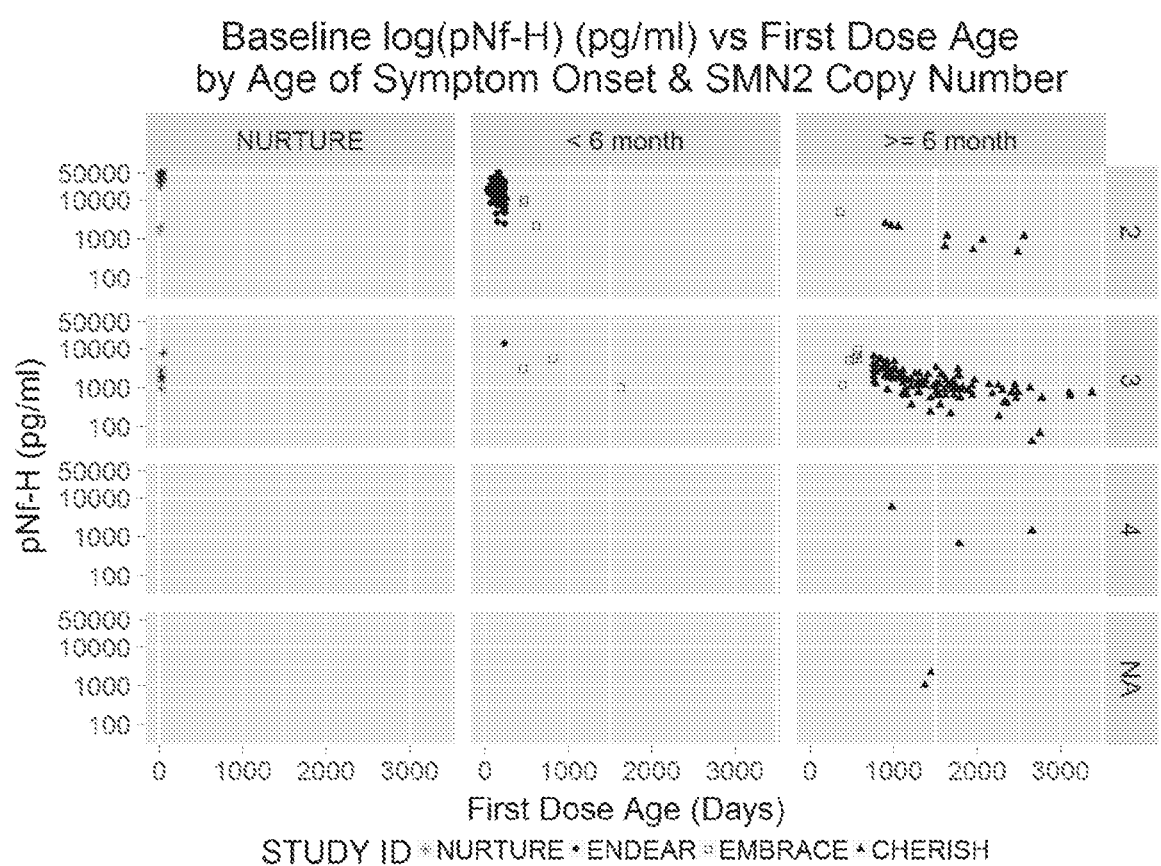
FIG. 5 is a depiction of the levels of pNF-H in subjects who have two, three, or four SMN2 copies and age of symptom onset.

Plasma samples from clinical studies NURTURE, ENDEAR, EMBRACE, and CHERISH were analyzed for levels of pNF-H at baseline (prior to treatment with ISIS 396443 (NURTURE, ENDEAR, EMBRACE, and CHERISH) or SHAM procedure (ENDEAR, EMBRACE, and CHERISH)). For this analysis, subjects were stratified by age of symptom onset (presymptomatic (NURTURE), <6 months, ≥6 months) and by SMN2 copy number (2, 3, 4 or NA). In general, younger subjects had higher pNF-H levels than older subjects within each strata of age of symptom onset and SMN2 copy number. See FIG. 5.

This result suggests that pNF-H levels decline with increasing age among subjects independent of age of symptom onset or SMN2 copy number.

Example 6: Correlation of pNF-H Versus Age

Plasma samples from clinical study ENDEAR were analyzed for levels of pNF-H at baseline (prior to treatment with ISIS 396443 or SHAM procedure). For this analysis, quartiles of pNF-H were identified within the entire study population. The quartiles were defined as 2390 to 10,900 pg/mL; 10,900 to 15,400 pg/mL; 15,400 to 21,600 pg/mL; and 21,600 to 50,100 pg/mL. In general, subjects with higher pNF-H levels at baseline appeared to be younger at first dose, younger at symptom onset, and younger at SMA diagnosis. Furthermore, subjects with higher pNF-H levels at baseline appeared to have lower mean CHOP INTEND (Children's Hospital of Philadelphia Infant Test of Neuromuscular Disorders) scores and peroneal CMAP amplitudes at baseline. See FIGS. 6-8.

These results suggest that higher pNF-H levels at first dose are associated with a more severe phenotype as demonstrated as a younger age at symptom onset; lower motor function (CHOP INTEND); and worse motor neuron health (CMAP amplitude).

Example 7: pNF-H Levels and Motor Function

Figure 9:
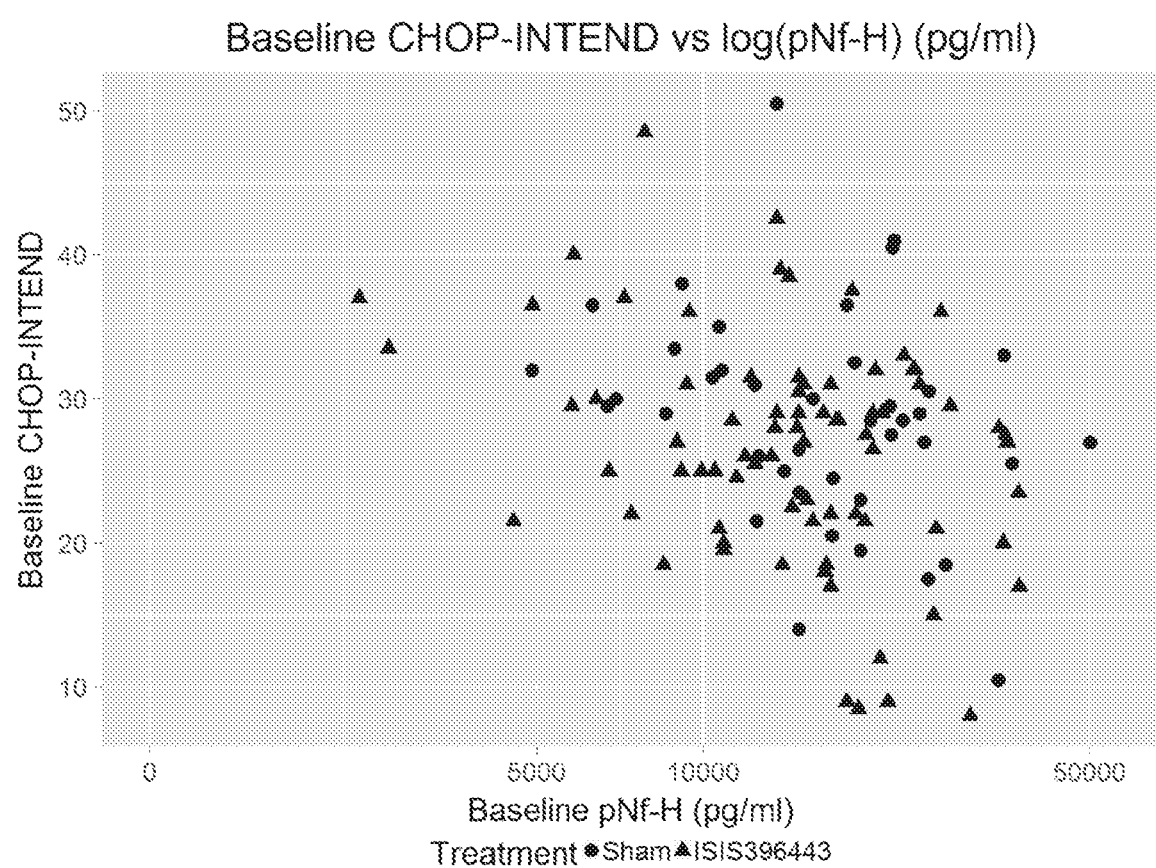
FIG. 9 shows the correlation of baseline log(pNF-H) levels and baseline CHOP INTEND scores.

Plasma samples from clinical study ENDEAR were analyzed for levels of pNF-H at baseline (prior to treatment with ISIS 396443 or SHAM procedure). For this analysis, levels of log transformed pNF-H were plotted versus baseline CHOP INTEND. In general, subjects with higher pNF-H levels had lower CHOP INTEND and subjects with lower pNF-H levels had higher CHOP INTEND with a correlation of −0.3. See FIG. 9.

This result suggests that pNF-H levels are inversely associated with motor function. This relationship appears to be linear.

Example 8: Prediction of Motor Function Based on pNF-H Levels

Plasma samples from clinical study ENDEAR were analyzed for levels of pNF-H at baseline (prior to treatment with ISIS 396443 or SHAM procedure). For this analysis, a linear regression model was built to examine the relationship between various potential predictors of baseline CHOP INTEND. A final model was identified that only included those variables that remained statistically significant (Baseline NF-H; treatment group, disease duration (weeks); sex; age of first dose (days); age of SMA symptom onset (weeks); age of SMA diagnosis (weeks); gestational age (weeks); baseline weight (kg); (gestational age+age of first dose)×(gestational age+age of SMA symptom onset); (gestational age+age of SMA diagnosis). In this final model, baseline log transformed pNF-H levels were statistically significant. See FIG. 10.

This result suggests that pNF-H levels are a significant predictor of baseline motor function.

Example 9: pNF-H (p2/mL) Levels in ENDEAR

Figure 11:
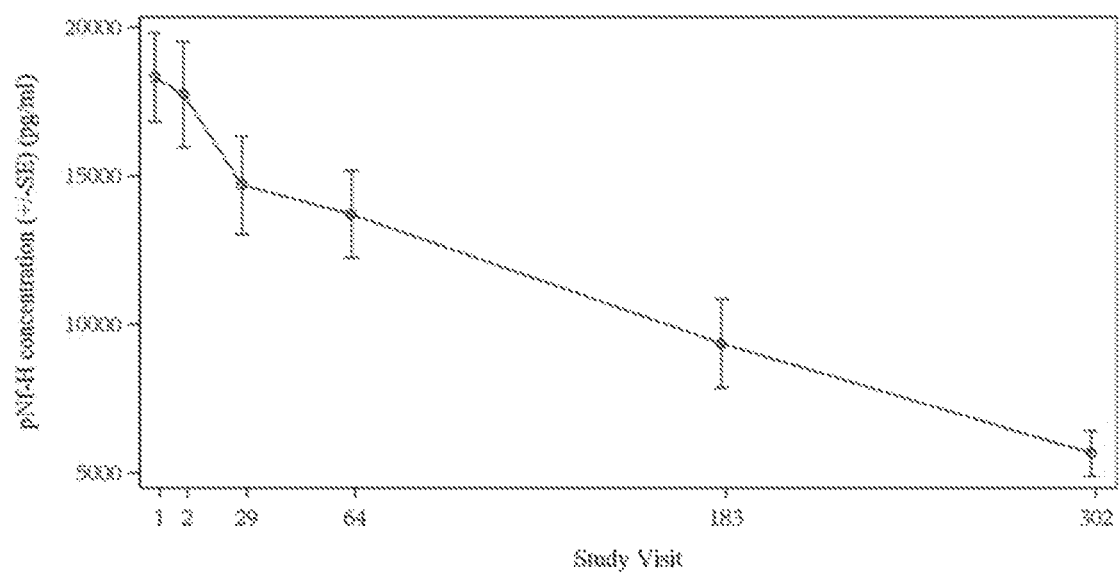
FIG. 11 is a graphical depiction of pNF-H levels in ENDEAR.

Plasma samples from clinical study ENDEAR were analyzed for levels of pNF-H at Study Days 1, 2, 29, 64, 183, and 302 (SHAM procedure). For this analysis, absolute values of pNF-H were log transformed and plotted by study day. Over time, mean pNF-H levels decline nearly linearly from approximately 18,000 pg/mL at Study Day 1 to approximately 5,000 pg/mL at Study Day 302. See FIG. 11.

Example 10: Percent Change in pNF-H (pg/mL) Levels in ENDEAR

Figure 12:
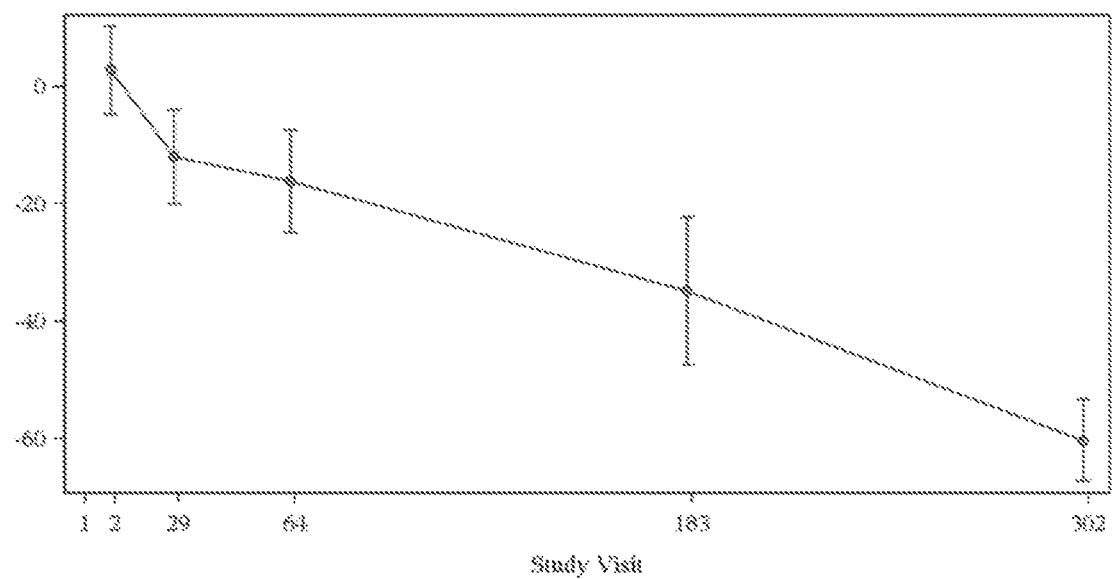
FIG. 12 is a graphical depiction of the percentage change in NF-H levels in ENDEAR.

Plasma samples from clinical study ENDEAR were analyzed for levels of pNF-H at Study Days 1, 2, 29, 64, 183, and 302 (SHAM procedure). For this analysis, percent change from baseline for absolute values of pNF-H were plotted by study day. Over time, mean percent change in pNF-H levels decline nearly linearly from approximately 0% at Study Day 1 to approximately −60% at Study Day 302. See FIG. 12.

Example 11: Drug Effect on pNF-H (pg/mL) Levels in ENDEAR

Figure 13:
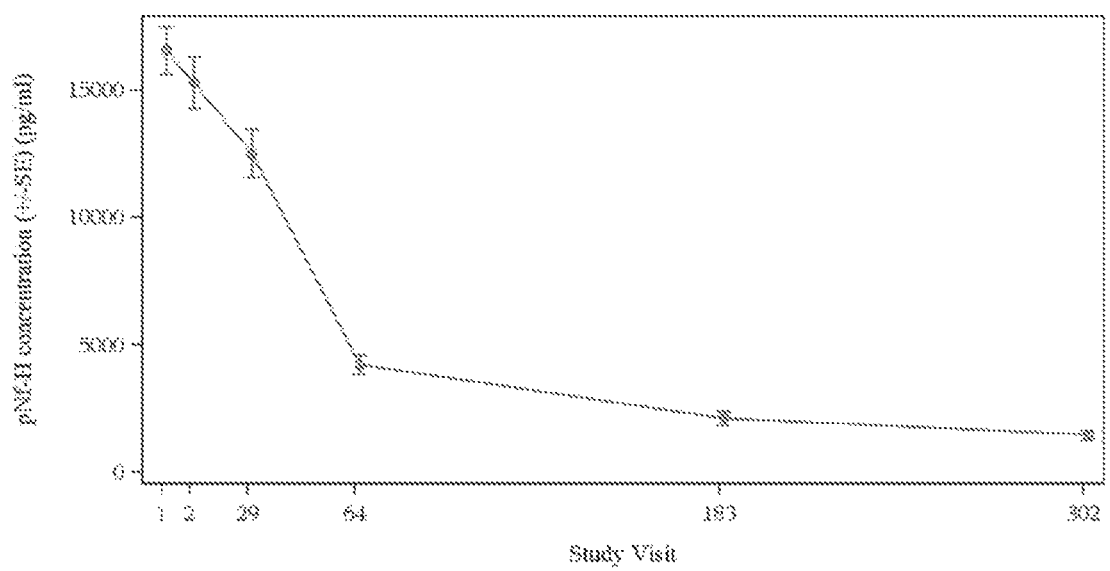
FIG. 13 is a graphical depiction of SMA drug therapy on pNF-H levels in ENDEAR.

Plasma samples from clinical study ENDEAR were analyzed for levels of pNF-H at Study Days 1, 2, 29, 64, 183, and 302 (ISIS 396443). For this analysis, absolute values of pNF-H were log transformed and plotted by study day. Over time, mean pNF-H levels decline from approximately 18,000 pg/mL at Study Day 1 to approximately 5,000 pg/mL at Study Day 64 and then to approximately 1,000 pg/mL at Study Day 302. See FIG. 13.

This result suggests subjects treated with ISIS 396443 have a different pattern in the decline of pNF-H levels compared to subjects who received SHAM control.

Example 12: Drug Effect on Percent Change in pNF-H (pg/mL) Levels in ENDEAR

Figure 14:
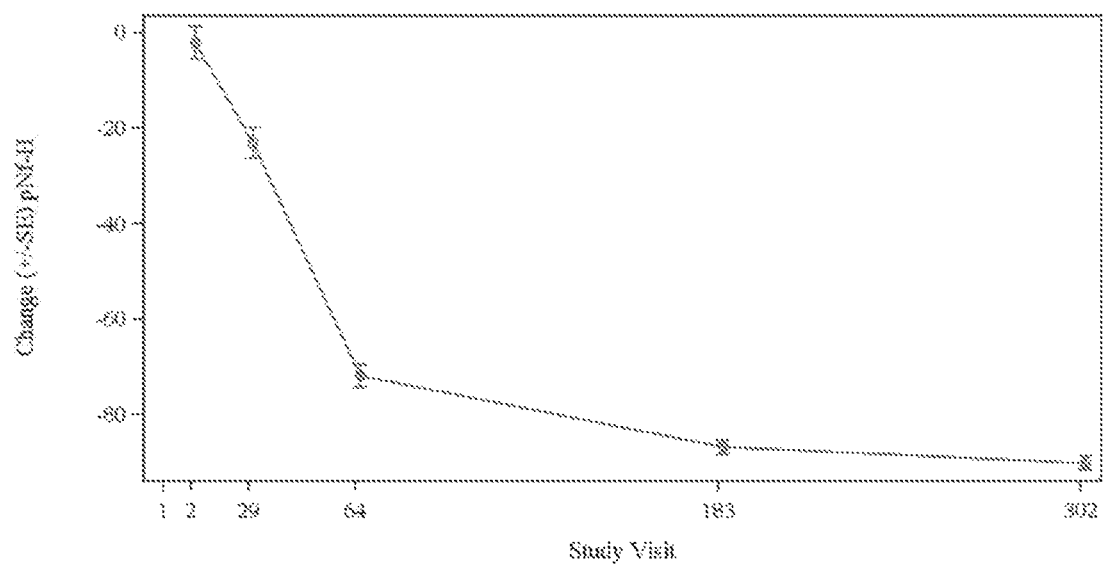
FIG. 14 is a graphical depiction of SMA drug therapy on the percentage change in NF-H levels in ENDEAR.

Plasma samples from clinical study ENDEAR were analyzed for levels of pNF-H at Study Days 1, 2, 29, 64, 183, and 302 (ISIS 396443). For this analysis, percent change from baseline for absolute values of pNF-H were plotted by study day. Over time, mean percent change in pNF-H levels decline nearly linearly from approximately 0% at Study Day 1 to approximately −70% at Study Day 64 and −90% at Study Day 302. See FIG. 14.

This result suggests subjects treated with ISIS 396443 have a different pattern in the decline of pNF-H levels compared to subjects who received SHAM control.

Example 13: Change in pNF-H Levels at Various Time Points

Figure 15:
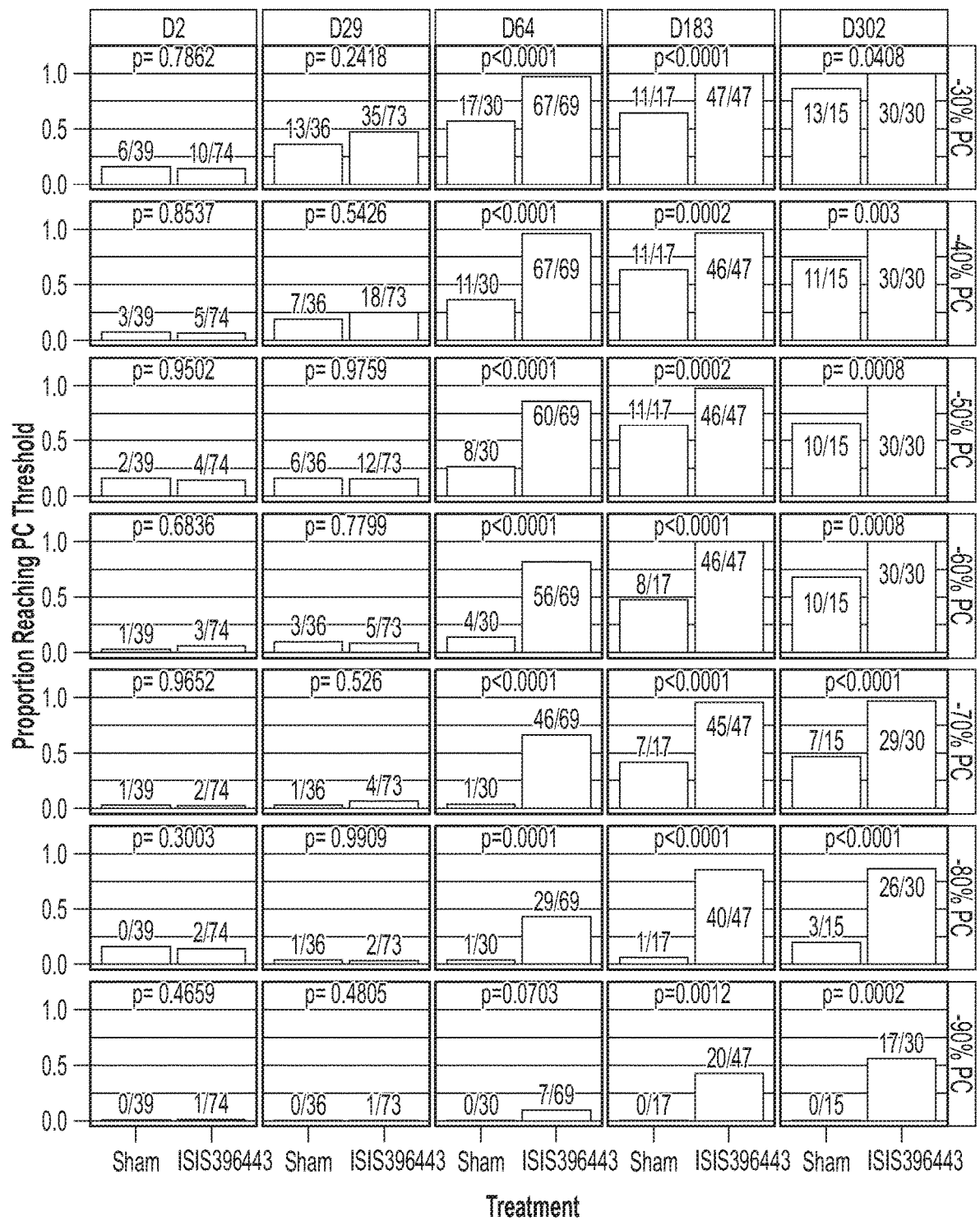
FIG. 15 is a depiction of the change in pNF-H levels at various time points.

Plasma samples from clinical study ENDEAR were analyzed for levels of pNF-H at Study Days 1, 2, 29, 64, 183, and 302 (ISIS 396443 and SHAM control). For this analysis, the percent of subjects at each study day who achieved specific levels of percent change from baseline for absolute values of pNF-H among subjects who received ISIS 396443 was compared to subjects who received SHAM control. Statistical significance (p<0.05) was first identified between the two study groups at study day 64. The greatest difference between percentages of each arm achieving a specific change in pNF-H occurred at study day 183 for −80% change. See FIG. 15.

This result suggests that a difference in the groups can be identified as early as study day 64 and the best separation between groups occurs using −80% as the threshold of change.

Example 14: Association of HINE-2 Score on Day 183 with pNF-H Levels of Day 64

Figure 16:
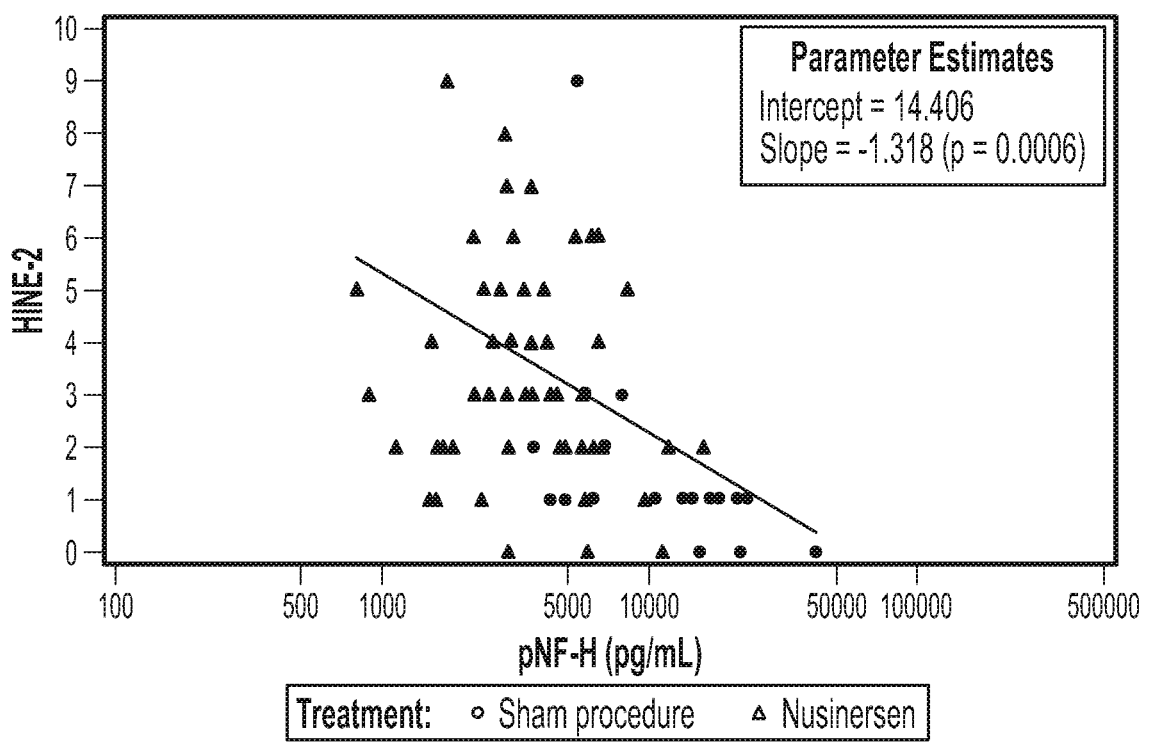
FIG. 16 is a graph depicting the association of HINE-2 Score on Day 183 with pNF-H levels on Day 64.

Plasma samples from clinical study ENDEAR were analyzed for levels of pNF-H at Study Day 64 and the total motor milestone score (HINE-2 (Hammersmith Infant Neurological Examination Section 2)) was assessed at Study Day 183 (ISIS 396443 and SHAM control). For this analysis, a linear regression model was constructed to determine whether pNF-H levels on Study Day 64 were associated with the total HINE-2 score on Study Day 183. pNF-H levels on Study Day 64 were significantly associated with total HINE-2 scores on Study Day 183, p=0.0006. See FIG. 16.

This result suggests that present pNF-H levels can predict future levels of motor milestones among infants with infantile-onset SMA.

Example 15: Association of HINE-2 Score on Day 183 with pNF-H Levels on Day 64 (with Covariates)

Plasma samples from Study CS3B (ENDEAR) were analyzed for levels of pNF-H at Study Day 64 and the total motor milestone score (HINE-2 (Hammersmith Infant Neurological Examination Section 2)) was assessed at Study Day 183 (ISIS 396443 and SHAM control). For this analysis, a linear regression model was constructed to determine whether pNF-H levels on Study Day 64 were associated with total HINE-2 score on Study Day 183 after accounting for multiple potential confounders. After controlling for multiple potential confounders, the final model included Day 64 log transformed pNF-H (p<0.0001) and disease duration (p=0.0029). See FIG. 17.

This result suggests that present pNF-H levels can predict future levels of motor milestones after controlling for treatment and other potential confounders among infants with infantile-onset SMA.

Example 16: Association of CHOP INTEND of Day 183 with pNF-H Levels on Day 64

Figure 18:
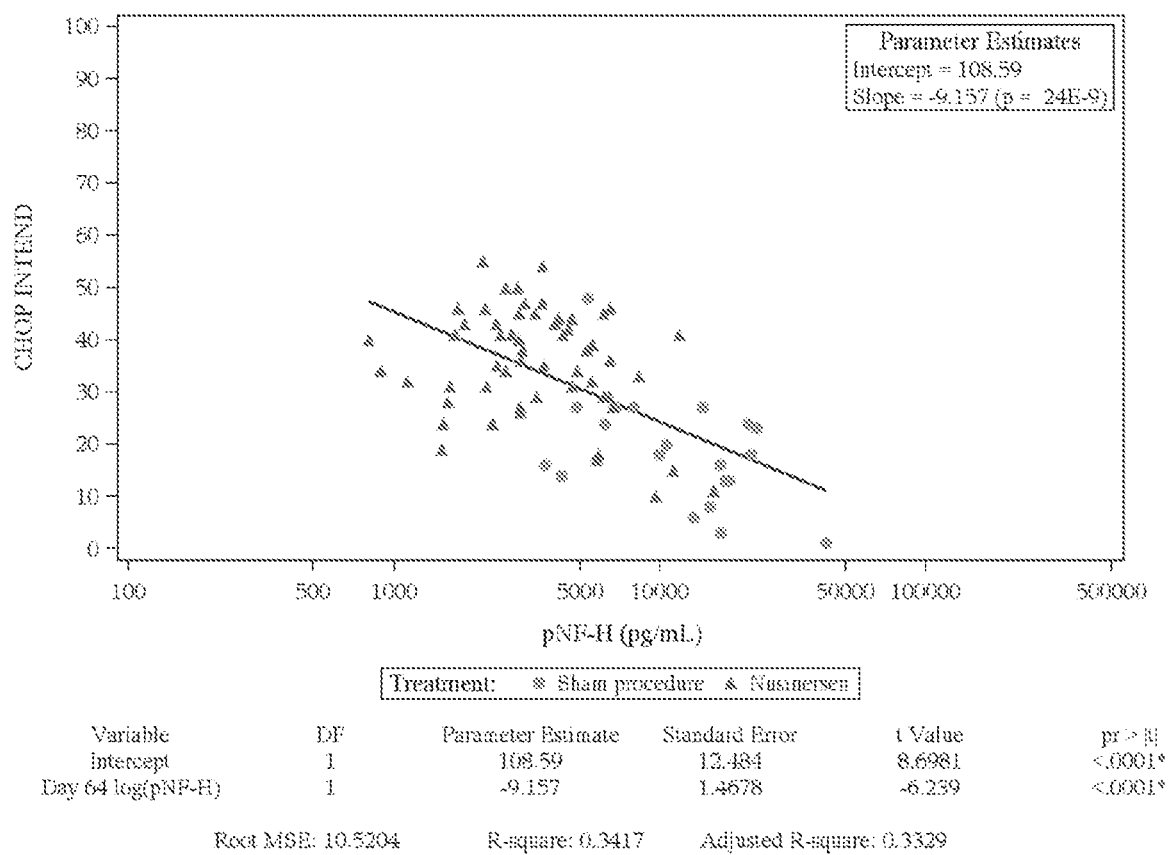
FIG. 18 is a graph depicting the association of CHOP INTEND Score on Day 183 with pNF-H levels on Day 64.

Plasma samples from clinical study ENDEAR were analyzed for levels of pNF-H at Study Day 64 and the CHOP INTEND was assessed at Study Day 183 (ISIS 396443 and SHAM control). For this analysis, a linear regression model was constructed to determine whether pNF-H levels on Study Day 64 were associated with the CHOP INTEND score on Study Day 183. pNF-H levels on Study Day 64 were significantly associated with the CHOP INTEND scores on Study Day 183, p<0.0001. See FIG. 18.

This result suggests that present pNF-H levels can predict future levels of general motor function among infants with infantile-onset SMA.

Example 17: Association of CHOP INTEND Score on Day 183 with pNF-H Levels on Day 64 (with Covariates)

Plasma samples from clinical study ENDEAR were analyzed for levels of pNF-H at Study Day 64 and the CHOP INTEND score was assessed at Study Day 183 (ISIS 396443 and SHAM control). For this analysis, a linear regression model was constructed to determine whether pNF-H levels on Study Day 64 were associated with CHOP INTEND score on Study Day 183 after accounting for multiple potential confounders. After controlling for multiple potential confounders, the final model included Day 64 log transformed pNF-H (p=0.0001), treatment group (p=0.005), and disease duration (p=0.0003). See FIG. 19.

This result suggests that present pNF-H levels can predict future levels of general motor function after controlling for treatment and other potential confounders among infants with infantile-onset SMA.

Example 18: HINE-2 (Responder/Non-Responder) Category Versus pNF-H Levels on Day 183

Figure 20:
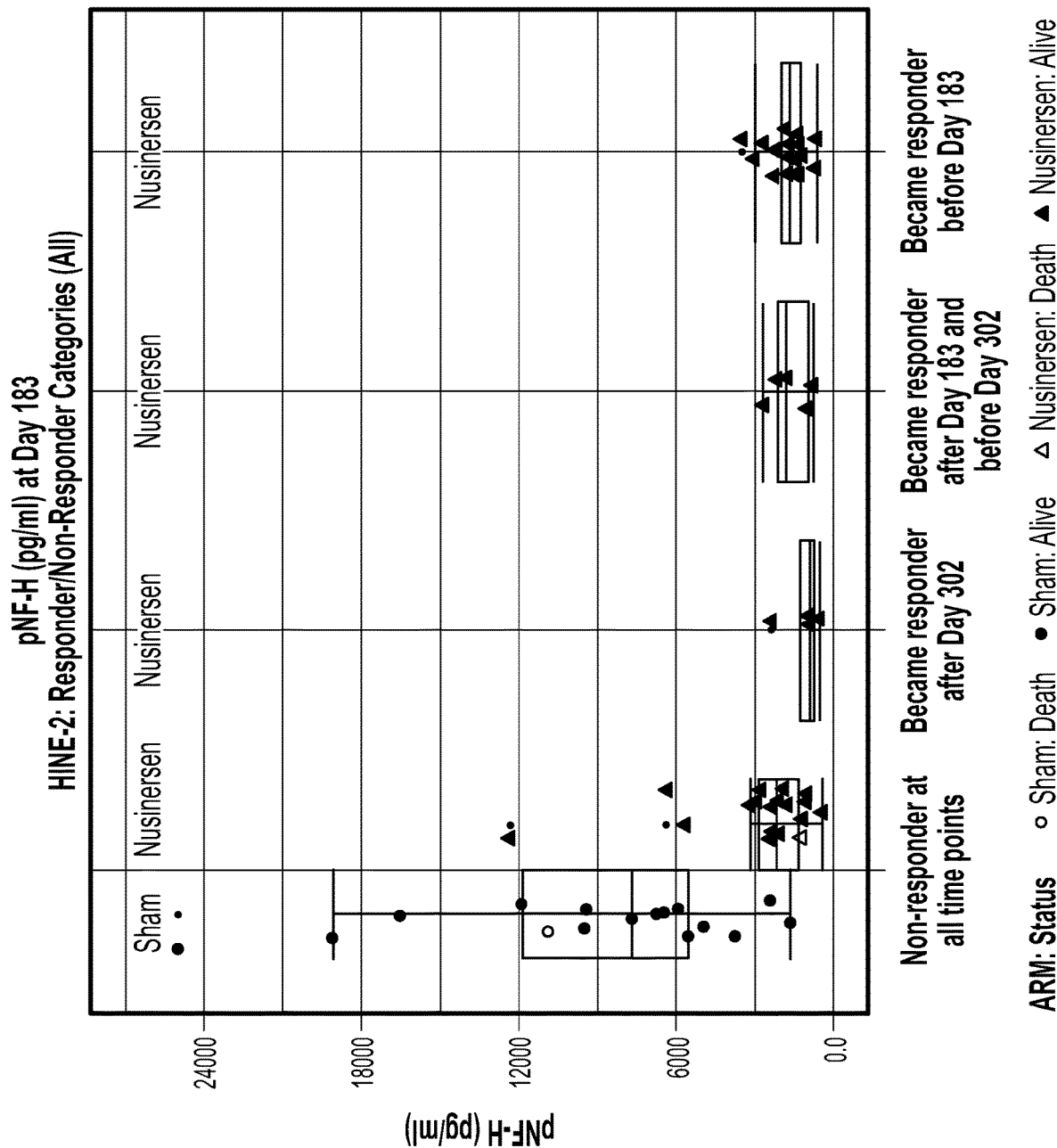
FIG. 20 is a depiction of HINE-2 (Responder/Non-responder) category versus pNF-H levels on Day 183.

Plasma samples from clinical study ENDEAR were analyzed for levels of pNF-H at Study Day 183 and the HINE-2 (Hammersmith Infant Neurological Examination Section 2) responder status was assessed at Study Day 183; between Study Day 183 and Study Day 302; after Study Day 302 (ISIS 396443 and SHAM control). If a subject became a responder based upon the protocol definition of a HINE-2 responder, the time of this achievement was noted. If a subject did not become a responder within Study CS3B, that was noted. No subjects in the SHAM control group became a HINE-2 responder during Study CS3B. Most subjects who received ISIS 396443 who became a responder did so by Study Day 183. Among SHAM control subjects, almost all subjects had pNF-H levels above the overall median (2130 pg/mL). Among subjects who received ISIS 396443 and became responders by Study Day 183, most had pNF-H levels below the study median at Study Day 183. Among subjects who received ISIS 396443 and became responders between Study Days 183 and 302, most had pNF-H levels below the study median at Study Day 183. Among subjects who received ISIS 396443 and became responders between Study Days 302 and end of study, most had pNF-H levels below the study median at Study Day 183. Among subjects who received ISIS 396443 and did not become responders within ENDEAR, approximately half had pNF-H levels below the study median (2130 pg/mL) at Study Day 183. See FIG. 20.

These results suggest that achieving a certain threshold of pNF-H by 183 days after treatment initiation is able to differentiate treatment from SHAM control and predict eventual responders on treatment.

Figure 21:
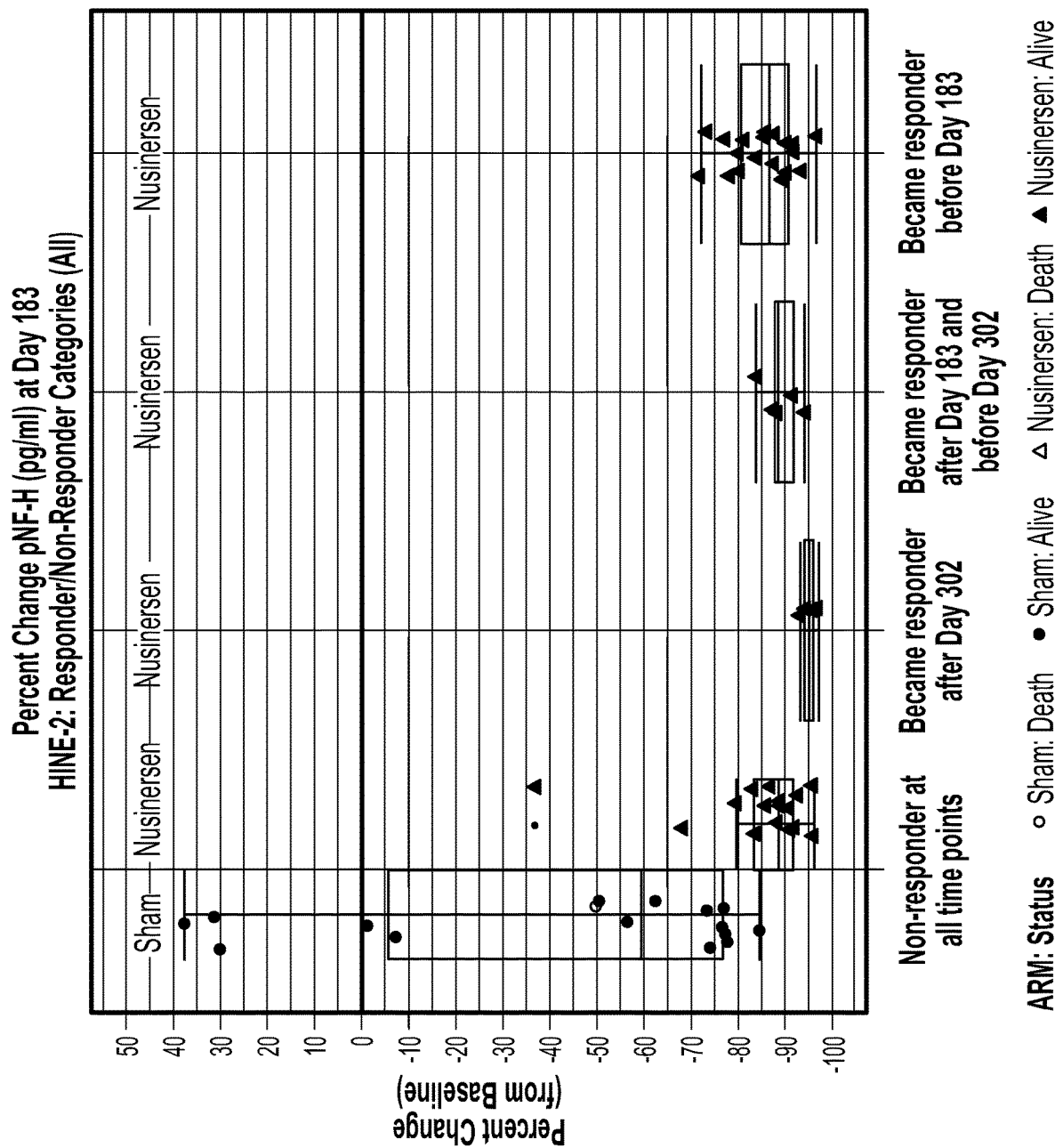
FIG. 21 is a graphical depiction of HINE-2 (Responder/Non-responder) category versus Day 183 percentage change in pNF-H levels.

Example 19: HINE-2 (Responder/Non-Responder) Category Versus pNF-H Levels on Day 183 Percent Change in pNF-H Levels Plasma samples from clinical study ENDEAR were analyzed for levels of pNF-H at Study Day 183 and the HINE-2 responder status was assessed at Study Day 183; between Study Day 183 and Study Day 302; after Study Day 302 (ISIS 396443 and SHAM control). The percent change in pNF-H was calculated between baseline and Study Day 183. If a subject became a responder based upon the protocol definition of a HINE-2 responder, the time of this achievement was noted. If a subject did not become a responder within Study CS3B, that was noted. No subjects in the SHAM control group became a HINE-2 responder during Study CS3B. Most subjects who received ISIS 396443 who became a responder did so by Study Day 183. Among SHAM control subjects, all subjects had a decline in pNF-H levels <80%. Among subjects who received ISIS 396443 and became responders by Study Day 183, almost half had a decline in pNF-H levels >80% at Study Day 183. Among subjects who received ISIS 396443 and became responders between Study Days 183 and 302, most had a change in pNF-H levels >80% at Study Day 183. Among subjects who received ISIS 396443 and became responders between Study Days 302 and end of study, most had a change in pNF-H levels >80% at Study Day 183. Among subjects who received ISIS 396443 and did not become responders within ENDEAR, approximately half had a change in pNF-H levels >80% at Study Day 183. See FIG. 21.

These results suggest that achieving a certain threshold of decline in pNF-H by 183 days after treatment initiation can differentiate treatment from SHAM control and predict eventual responders on treatment.

Example 20: CHOP INTEND (Responder/Non-Responder) Category Versus pNF-H Levels on Day 183

Figure 22:
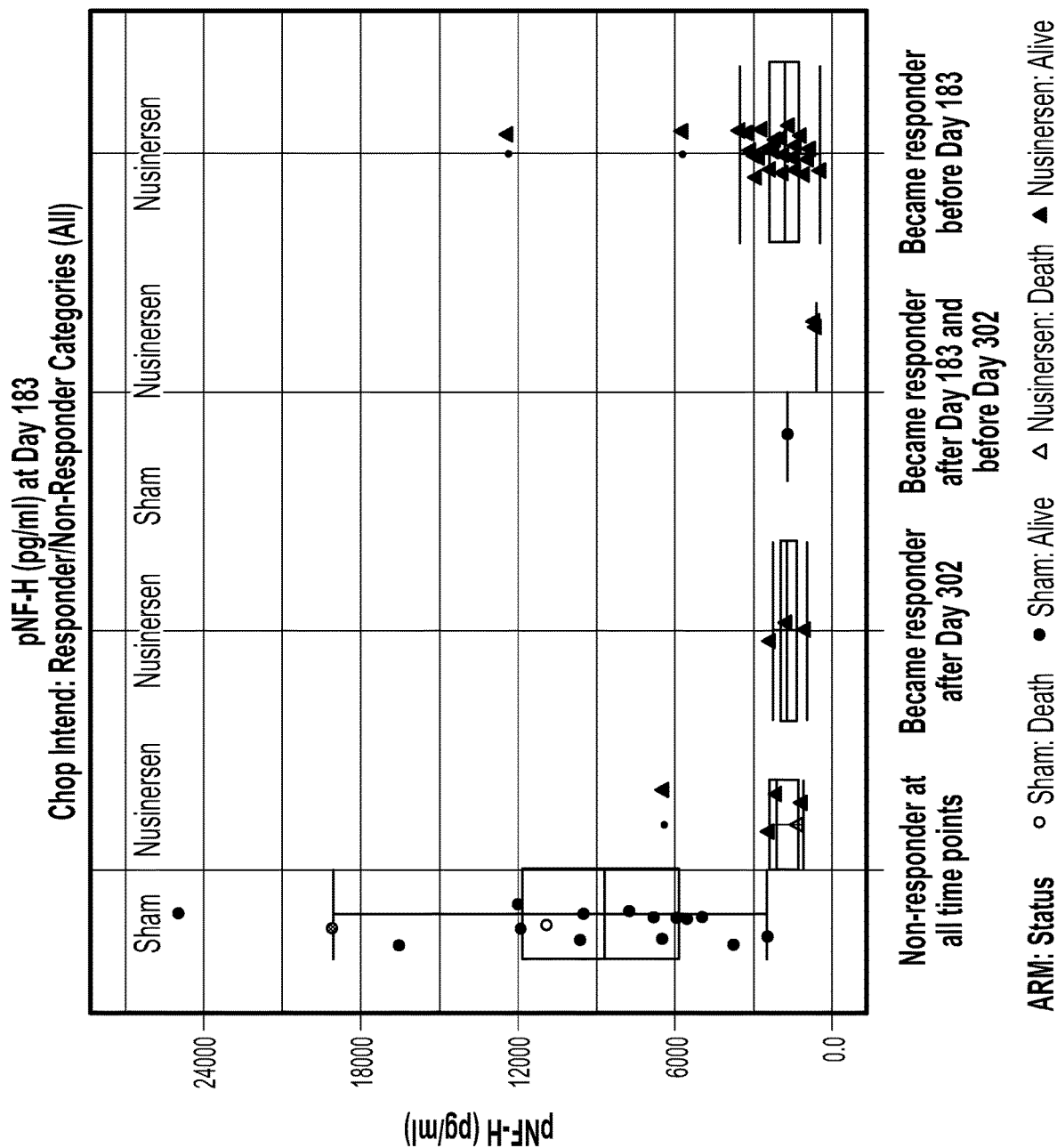
FIG. 22 is a graphical depiction of CHOP INTEND (Responder/Non-responder) category versus pNF-H levels on Day 183.

Plasma samples from clinical study ENDEAR were analyzed for levels of pNF-H at Study Day 183 and the CHOP INTEND responder status was assessed at Study Day 183; between Study Day 183 and Study Day 302; after Study Day 302 (ISIS 396443 and SHAM control). If a subject became a responder based upon the protocol definition of a CHOP INTEND responder, the time of this achievement was noted. If a subject did not become a responder within Study CS3B, that was noted. One subject in the SHAM control group became a CHOP INTEND responder during Study CS3B. Most subjects who received ISIS 396443 who became a responder did so by Study Day 183. Among SHAM control subjects, almost all subjects had pNF-H levels above the overall median. Among subjects who received ISIS 396443 and became responders by Study Day 183, most had pNF-H levels below the study median at Study Day 183. Among subjects who received ISIS 396443 and became responders between Study Days 183 and 302, most had pNF-H levels below the study median at Study Day 183. Among subjects who received ISIS 396443 and became responders between Study Days 302 and end of study, most had pNF-H levels below the study median at Study Day 183. Among subjects who received ISIS 396443 and did not become responders within ENDEAR, approximately half had pNF-H levels below the study median at Study Day 183. See FIG. 22.

These results suggest that achieving a certain threshold of pNF-H by 183 days after treatment initiation can differentiate treatment from SHAM control and predict eventual responders on treatment.

Figure 23:
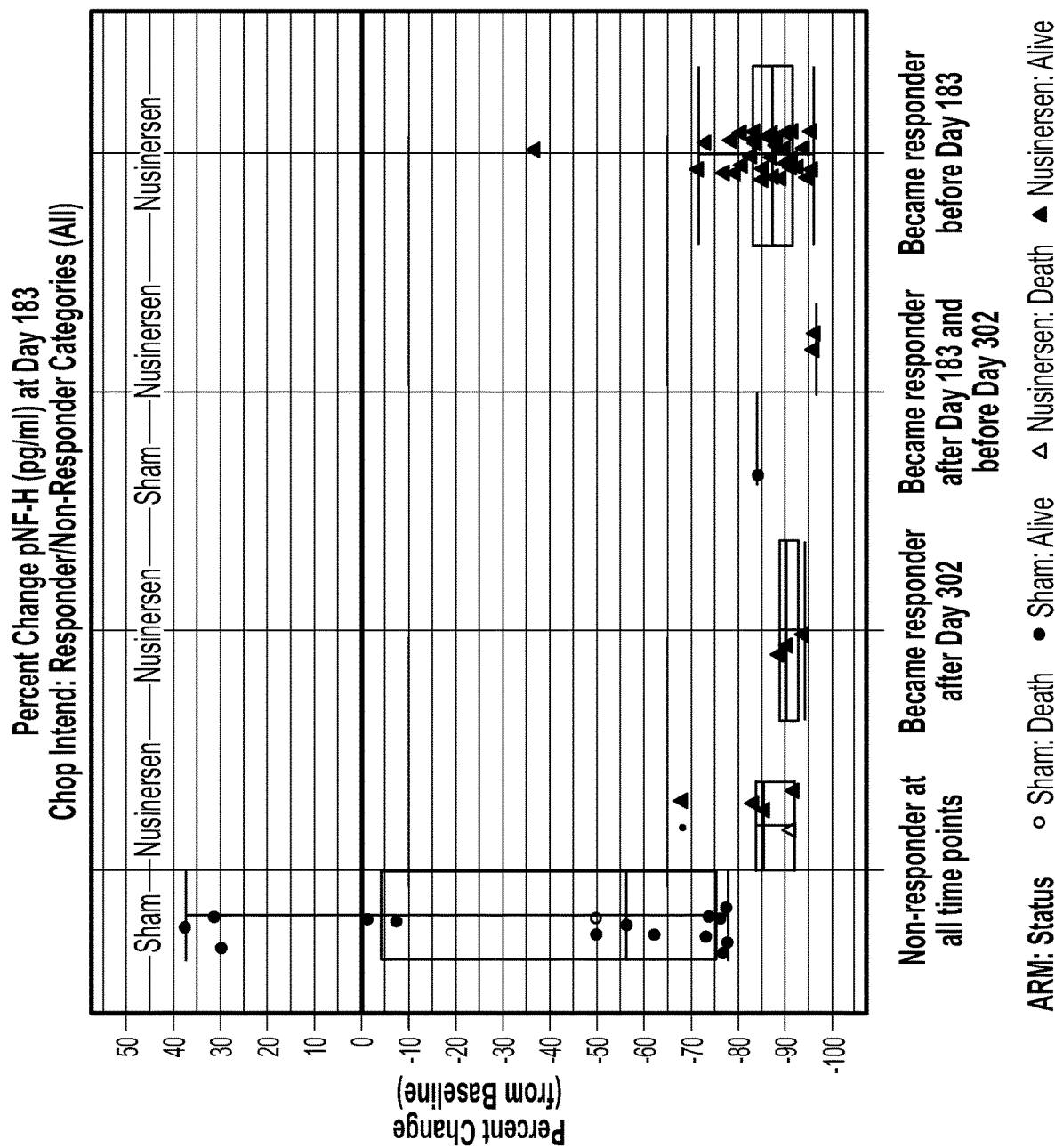
FIG. 23 is a graphical depiction of CHOP INTEND (Responder/Non-responder) category versus Day 183 percentage change in pNF-H levels.

Example 21: CHOP INTEND (Responder/Non-Responder) Category Versus pNF-H Levels on Day 183 Percent Change in pNF-H Levels Plasma samples from clinical study ENDEAR were analyzed for levels of pNF-H at Study Day 183 and the CHOP INTEND responder status was assessed at Study Day 183; between Study Day 183 and Study Day 302; after Study Day 302 (ISIS 396443 and SHAM control). The percent change in pNF-H was calculated between baseline and Study Day 183. If a subject became a responder based upon the protocol definition of a HINE-2 responder, the time of this achievement was noted. If a subject did not become a responder within Study CS3B, that was noted. One subject in the SHAM control group became a CHOP INTEND responder during Study CS3B. Most subjects who received ISIS 396443 who became a responder did so by Study Day 183. Among SHAM control subjects, all but one subject had a decline in pNF-H levels <80%. Among subjects who received ISIS 396443 and became responders by Study Day 183, almost half had a decline in pNF-H levels >80% at Study Day 183. Among subjects who received ISIS 396443 and became responders between Study Days 183 and 302, most had a change in pNF-H levels >80% at Study Day 183. Among subjects who received ISIS 396443 and became responders between Study Days 302 and end of study, most had a change in pNF-H levels >80% at Study Day 183. Among subjects who received ISIS 396443 and did not become responders within ENDEAR, approximately half had a change in pNF-H levels >80% at Study Day 183. See FIG. 23.

These results suggest that achieving a certain threshold of decline in pNF-H by 183 days after treatment initiation can differentiate treatment from SHAM control and predict eventual responders on treatment.

Example 22: Maintenance of Drug Effect: pNF-H (pg/mL) Levels in NURTURE

Figure 24:
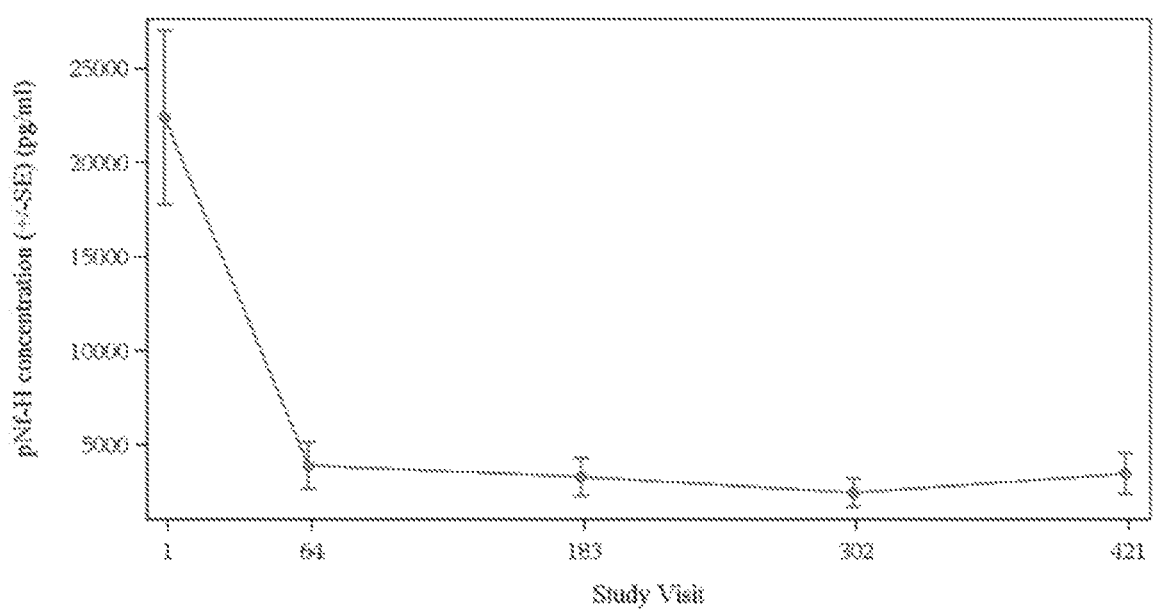
FIG. 24 is a graphical depiction of the maintenance of drug effect based on pNF-H (pg/mL) levels in NURTURE.

Plasma samples from clinical study NURTURE were analyzed for levels of pNF-H at Study Days 1, 64, 183, 302, and 421 (ISIS 396443). In this analysis, absolute levels of pNF-H were plotted by Study Day. See FIG. 24.

Example 23: Maintenance of Drug Effect: pNF-H (pg/mL) Levels in EMBRACE

Figure 25:
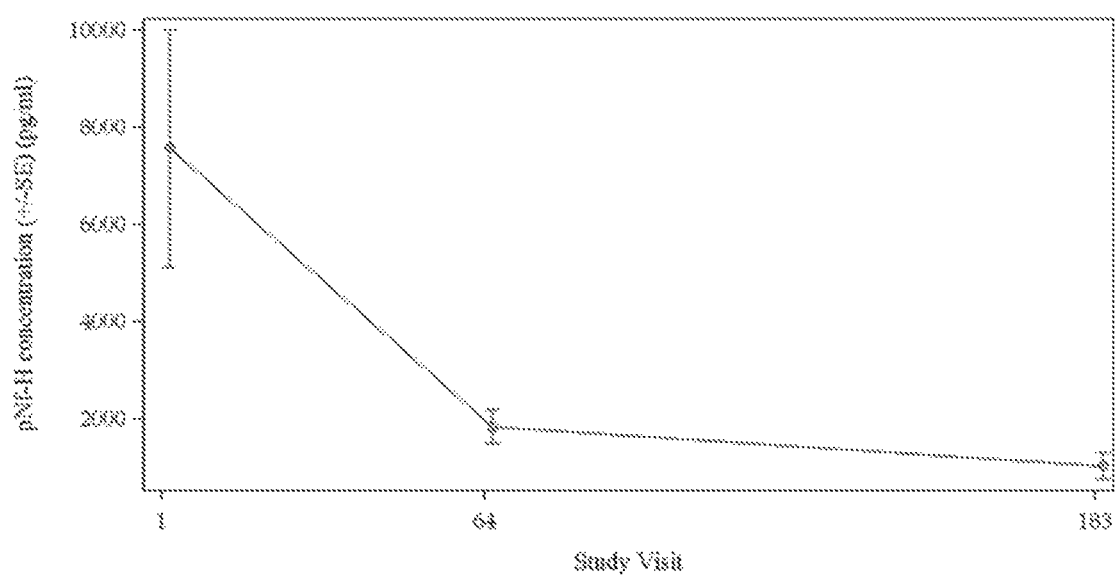
FIG. 25 is a graphical depiction of the maintenance of drug effect based on pNF-H (pg/mL) levels in EMBRACE.

Plasma samples from clinical study EMBRACE were analyzed for levels of pNF-H at Study Days 1, 64, and 183 (ISIS 396443). In this analysis, absolute levels of pNF-H were plotted by Study Day. See FIG. 25.

The results of this analysis suggest that significant decline occurs by Study Day 64 and this new level appears stable to Study Day 183.

Figure 26:
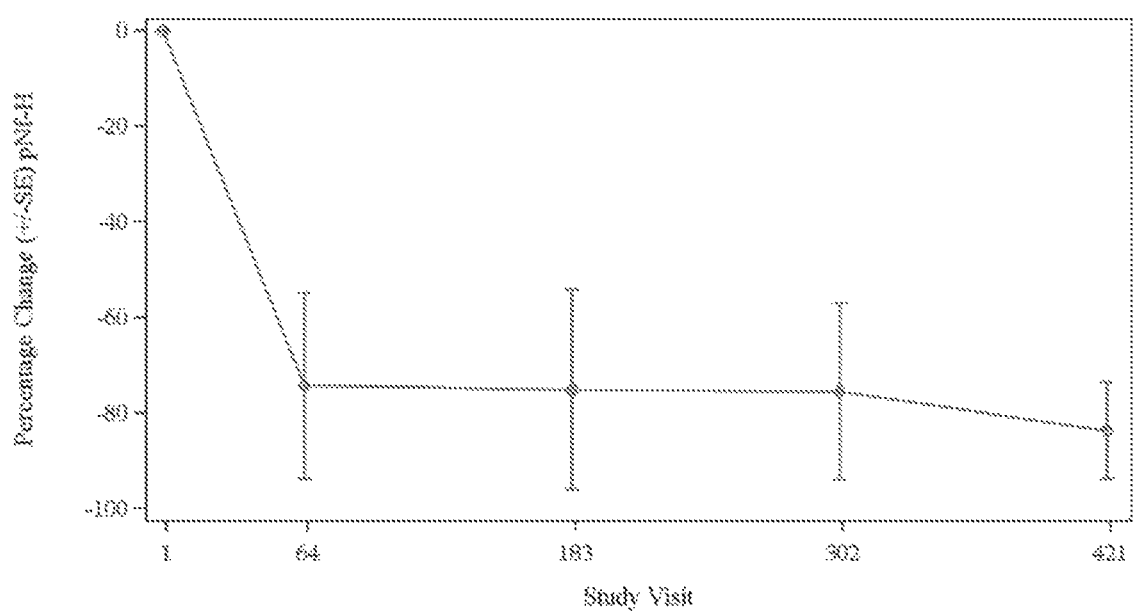
FIG. 26 is a graphical depiction of the drug effect on percentage change in pNF-H (pg/mL) levels in NURTURE.

Example 24: Maintenance of Drug Effect: Percentage Change in pNF-H (pg/mL) Levels in NURTURE Plasma samples from Study 232SM201 (NURTURE) were analyzed for levels of pNF-H at Study Days 1, 64, 183, 302, and 421 (ISIS 396443). In this analysis, levels of percent change in pNF-H from baseline were plotted by Study Day. See FIG. 26.

The results of this analysis suggest that significant decline (−80%) occurs by Study Day 64 and this new level appears stable to Study Day 421.

Example 25: Maintenance of Drug Effect: pNF-H (pg/mL) Levels in EMBRACE

Figure 27:
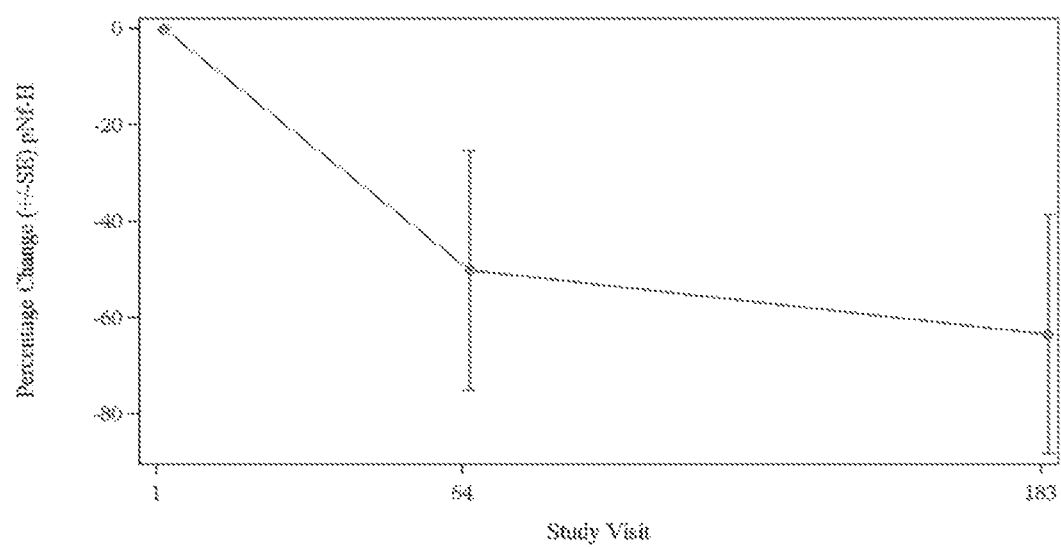
FIG. 27 is a graphical depiction of the drug effect on percentage change in pNF-H (pg/mL) levels in EMBRACE.

Plasma samples from clinical study EMBRACE were analyzed for levels of pNF-H at Study Days 1, 64, and 183 (ISIS 396443). In this analysis, absolute levels of pNF-H were plotted by Study Day. See FIG. 27.

The results of this analysis suggest that significant decline (−50%) occurs by Study Day 64 and this new level appears stable to Study Day 183.

Example 26: Association of HINE-2 Score on Day 183 with pNF-H Levels on Day 64

Plasma samples from clinical study ENDEAR were analyzed for levels of pNF-H at Study Day 64 and the total motor milestone score (HINE-2) was assessed at Study Day 183 (ISIS 396443 and SHAM control). For this analysis, a linear regression model was constructed to determine whether pNF-H levels on Study Day 64 were associated with the total HINE-2 score on Study Day 183. Separate analyses were conducted among subjects who received ISIS 396443 and SHAM Control. Among subjects who received ISIS 396443, log transformed pNF-H levels on Study Day 64 were not statistically significantly associated with total HINE-2 scores on Study Day 183, $p=0.3186$, but trended such that higher pNF-H levels were associated with a lower total HINE-2 score. Among subjects who received SHAM control, log transformed pNF-H levels on Study Day 64 were statistically significantly associated with total HINE-2 scores on Study Day 183, $p=0.0302$, such that higher pNF-H levels were associated with a lower total HINE-2 score. See FIG. 28.

This result suggests that present pNF-H levels can predict future levels of motor milestones among infants with infantile-onset SMA.

Example 27: Association of CHOP INTEND Score on Day 183 with pNF-H Levels on Day 64

Plasma samples from clinical study ENDEAR were analyzed for levels of pNF-H at Study Day 64 and the CHOP INTEND score was assessed at Study Day 183 (ISIS 396443 and SHAM control). For this analysis, a linear regression model was constructed to determine whether pNF-H levels on Study Day 64 were associated with the CHOP INTEND score on Study Day 183. Separate analyses were conducted among subjects who received ISIS 396443 and SHAM Control. Among subjects who received ISIS 396443, log transformed pNF-H levels on Study Day 64 were statistically significantly associated with CHOP INTEND scores on Study Day 183, $p=0.0406$, such that higher pNF-H levels were associated with a lower total CHOP INTEND score. Among subjects who received SHAM control, log transformed pNF-H levels on Study Day 64 were statistically significantly associated with CHOP INTEND scores on Study Day 183, $p=0.0330$, such that higher pNF-H levels were associated with a lower CHOP INTEND score. See FIG. 29.

This result suggests that present pNF-H levels can predict future levels of motor function among infants with infantile-onset SMA.

Example 28: pNF-H Levels Over Time in Surviving Infants with Non-Missing Values at Day 302

Figure 30:
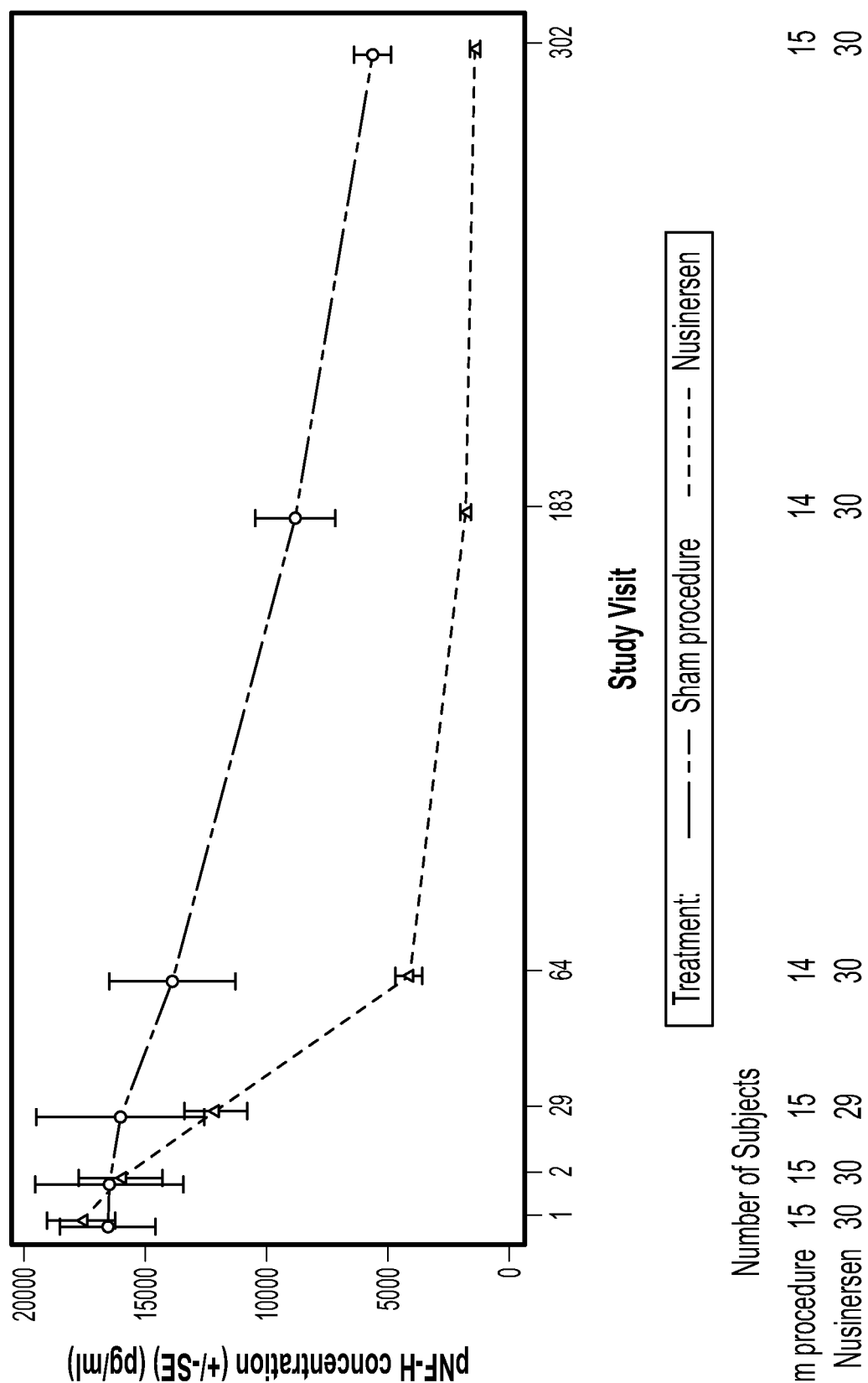
FIG. 30 is a graphical illustration of pNF-H levels over time in surviving infants with non-missing values at Day 302.

Plasma samples from clinical study ENDEAR were analyzed for levels of pNF-H at Study Days 1, 2, 29, 64, 183, and 302 (ISIS 396443 and SHAM procedure). For this analysis, the population was limited to those subjects who survived to Study Day 302 and had a pNF-H level measured at Study Day 302. Absolute values of pNF-H were plotted by study day. Over time among subjects who received the SHAM procedure, mean pNF-H levels decline nearly linearly from approximately 16,000 pg/mL at Study Day 1 to approximately 7,000 pg/mL at Study Day 302. Over time among subjects who received ISIS 396443, mean pNF-H decline from approximately 18,000 pg/mL at Study Day 1 to approximately 4,000 at Study Day 64 and then remain stable at approximately 1,000 pg/ML at Study Day 302. See FIG. 30.

The results of this analysis suggest that the decline in both cohorts is true and not a survival bias.

Example 29: Percentage Change in pNF-H Levels Over Time in Surviving Infants with Non-Missing Values at Day 302

Figure 31:
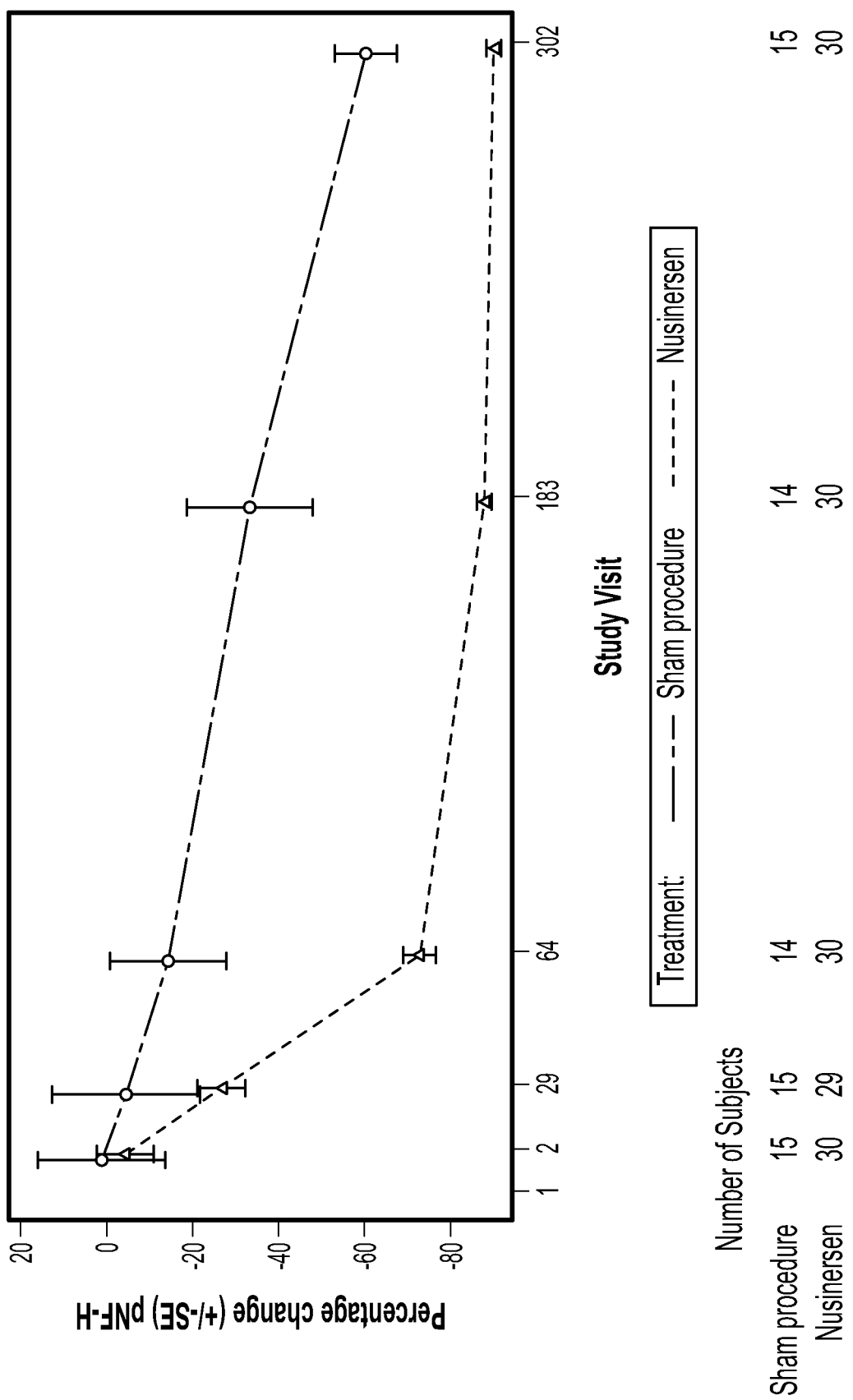
FIG. 31 is a graphic depiction of the percentage change in pNF-H levels over time in surviving infants with non-missing values at Day 302.

Plasma samples from clinical study ENDEAR were analyzed for levels of pNF-H at Study Days 1, 2, 29, 64, 183, and 302 (ISIS 396443 and SHAM procedure). For this analysis, the population was limited to those subjects who survived to Study Day 302 and had a pNF-H level measured at Study Day 302. Change from baseline were plotted by study day. Over time among subjects who received the SHAM procedure, change in pNF-H levels decline nearly linearly to approximately −50% at Study Day 302. Over time among subjects who received ISIS 396443, change in pNF-H decline to approximately −70% at Study Day 64 and then remain stable at approximately −90% at Study Day 302. See FIG. 31.

The results of this analysis suggest that the decline in both cohorts is true and not a survival bias.

Example 30: Association of Peroneal CMAP Amplitude on Day 183 with pNF-H Levels on Day 64

Figure 32:
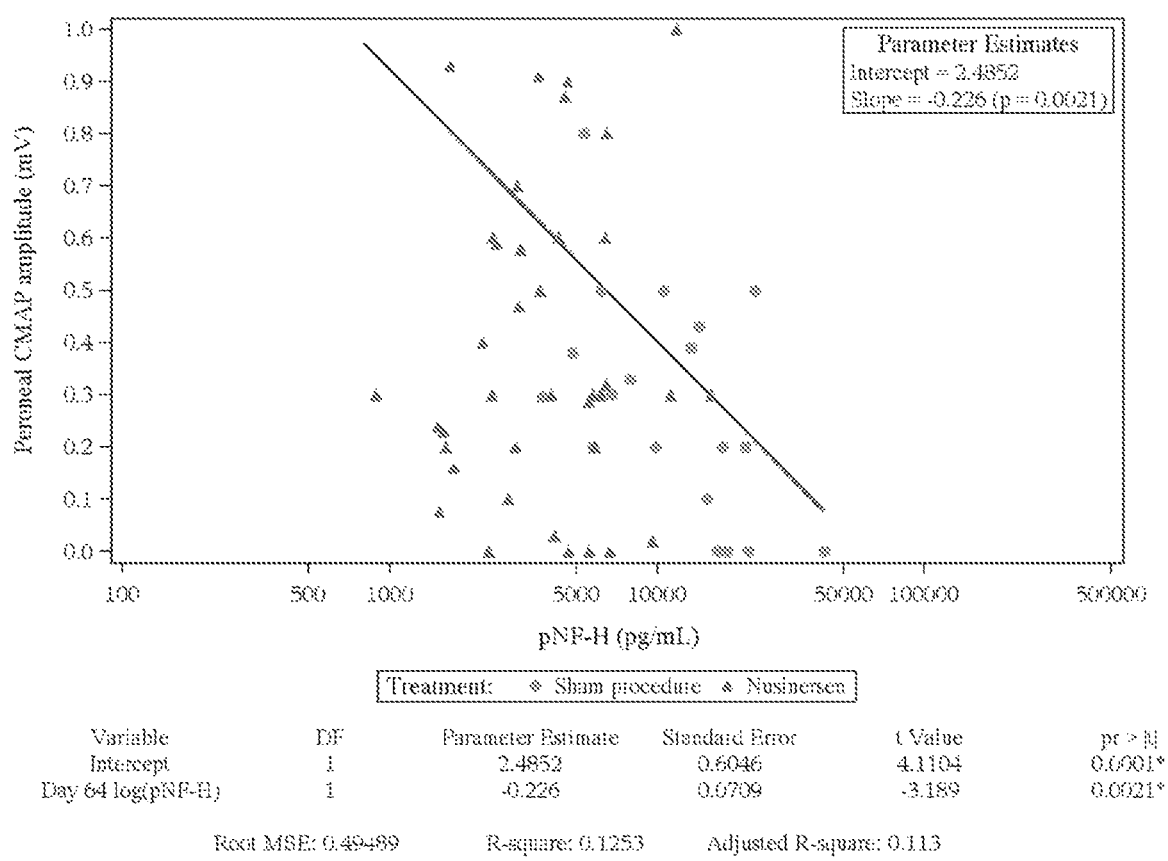
FIG. 32 is a graphical depiction of the association of peroneal CMAP Amplitude on Day 183 with pNF-H levels on Day 64.

Plasma samples from clinical study ENDEAR were analyzed for levels of pNF-H at Study Day 64 and the Peroneal CMAP Amplitude was assessed at Study Day 183 (ISIS 396443 and SHAM control). For this analysis, a linear regression model was constructed to determine whether pNF-H levels on Study Day 64 were associated with the Peroneal CMAP Amplitude on Study Day 183. pNF-H levels on Study Day 64 were significantly associated with Peroneal CMAP Amplitude on Study Day 183, p=0.0021. See FIG. 32.

This result suggests that present pNF-H levels may predict future levels of general motor nerve health among infants with infantile-onset SMA.

Example 31: Association of Peroneal CMAP Amplitude on Day 183 with pNF-H Levels on Day 64

Plasma samples from clinical study ENDEAR were analyzed for levels of pNF-H at Study Day 64 and the Peroneal CMAP Amplitude was assessed at Study Day 183 (ISIS 396443 and SHAM control). For this analysis, a linear regression model was constructed to determine whether pNF-H levels on Study Day 64 were associated with the Peroneal CMAP Amplitude on Study Day 183. Separate analyses were conducted among subjects who received ISIS 396443 and SHAM Control. Among subjects who received ISIS 396443, log transformed pNF-H levels on Study Day 64 were not statistically significantly associated with Peroneal CMAP Amplitude on Study Day 183, p=0.3612, such that higher pNF-H levels were associated with a trend toward lower Peroneal CMAP Amplitude. Among subjects who received SHAM control, log transformed pNF-H levels on Study Day 64 were statistically significantly associated with Peroneal CMAP Amplitude on Study Day 183, p=0.0142, such that higher pNF-H levels were associated with a lower Peroneal CMAP Amplitude. See FIG. 33.

This result suggests that present pNF-H levels may predict future levels of general motor neuron health among infants with infantile-onset SMA.

Example 32: Association of Ulnar CMAP Amplitude on Day 183 with pNF-H Levels on Day 64

Figure 34:
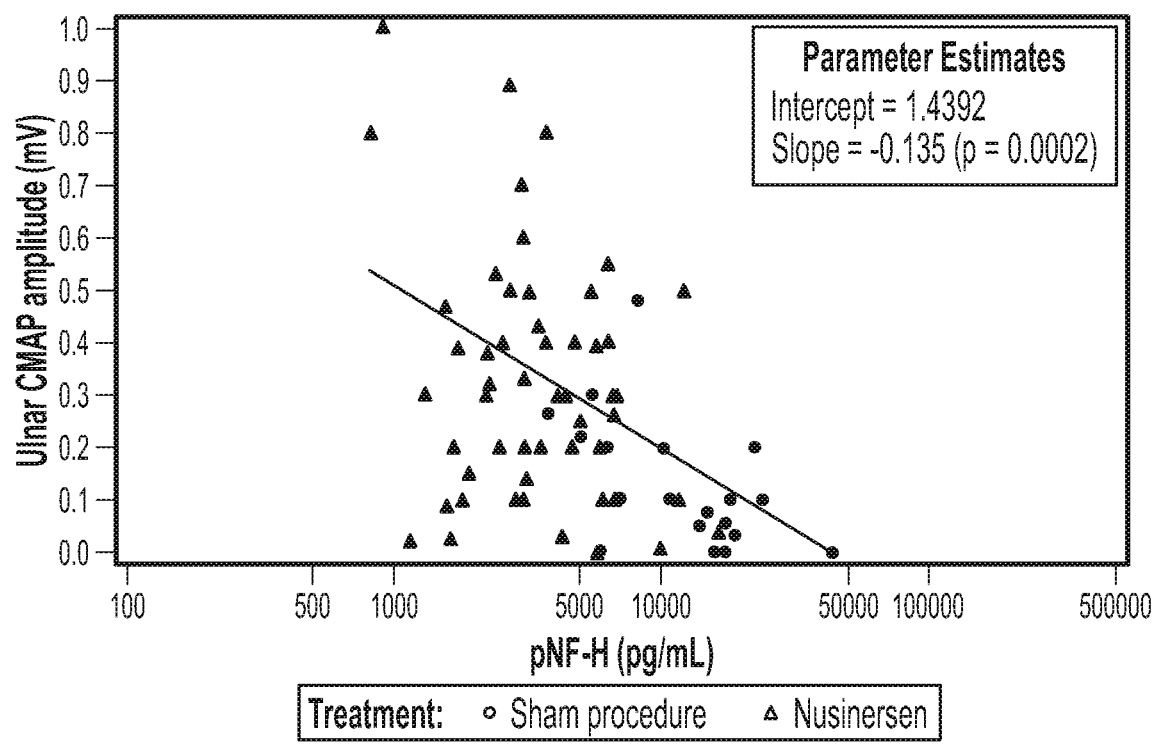
FIG. 34 is a graphical depiction of the association of Ulnar CMAP (compound muscle action potential) Amplitude on Day 183 with pNF-H levels on Day 64. Root MSE: 0.24904; R-square: 0.1746; Adjusted R-square: 0.1633. DF=degrees of freedom; MSE=mean square error.

Plasma samples from clinical study ENDEAR were analyzed for levels of pNF-H at Study Day 64 and the Peroneal CMAP Amplitude was assessed at Study Day 183 (ISIS 396443 and SHAM control). For this analysis, a linear regression model was constructed to determine whether pNF-H levels on Study Day 64 were associated with the Ulnar CMAP Amplitude on Study Day 183. pNF-H levels on Study Day 64 were significantly associated with Ulnar CMAP Amplitude on Study Day 183, p=0.0002. See FIG. 34.

This result suggests that present pNF-H levels may predict future levels of general motor nerve health among infants with infantile-onset SMA.

Example 33: Association of Ulnar CMAP Amplitude on Day 183 with pNF-H Levels on Day 64

Plasma samples from clinical study ENDEAR were analyzed for levels of pNF-H at Study Day 64 and the Ulnar CMAP Amplitude was assessed at Study Day 183 (ISIS 396443 and SHAM control). For this analysis, a linear regression model was constructed to determine whether pNF-H levels on Study Day 64 were associated with the Ulnar CMAP Amplitude on Study Day 183. Separate analyses were conducted among subjects who received ISIS 396443 and SHAM Control. Among subjects who received ISIS 396443, log transformed pNF-H levels on Study Day 64 were not statistically significantly associated with Ulnar CMAP Amplitude on Study Day 183, p=0.0952, such that higher pNF-H levels were associated with a trend toward lower Ulnar CMAP Amplitude. Among subjects who received SHAM control, log transformed pNF-H levels on Study Day 64 were statistically significantly associated with Ulnar CMAP Amplitude on Study Day 183, p=0.0281, such that higher pNF-H levels were associated with a lower Ulnar CMAP Amplitude. See FIG. 35.

This result suggests that present pNF-H levels can predict future levels of general motor neuron health among infants with infantile-onset SMA.

Example 34: ENDEAR Baseline Characteristics Dichotomized by Median pNF-H Levels Below is a table that provides baseline characteristics dichotomized (<15,400 and ≥15,400 pg/mL) by median pNF-H levels from the ENDEAR trial.

|  | Baseline plasma pNF-H (pg/mL) | | |
| --- | --- | --- | --- |
|  | <15,400[a] | ≥15,400[a] | P value[b] |
| Individuals[c], n | 58 | 59 |  |
| Female, n (%) | 32 (55) | 33 (56) | 1.000 |
| Mean (range) age at first dose, wk | 25.8 (7.4, 37.4) | 22.6 (4.3, 33.6) | .0165 |
| Mean (range) age of symptom onset, wk | 9.5 (3, 20) | 7.3 (2, 19) | .0049 |
| Mean (range) age at SMA diagnosis, wk | 16.02 (4, 29) | 12.31 (0, 30) | .0046 |
| Mean (range) disease duration, wks | 13.8 (0.6, 25.9) | 13.2 (0, 23.1) | .5723 |
| Use of ventilation support, n (%) | 14 (24) | 13 (22) | .8290 |
| Mean ± SD total HINE-2 score | 1.6 ± 1.30 | 1.2 ± 0.94 | .0593 |
| Mean ± SD total CHOP INTEND score | 29.49 ± 7.125 | 25.11 ± 7.850 | .0020 |
| Mean ± SD peroneal CMAP amplitude | 0.40 ± 0.328 | 0.28 ± 0.244 | .0353 |
| Mean ± SD ulnar CMAP amplitude | 0.21 ± 0.162 | 0.23 ± 0.164 | .6259 |

CHOP INTEND = Children's Hospital of Philadelphia Infant Test of Neuromuscular Disorders;
CMAP = compound muscle action potential;
HINE-2 = Hammersmith Infant Neurological Examination Section 2.
[a]The median of baseline pNF-H.
[b]Results for continuous variables are from Student's two-sample t-test and results for proportions are from Fisher's exact test.
[c]Number of participants in the table refers to participants who have non-missing baseline pNF-H in either category.

Example 35: Correlations Between Baseline Characteristics and Log(pNF-H) Levels in ENDEAR The table below provides correlations between baseline characteristics and log(pNF-H) levels in the ENDEAR trial.

|  | Pearson correlation coefficient | Probability > r under H0: Rho = 0 |
| --- | --- | --- |
| Weight (kg), n = 117 | −0.11 | .2201 |
| Age of symptom onset (weeks), n = 117 | −0.20 | .0344 |
| Age at first dose (weeks), n = 117 | −0.24 | .0106 |
| Age at SMA diagnosis (weeks), n = 117 | −0.25 | .0064 |
| Gestational age (weeks), n = 117 | 0.01 | .9438 |
| Disease duration (weeks), n = 117 | −0.09 | .3183 |
| HINE motor milestone score, n = 117 | −0.13 | .1786 |
| CHOP INTEND, n = 117 | −0.30 | .0012 |
| CMAP: peroneal nerve amplitude, n = 108 | −0.13 | .1842 |
| CMAP: ulnar amplitude, n = 111 | −0.16 | .1002 |

Example 36: CHERISH Baseline Characteristics Dichotomized by Median pNF-H Levels Below is a table that provides baseline characteristics dichotomized (<1,200 and ≥1,200 pg/mL) by median pNF-H levels from the CHERISH trial.

|  | Baseline plasma pNF-H (pg/mL) | | |
| --- | --- | --- | --- |
|  | <1,200[a] | ≥1,200[a] | P value[b] |
| Individuals[c], n | 62 | 64 |  |
| Mean (range) weight, kg | 16.77 (10.0, 36.4) | 12.59 (8.5, 24.0) | <.0001 |
| Mean (range) age of symptom onset (weeks) | 48.57 (26.1, 78.2) | 48.34 (26.1, 86.9) | .9306 |
| Mean (range) age at first dose (weeks) | 269.10 (131.9, 482.1) | 167.45 (107.3, 379.9) | <.0001 |
| Mean (range) age at SMA diagnosis (weeks) | 89.99 (43.5, 208.6) | 78.28 (0.0, 165.1) | .0542 |
| Mean (range) disease duration (weeks) | 217.49 (97.4, 408.9) | 116.10 (34.8, 315.1) | <.0001 |
| Mean ± SD HFMSE total score | 21.58 ± 8.231 | 21.53 ± 7.904 | .9726 |
| Mean ± SD Upper Limb Module Test score | 20.81 ± 5.847 | 17.45 ± 5.741 | .0015 |

HFMSE = Hammersmith Functional Motor Scale - Expanded.
[a]The median of baseline pNF-H.
[b]Results for continuous variables are from Student's two-sample t-test and results for proportions are from Fisher's exact test.
[c]Number of participants in the table refers to participants who have non-missing baseline pNF-H in either category.

Example 37: Correlations Between Baseline Characteristics and Log(pNF-H) Levels in CHERISH The table below provides correlations between baseline characteristics and log(pNF-H) levels in the CHERISH trial.

|  | Pearson correlation coefficient | Probability > r under H0: Rho = 0 |
| --- | --- | --- |
| Weight (kg), n = 126 | −0.44 | <.0001 |
| Age of symptom onset (weeks), n = 126 | 0.05 | .5469 |
| Age at first dose (weeks), n = 126 | −0.63 | <.0001 |
| Age at SMA diagnosis (weeks), n = 126 | −0.03 | .7257 |
| Disease duration (weeks), n = 126 | −0.64 | <.0001 |
| HFMSE score, n = 126 | 0.10 | .2436 |
| WHO motor milestones, n = 126 | 0.14 | .1154 |
| Upper Limb Module Test score, n = 126 | −0.20 | .0280 |

HFMSE = Hammersmith Functional Motor Scale - Expanded.
WHO = World Health Organization

Figure 36A:
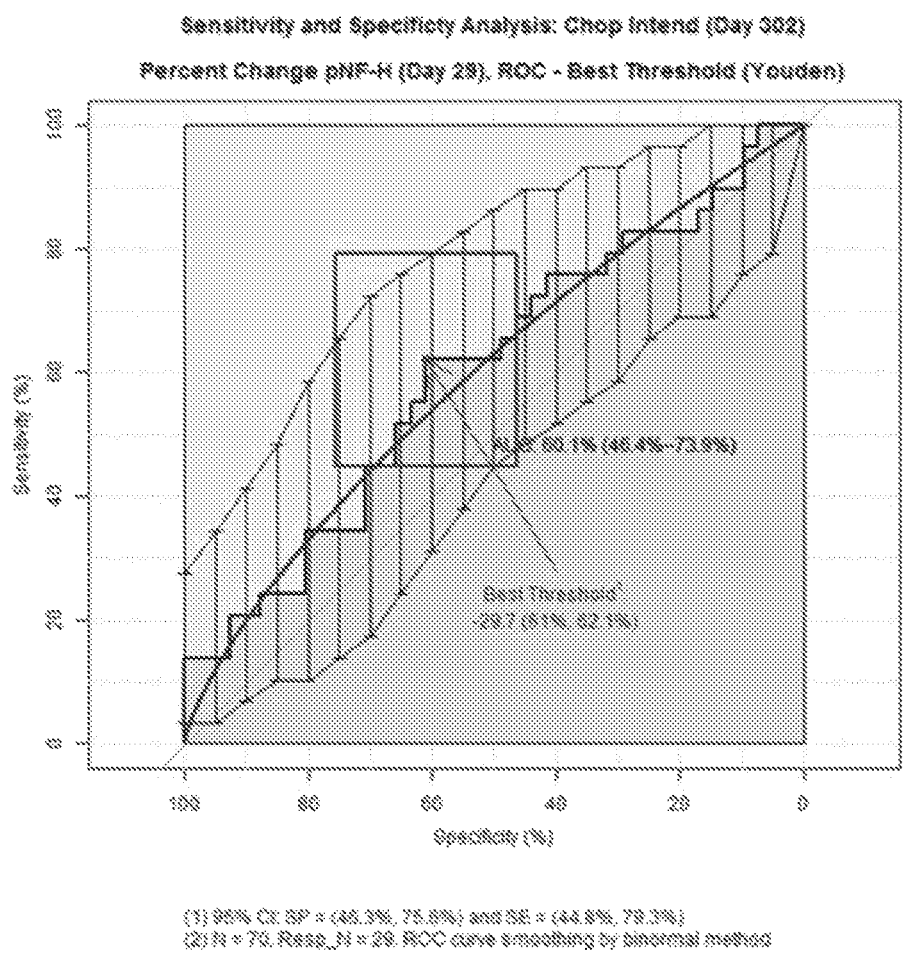
FIGS. 36A-36C are receiver operating characteristic (ROC) graphs depicting the effectiveness of measuring percent change in pNF-H levels at Day 29 (FIG. 36A), Day 64 (FIG. 36B), and Day 183 (FIG. 36C) at predicting motor function at Day 302.
Figure 36B:
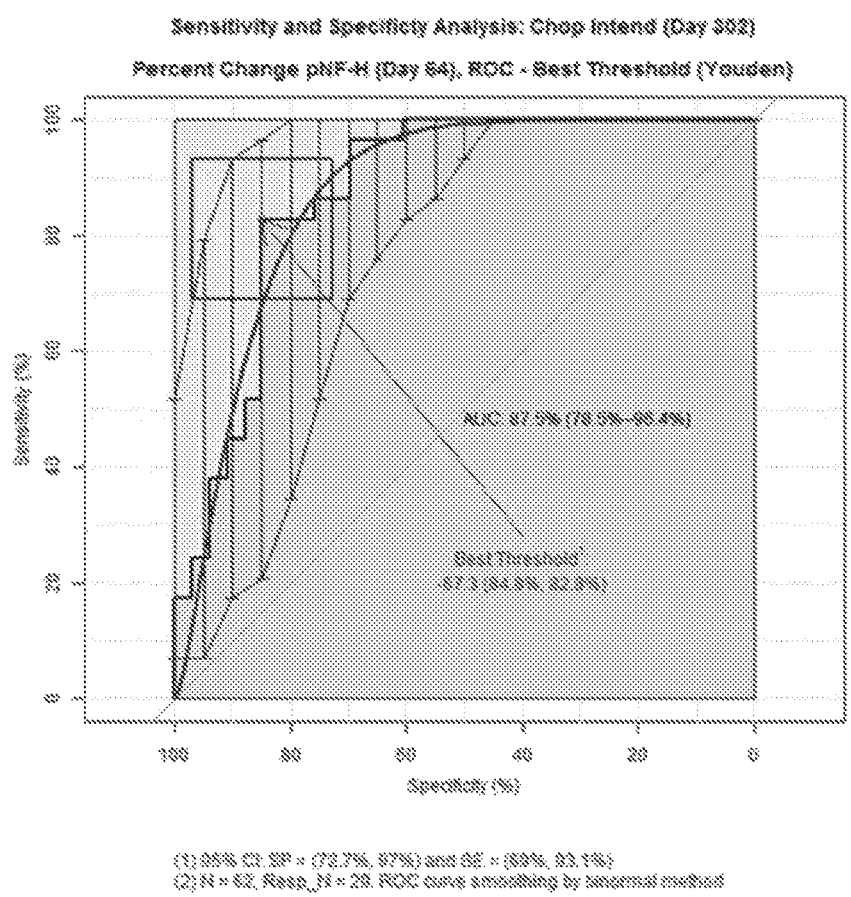
Figure 36C:
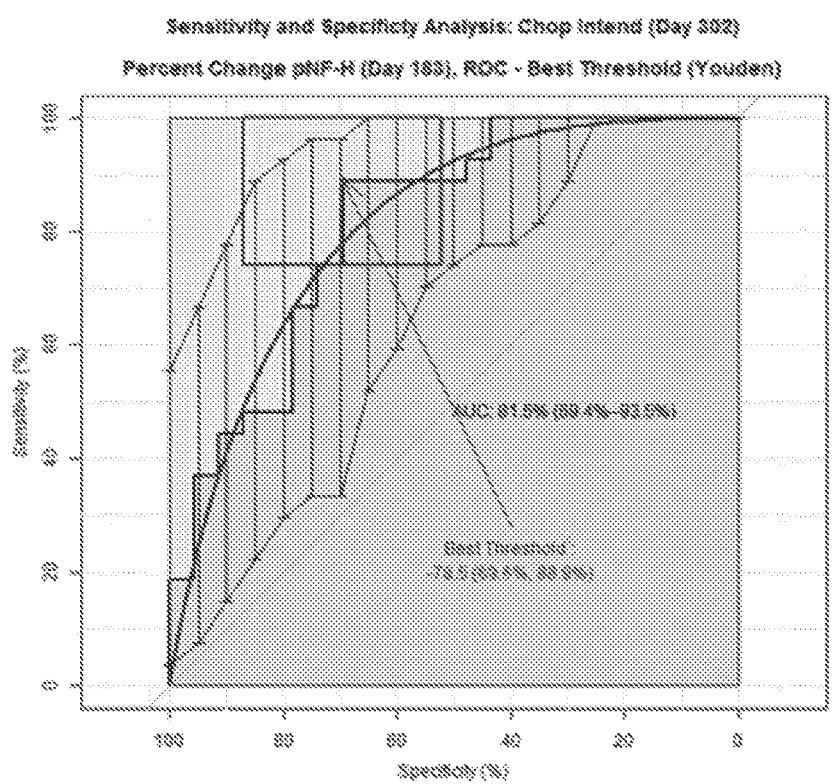
Figure 37A:
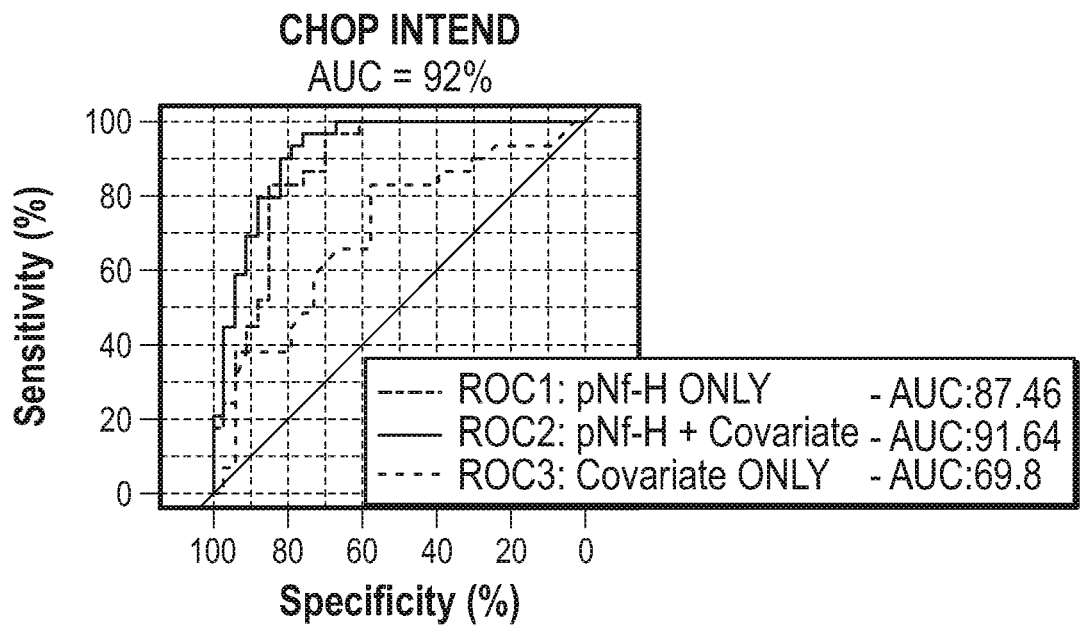
FIGS. 37A-37B are graphs depicting the effectiveness of measuring percent change in pNF-H levels as a predictor of CHOP INTEND responders (FIG. 37A) and motor milestone responders (FIG. 37B) in ENDEAR.
Figure 37B:
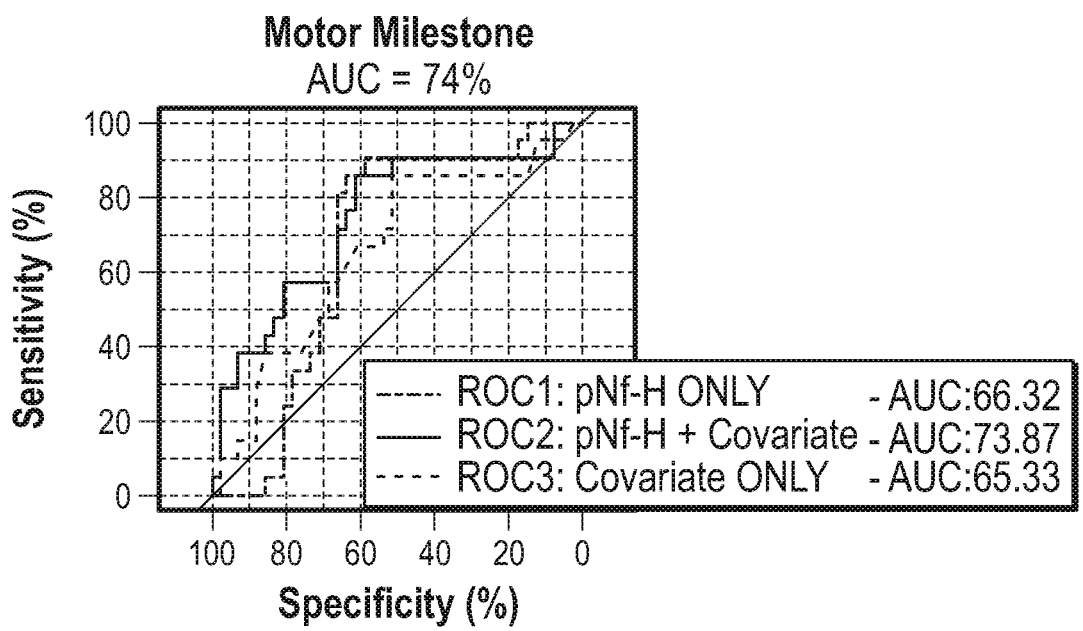
Figure 38A:
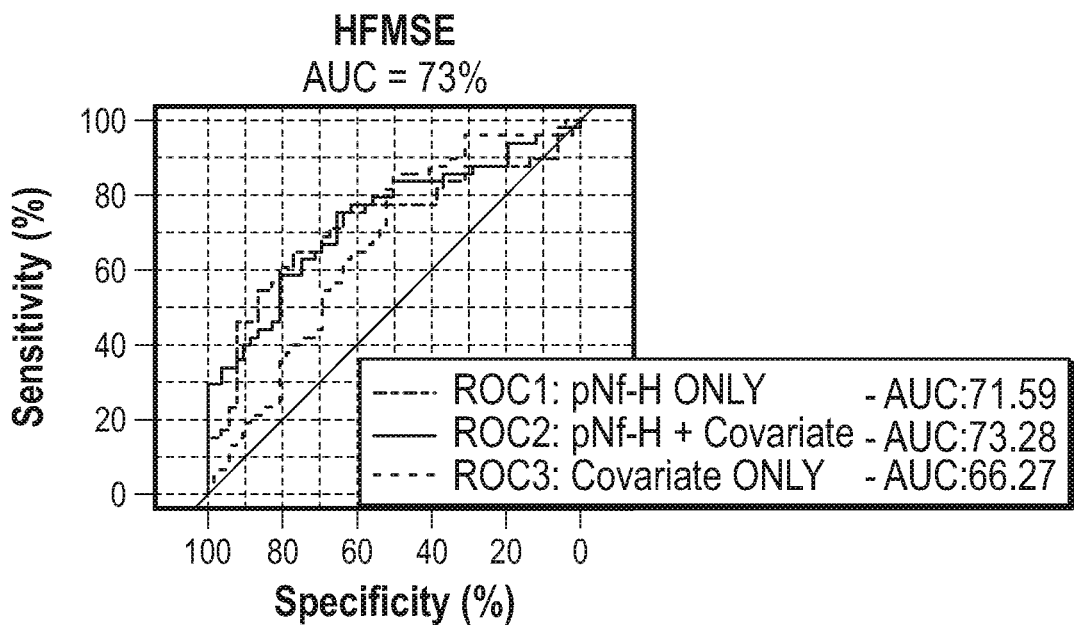
FIGS. 38A-38C are graphs depicting the effectiveness of measuring percent change in pNF-H levels as a predictor of HFMSE responders (FIG. 38A), RULM responders (FIG. 38B), and WHO responders (FIG. 38C) in CHERISH.
Figure 38B:
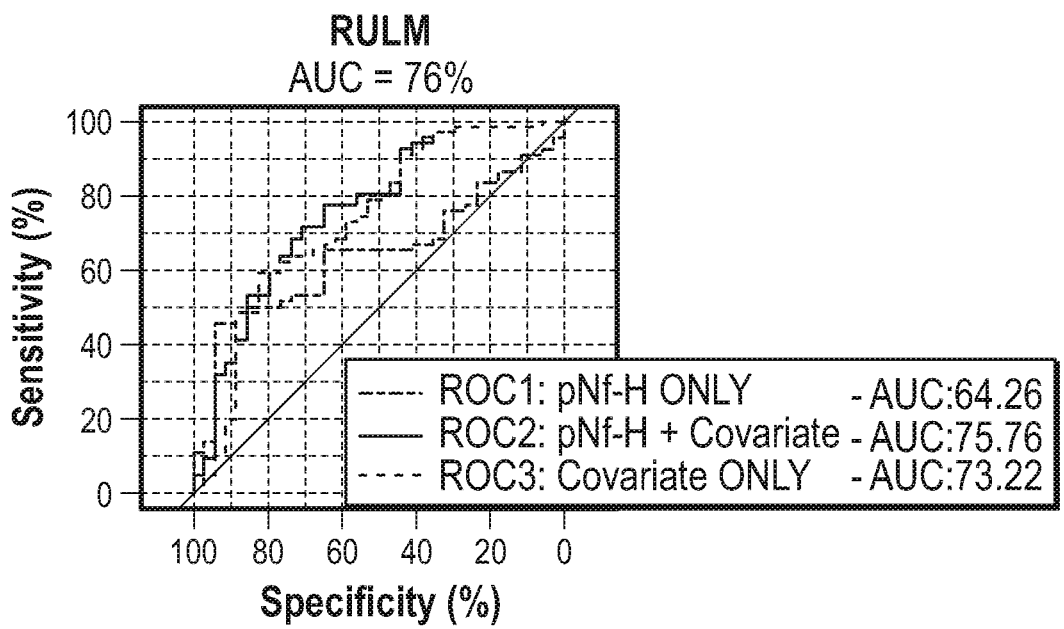
Figure 38C:
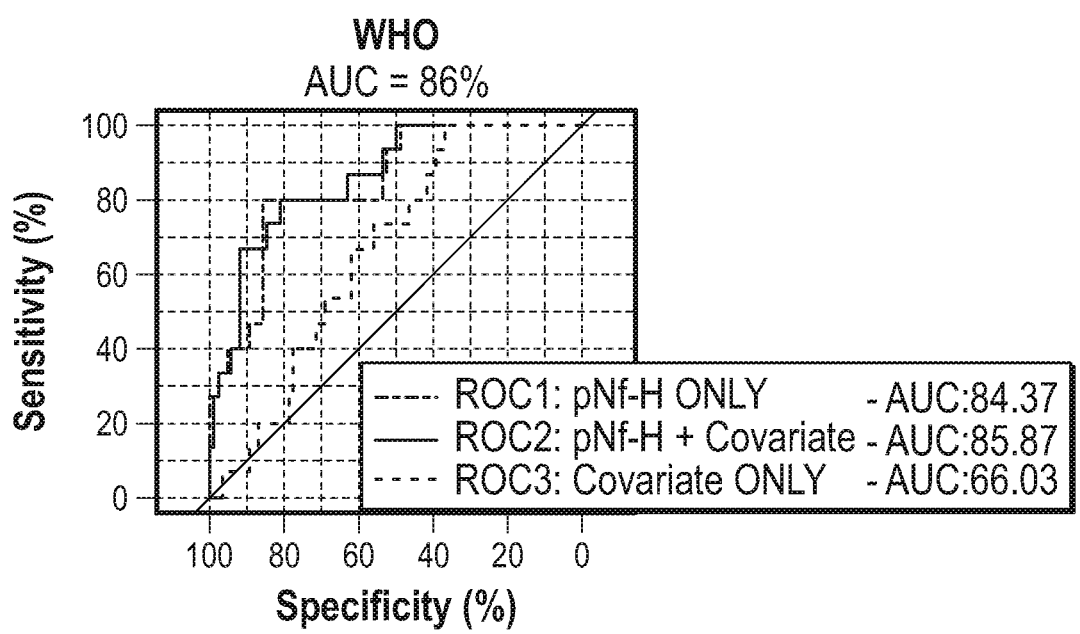

Example 38: Predicting Future Motor Function by Measuring Percent Change in pNF-H Levels after Treatment Receiver operating characteristic (ROC) curves were used in an effort to select the time period for measuring percent change in neurofilament levels that best predicts future motor function in a treated individual. In ENDEAR, percent change in pNF-H levels were measured at each of Day 29, Day 64, and Day 183 and compared with motor function of the treated subject at Day 302. ROC curves revealed that percent change in pNF-H levels at Day 64 is better at predicting motor function at Day 302 than percent change in pNF-H levels at Day 29 or Day 183. See FIGS. 36A-36C. In ENDEAR, even after controlling for age of first dose, percent change in pNF-H levels at Day 64 predicted CHOP INTEND (≥4 point improvement) and motor milestone (more HINE-2 motor milestones with improvement than worsening) responders at Day 302. See FIGS. 37A-B. In CHERISH, even after controlling for disease duration, percent change in pNF-H levels at Day 85 predicted HFMSE (Hammersmith Functional Motor Scale—Expanded; ≥3 point improvement), RULM (Revised Upper Limb Module; ≥2 point improvement), and WHO (World Health Organization; attainment of ≥1 motor milestone) responders at Day 456. See FIGS. 38A-38C.

Figure 39A:
FIGS. 39A-39B are graphs depicting baseline cerebrospinal fluid pNF-H levels versus age at first dose by patient population (FIG. 39A) and SMN2 copy number (FIG. 39B).
Figure 39B:
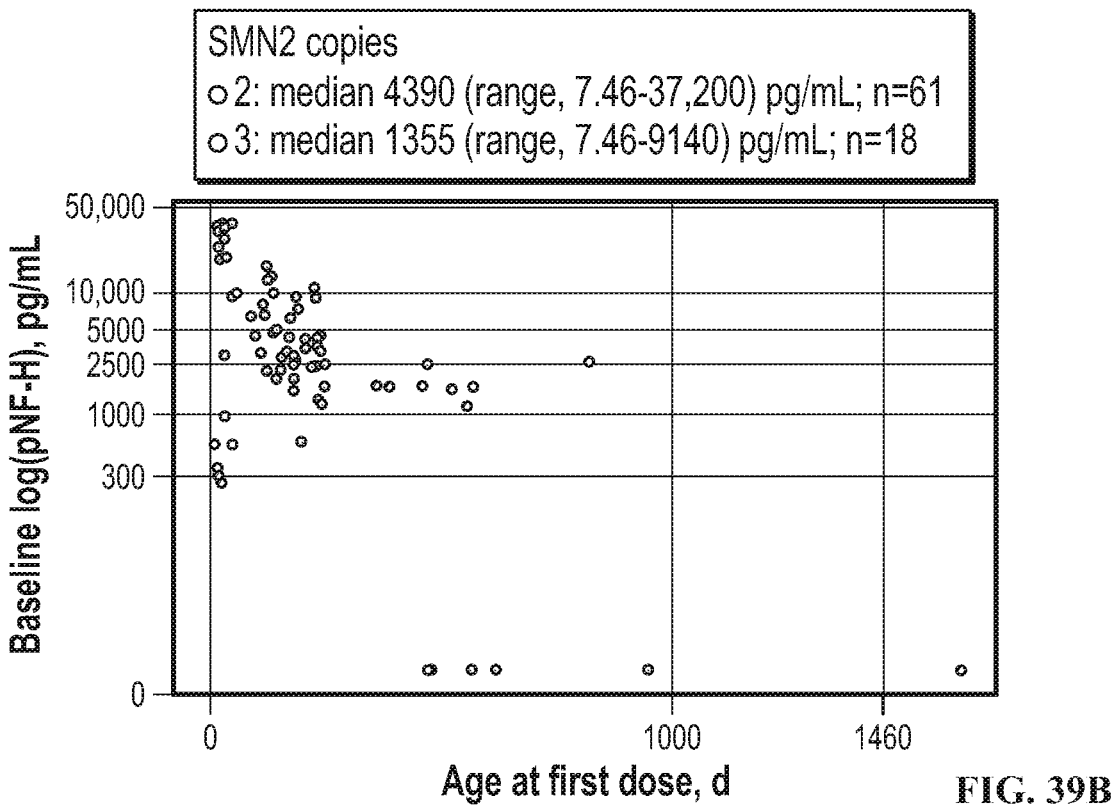
Figure 40:
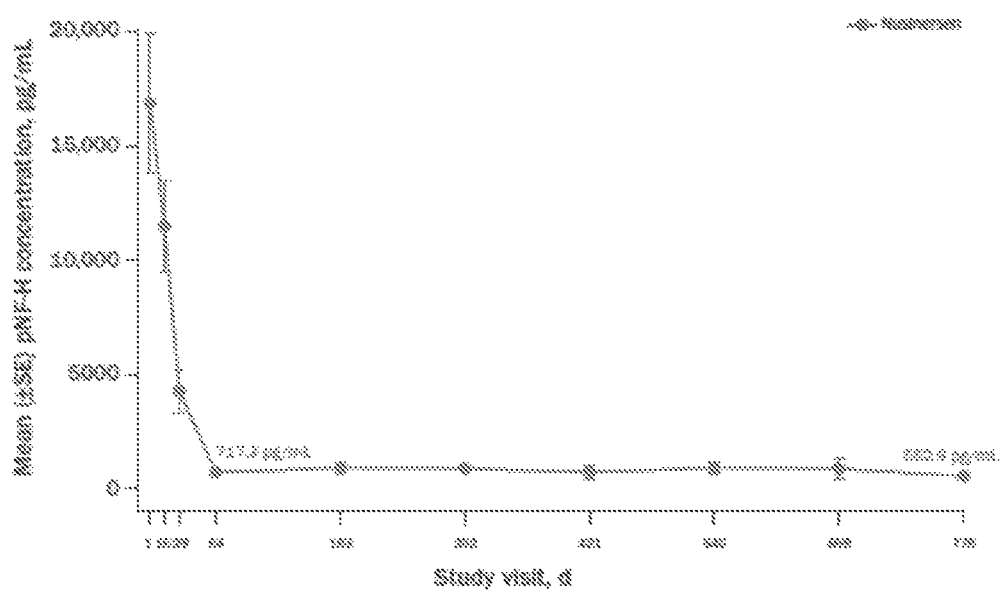
FIG. 40 is a graph depicting decline in cerebrospinal fluid pNF-H levels following treatment with nusinersen.

Example 39: Cerebral Spinal Fluid pNF-H Levels at Baseline and Following Treatment with Nusinersen Baseline cerebral spinal fluid (CSF) pNF-H levels were measured in presymptomatic, infantile-onset, and later-onset patients as well as patients with 2 or 3 copies of SMN2. Baseline pNF-H levels in CSF were highest in presymptomatic infants and the youngest infants with 2 copies of SMN2. See FIGS. 39A-39B. In the NURTURE study, treatment with nusinersen was associated with a rapid decline in pNF-H levels in CSF, followed by stabilization. See FIG. 40.

Example 40: Comparison of Phosphorylated Neurofilament Heavy Chain (pNF-H) and Neurofilament Light Chain (NF-L) in Different Matrices Among Multiple Spinal Muscular Atrophy Populations Concentrations of pNF-H and NF-L were compared in plasma and cerebrospinal fluid (CSF) in individuals from nusinersen clinical trials with presymptomatic (most likely to develop Type I/II), infantile-onset (has or most likely to develop Type I/II) or later-onset SMA (has or most likely to develop Type II/III). pNF-H concentrations in plasma and CSF were evaluated using the ProteinSimple™ SimplePlex ELLA immunoassay. NF-L concentrations were evaluated using the SIMOA assay (Quanterix™). Results reported below are in units of pg/mL.

Figure 41A:
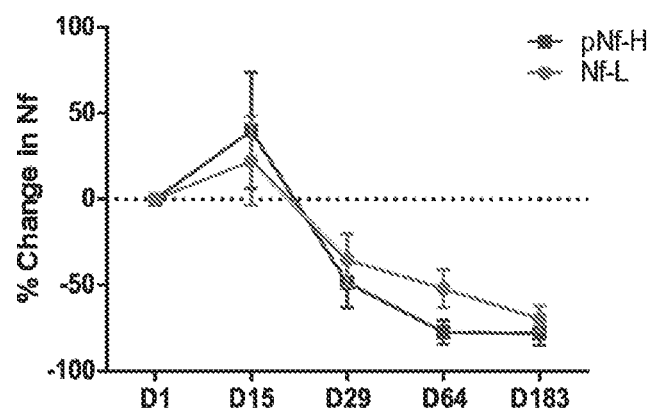
FIGS. 41A-41D are graphs depicting percent change in pNF-H and NF-L levels following treatment with nusinersen in CSF of presymptomatic subjects (FIG. 41A), CSF of infantile-onset subjects (FIG. 41B), plasma of infantile-onset subjects (FIG. 41C), and plasma of later-onset subjects (FIG. 41D).
Figure 41B:
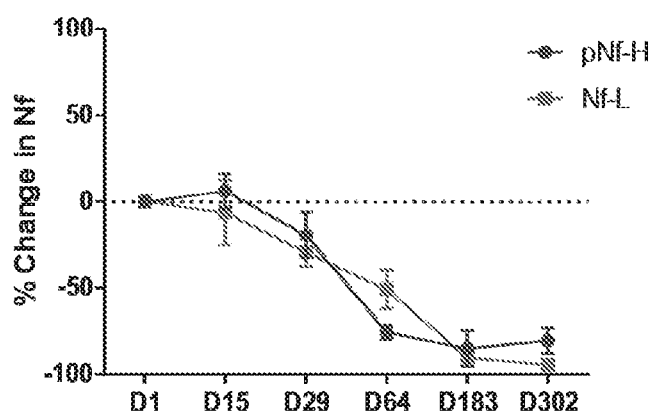
Figure 41C:
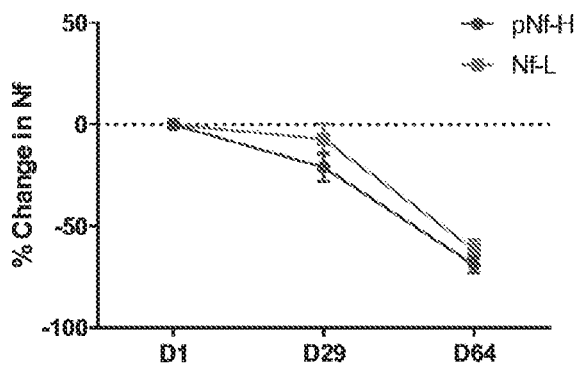
Figure 41D:
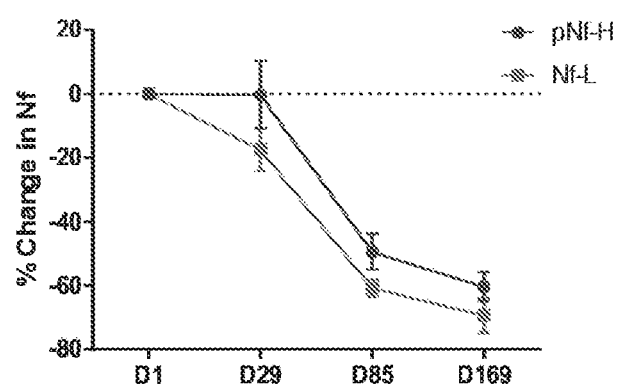
Figure 41E:
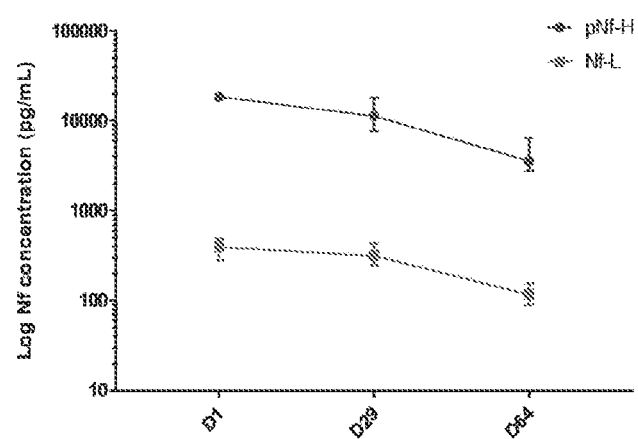
FIGS. 41E-41F are graphs depicting the absolute value change in pNF-H and NF-L levels following treatment with nusinersen in plasma of infantile-onset subjects (FIG. 41E) and plasma of later-onset subjects (FIG. 41F).
Figure 41F:
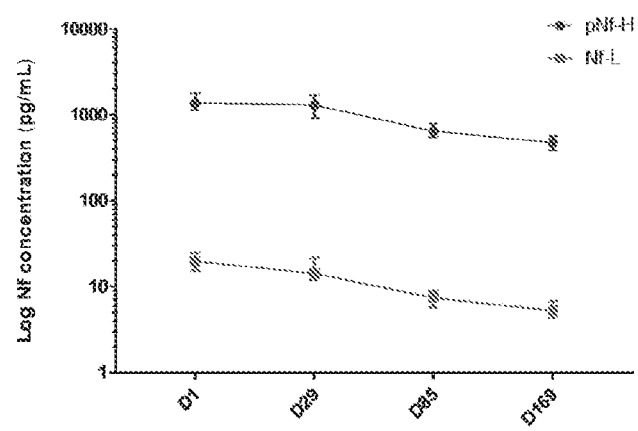

For each SMA population, pNF-H and NF-L concentrations were similar in CSF; however, in plasma, NF-L concentrations were lower than those of pNF-H. The difference between NF-L and pNF-H concentrations in plasma was more pronounced in presymptomatic infants versus those with infantile-onset SMA. In CSF, pNF-H and NF-L concentrations declined over time on nusinersen treatment at similar rates in the presymptomatic (percentage reduction at Day 183: FIG. 41A) and the infantile-onset (percentage reduction at Day 302: FIG. 41B) SMA cohorts. Comparable results were demonstrated in plasma pNF-H and NF-L concentrations in the infantile-onset (percentage reduction at Day 64: FIG. 41C) and the later-onset (percentage reduction at Day 169: FIG. 41D) SMA cohorts. The absolute values of the data shown in FIG. 41C are presented in FIG. 41E, and the absolute values of the data shown in FIG. 41D are presented in FIG. 41F. Additionally, the rates of change in pNF-H concentrations in plasma and CSF were similar in both the presymptomatic and infantile-onset SMA cohorts. For NF-L, plasma and CSF concentrations declined over a similar trajectory in the infantile-onset cohort.

Overall, the baseline pNF-H and NF-L geometric mean (95% CI) concentrations were 20139 (10075-40257) and 7272 (3287-16090) pg/mL, respectively, among presymptomatic infants with 2 SMN2 copies and 952 (367-2470) and 519 (231-1164) pg/mL, respectively, among those with 3 SMN2 copies. In infantile-onset SMA participants, baseline pNF-H and NF-L geometric mean (95% CI) concentrations were 3791 (2980-4823) and 3718 (2832-4882) pg/mL, respectively. In later-onset SMA participants, baseline pNF-H and NF-L geometric mean (95% CI) concentrations were 381 (331-438) and 185 (154-222) pg/mL, respectively.

Thus, like plasma pNF-H levels, CSF pNF-H and NF-L levels appear highest in presymptomatic SMA participants with 2 SMN2 copies and lowest in those with later-onset SMA.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating spinal muscular atrophy (SMA) in a human subject in need thereof, comprising:
   measuring a neurofilament level in a first biological sample obtained from the human subject before initiation of an SMA therapy, wherein the neurofilament measured in the first biological sample is a phosphorylated neurofilament heavy chain or a neurofilament light chain, and wherein the first biological sample is blood, serum, plasma, or cerebrospinal fluid;
   administering an SMA therapy to the human subject; and
   measuring a neurofilament level in a second biological sample obtained from the human subject after initiation of the SMA therapy, wherein the neurofilament measured in the second biological sample is a phosphorylated neurofilament heavy chain or a neurofilament light chain, and wherein the second biological sample is blood, serum, plasma, or cerebrospinal fluid.

2. The method of claim 1, wherein the neurofilament level measured in the second biological sample is lower than the neurofilament level measured in the first biological sample.

3. The method of claim 2, wherein the neurofilament level measured in the second biological sample is between 10% to 95% of the neurofilament level measured in the first biological sample.

4. The method of claim 1, wherein the second biological sample is obtained from the human subject 40-90 days after initiation of the SMA therapy.

5. The method of claim 4, wherein the neurofilament level measured in the second biological sample is reduced by at least 50% compared to the neurofilament level measured in the first biological sample.

6. The method of claim 4, wherein the neurofilament level measured in the second biological sample is reduced by less than 50% compared to the neurofilament level measured in the first biological sample.

7. The method of claim 4, wherein the dose of the SMA therapy is changed for a subsequent administration to the human subject based upon the percent reduction in neurofilament level measured in the second biological sample as compared to the neurofilament level measured in the first biological sample.

8. The method of claim 1, wherein the neurofilament level measured in the second biological sample is higher than the neurofilament level measured in the first biological sample.

9. The method of claim 8, wherein administration of the SMA therapy is discontinued.

10. The method of claim 9, wherein a different SMA therapy is administered to the human subject after discontinuing the SMA therapy.

11. The method of claim 10, wherein the different SMA therapy is nusinersen or a nusinersen salt.

12. The method of claim 1, wherein administration of the SMA therapy is continued.

13. The method of claim 1, wherein the SMA therapy is nusinersen or a nusinersen salt.

14. The method of claim 1, wherein the SMA therapy is nusinersen sodium.

15. The method of claim 1, wherein the SMA therapy is olesoxime, AVX-101, CK-2127107, RG7916, RG7800, RO7034067, LMI070, or SRK-015.

16. The method of claim 1, wherein the neurofilament level in the first biological sample is above 300 pg/mL.

17. The method of claim 1, wherein the neurofilament level in the first biological sample is above 5,000 pg/mL.

18. The method of claim 1, wherein the SMA therapy is a p38aDMAPK inhibitor, a DcpS inhibitor, a JNK inhibitor, a histone deacetylase inhibitor, an aminoglycoside, or a quinazoline derivative.

19. A method of treating spinal muscular atrophy (SMA) in a human subject in need thereof, comprising:
   measuring a neurofilament level in a first biological sample obtained from the human subject before administration of a candidate amount of an SMA therapy, wherein the neurofilament measured in the first biological sample is a phosphorylated neurofilament heavy chain or a neurofilament light chain, and wherein the first biological sample is blood, serum, plasma, or cerebrospinal fluid;
   measuring a neurofilament level in a second biological sample obtained from the human subject after administration of the candidate amount of the SMA therapy, wherein the neurofilament measured in the second biological sample is a phosphorylated neurofilament heavy chain or a neurofilament light chain, wherein the second biological sample is blood, serum, plasma, or cerebrospinal fluid, and wherein the neurofilament level in the second biological sample is lower than the neurofilament level in the first biological sample, thereby indicating that the candidate amount of the SMA therapy is a therapeutically effective amount;

administering the therapeutically effective amount of the SMA therapy to the human subject after having measured the lowered neurofilament level in the second biological sample.

20. The method of claim 19, wherein the SMA therapy is nusinersen or a nusinersen salt.

21. The method of claim 19, wherein the SMA therapy is olesoxime, AVX-101, CK-2127107, RG7916, RG7800, RO7034067, LMI070, or SRK-015.

22. The method of claim 19, wherein the SMA therapy is a p38aDMAPK inhibitor, a DcpS inhibitor, a JNK inhibitor, a histone deacetylase inhibitor, an aminoglycoside, or a quinazoline derivative.

* * * * *

UNITED STATES PATENT AND TRADEMARK OFFICE
CERTIFICATE OF CORRECTION

| | |
|---|---|
| PATENT NO. | : 11,474,113 B2 |
| APPLICATION NO. | : 16/963914 |
| DATED | : October 18, 2022 |
| INVENTOR(S) | : Wildon Farwell et al. |

It is certified that error appears in the above-identified patent and that said Letters Patent is hereby corrected as shown below:

On the Title Page

Column 1, Item (73) Assignee:
Line 1, delete "Biosen" and insert -- Biogen --.

Column 2, item (56) OTHER PUBLICATIONS:
Line 18, delete "Semm" and insert -- Serum --.

Signed and Sealed this
Thirteenth Day of December, 2022

Katherine Kelly Vidal
*Director of the United States Patent and Trademark Office*